US010604759B2

(12) United States Patent
Shi et al.

(10) Patent No.: US 10,604,759 B2
(45) Date of Patent: Mar. 31, 2020

(54) TARGETING GLIOBLASTOMA STEM CELLS THROUGH THE TLX-TET3 AXIS

(71) Applicant: City of Hope, Duarte, CA (US)

(72) Inventors: Yanhong Shi, Arcadia, CA (US); Qi Cui, Duarte, CA (US); Su Yang, San Diego, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 16/069,854

(22) PCT Filed: Jan. 13, 2017

(86) PCT No.: PCT/US2017/013505
§ 371 (c)(1),
(2) Date: Jul. 12, 2018

(87) PCT Pub. No.: WO2017/123996
PCT Pub. Date: Jul. 20, 2017

(65) Prior Publication Data
US 2019/0032055 A1 Jan. 31, 2019

Related U.S. Application Data

(60) Provisional application No. 62/279,588, filed on Jan. 15, 2016.

(51) Int. Cl.
*C12N 15/113* (2010.01)
*A61P 35/00* (2006.01)
*A61K 31/713* (2006.01)
*A01K 67/027* (2006.01)
*A61K 31/203* (2006.01)

(52) U.S. Cl.
CPC ........ *C12N 15/113* (2013.01); *A01K 67/0271* (2013.01); *A61K 31/203* (2013.01); *A61P 35/00* (2018.01); *A01K 2207/12* (2013.01); *A01K 2227/105* (2013.01); *A01K 2267/0331* (2013.01); *C12N 2310/14* (2013.01); *C12N 2310/351* (2013.01); *C12N 2310/3517* (2013.01); *C12N 2310/531* (2013.01); *C12N 2320/32* (2013.01); *C12N 2740/15043* (2013.01)

(58) Field of Classification Search
None
See application file for complete search history.

(56) References Cited

U.S. PATENT DOCUMENTS 8,992,923 B2* 3/2015 Liu .................. C07K 14/70567
424/130.1
2006/0040321 A1 2/2006 Shi et al.
2011/0236894 A1 9/2011 Rao et al.
2013/0230453 A1* 9/2013 Wookey ............ C07K 16/2869
424/1.11

2013/0302257 A1 11/2013 Minko et al.
2014/0088170 A1 3/2014 Shi et al.
2014/0107180 A1* 4/2014 Macleod ............ C12N 15/1138
514/44 A
2015/0125478 A1 5/2015 Weinschenk et al.
2015/0168377 A1 6/2015 Liu et al.

FOREIGN PATENT DOCUMENTS

WO WO-98/028418 A1 7/1998
WO WO-2006/005460 A2 1/2006
WO WO-2006/005460 A3 1/2006
WO WO-2008/087040 A2 7/2008
WO WO-2008/087040 A3 7/2008

OTHER PUBLICATIONS

Liu et al, Targeted delivery of Dicer-substrate siRNAs using a dual targeting peptide decorated dendrimer delivery system. Nanomedicine: NBM 2014, vol. 10, pp. 1627-1636.*
Allegra, A. et al. The cancer stem cell hypothesis: a guide to potential molecular targets. Cancer Invest 32, 470-495 (2014).
Antoniou, A. et al. Cancer stem cells, a fuzzy evolving concept: a cell population or a cell property? Cell Cycle 12, 3743-3748 (2013).
Bao, S. et al. Glioma stem cells promote radioresistance by preferential activation of the DNA damage response. Nature 444, 756-760 (2006, Epub Oct. 18, 2006).
Behr, J. P. The proton sponge: A trick to enter cells the viruses did not exploit. Chimia 51, 34-36 (1997).
Brown, C. E. et al. Recognition and killing of brain tumor stem-like initiating cells by CD8+ cytolytic T cells. Cancer Res 69, 8886-8893 (2009).
Cambon, K. et al. Lentiviral-mediated gene transfer of siRNAs for the treatment of Huntington's disease. Methods Mol Biol 1010, 95-109 (2013).
Cui, Q. et al. (Feb. 3, 2016). "Downregulation of TLX induces TET3 expression and inhibits glioblastoma stem cell self-renewal and tumorigenesis," *Nat Commun* 7:10637.
Desgrosellier, J. S. and Cheresh, D. A. Integrins in cancer: biological implications and therapeutic opportunities. Nat Rev Cancer 10, 9-22 (2010).
Dutta, T., Garg, M., and Jain, N. K. Poly(propyleneimine) dendrimer and dendrosome mediated genetic immunization against hepatitis B. Vaccine 26, 3389-3394 (2008).

(Continued)

*Primary Examiner* — Tracy Vivlemore
(74) *Attorney, Agent, or Firm* — Mintz Levin Cohn Ferris Glovsky and Popeo, P.C.

(57) ABSTRACT

Methods and compositions capable of modulating activity of TLX (NR2E1), a nuclear receptor essential for neural stem cell self-renewal are provided. The modulations may comprise downregulating TLX expression and/or modulating TET3. In addition, methods of delivering shRNAs using dendrimer nanoparticles into glioblastoma stem cells are provided. The methods and compositions are useful for treating and preventing the progression of brain cancer, e.g. glioblastoma.

17 Claims, 25 Drawing Sheets
Specification includes a Sequence Listing.

(56) References Cited

OTHER PUBLICATIONS

Ford, K.G. et al. (Jan. 2001). "Protein transduction: an alternative to genetic intervention," *Gene Therapy* 8:1-4.
GenBank Accession No. NM 003269.4, Sep. 23, 2018, 5 pages.
GenBank Accession No. NM 001287491.1, Sep. 2, 2018, 6 pages.
GenBank Accession No. NM 144993.1, Dec. 10, 2013, 7 pages.
Godlewski, J. et al. MicroRNAs and glioblastoma; the stem cell connection. Cell Death Differ 17, 221-228 (2010).
Haffner, M. C. et al. Global 5-hydroxymethylcytosine content is significantly reduced in tissue stem/progenitor cell compartments and in human cancers. Oncotarget 2, 627-637 (2011).
Haussecker, D. et al. RNA interference. Drugging RNAi. Science 347, 1069-1070 (2015).
Hu, Y. et al. ELDA: extreme limiting dilution analysis for comparing depleted and enriched populations in stem cell and other assays. J Immunol Methods 347, 70-78 (2009, Epub Jun. 28, 2009).
Irizarry, R. A. et al. Exploration, normalization, and summaries of high density oligonucleotide array probe level data. Biostatistics 4, 249-264 (2003).
Ito, S. et al. Role of Tet proteins in 5mC to 5hmC conversion, ES-cell self-renewal and inner cell mass specification. Nature 466, 1129-1133 (2010).
Jin, K. et al. Vascular endothelial growth factor (VEGF) stimulates neurogenesis in vitro and in vivo. Proc Natl Acad Sci USA 99, 11946-11950 (2002, Epub Aug. 14, 2002).
Jin, S. G. et al. 5-Hydroxymethylcytosine is strongly depleted in human cancers but its levels do not correlate with IDH1 mutations. Cancer Res 71, 7360-7365 (2011, Epub Nov. 3, 2011).
Kanda M. et al. Clinical significance of expression and epigenetic profiling of TUSC1 in gastric cancer. J Surg Oncol. 2014; 110(2):136-44.
Kim, Y. et al. Platelet-derived growth factor receptors differentially inform intertumoral and intratumoral heterogeneity. Genes Dev 26, 1247-1262 (2012).
Kriaucionis, S. et al. The nuclear DNA base 5-hydroxymethylcytosine is present in Purkinje neurons and the brain. Science 324, 929-930 (2009, Epub Apr. 16, 2009).
Li Y. J et al. Int J Clin Exp Pathol. 2015; 8(10):12410-8. eCollection 2015.
Lian, C. G. et al. Loss of 5-hydroxymethylcytosine is an epigenetic hallmark of melanoma. Cell 150, 1135-1146 (2012).
Liu, H.K. et al. (Apr. 1, 2010). "The nuclear receptor tailless induces long-term neural stem cell expansion and brain tumor initiation," Genes Dev 24(7):683-695.
Liu X. et al. Adaptive amphiphilic dendrimer-based nanoassemblies as robust and versatile siRNA delivery systems Angew Chem Int Ed Engl. (Oct. 27, 2014, Epub Sep. 12, 2014):53(44):11822-7.
Liu X. et al. Promoting siRNA delivery via enhanced cellular uptake using an arginine-decorated amphiphilic dendrimer. Nanoscale. 2015; 7(9):3867-75.
Liu, N et al. Intrinsic and extrinsic connections of Tet3 dioxygenase with CXXC zinc finger modules. PLoS One 8, e62755 (2013).
Liu, X. et al. Targeted delivery of Dicer-substrate siRNAs using a dual targeting peptide decorated dendrimer delivery system. Nanomedicine 10, 1627-1636 (2014).
Liu, X. et al. Structurally flexible triethanolamine-core poly(amidoamine) dendrimers as effective nanovectors to deliver RNAi-based therapeutics. Biotechnol Adv 32, 844-852 (Jul.-Aug. 2014, Epub Aug. 9, 2013).
Liu, X. et al. Dendrimers as non-viral vectors for siRNA delivery. New J Chem 36, 256-263 (2012).
Louis, D. N. et al. The 2007 WHO classification of tumours of the central nervous system. Acta Neuropathol 114, 97-109 (2007, Epub Jul. 6, 2007).
Majumder, P. et al. (Apr. 28, 2014, e-published Feb. 18, 2014). "Inhibiting tumor growth by targeting liposomally encapsulated CDC20siRNA to tumor vasculature: therapeutic RNA interference," *J Control Release* 180:100-108.

Modena, P. et al. (Nov. 20, 2006). "Identification of tumor-specific molecular signatures in intracranial ependymoma and association with clinical characteristics," *J Clin Oncol* 24(33):5223-5233.
Moran-Crusio, K. et al. Tet2 loss leads to increased hematopoietic stem cell self-renewal and myeloid transformation. Cancer Cell 20, 11-24 (2011 Epub Jun. 30, 2011).
Oh, J.E. et al (Oct. 2015). "Alterations in the NF2/LATS1/LATS2/YAP Pathway in Schwannomas," J Neuropathol Exp Neurol. 74(10):952-959.
Orr, B. A. et al. Decreased 5-hydroxymethylcytosine is associated with neural progenitor phenotype in normal brain and shorter survival in malignant glioma. PLoS One 7, e41036 (2012, Epub Jul. 19, 2012).
Park, H.J .et al. (Nov. 2010, Epub Aug. 31, 2010). "The neural stem cell fate determinant TLX promotes tumorigenesis and genesis of cells resembling glioma stem cells," Mol Cells 30(5):403-408.
Perera, A. et al. TET3 is recruited by REST for context-specific hydroxymethylation and induction of gene expression. Cell Rep 11, 283-294 (2015 Epub Apr. 2, 2015).
Phillips, H.S. et al. (Mar. 2006). "Molecular subclasses of high-grade glioma predict prognosis, delineate a pattern of disease progression, and resemble stages in neurogenesis," Cancer Cell 9(3):157-173.
Prochiantz, A. (Feb. 2007). "For protein transduction, chemistry can win over biology," Nat. Methods 4(2):119-120.
Qu, Q. et al. Orphan nuclear receptor TLX activates Wnt/$\beta$-catenin signalling to stimulate neural stem cell proliferation and self-renewal. Nat Cell Biol 12, 31-40; sup pp. 31-39 (2010, Epub Dec. 13, 2009).
Quivoron, C. et al. TET2 inactivation results in pleiotropic hematopoietic abnormalities in mouse and is a recurrent event during human lymphomagenesis. Cancer Cell 20, 25-38 (Jul. 2011, Epub Jun. 30, 2011).
Reya, T. et al. Stem cells, cancer, and cancer stem cells. Nature 414, 105-111 (Nov. 1, 2001).
Shan Z. et al. TUSC1, a putative tumor suppressor gene, reduces tumor cell growth in vitro and tumor growth in vivo. PLoS One. 2013; 8(6):e66114.
Sharma, M.K. et al. (Feb. 1, 2007). "Distinct genetic signatures among pilocytic astrocytomas relate to their brain region origin," Cancer Res 67(3):890-900.
Shi, Y. et al. Expression and function of orphan nuclear receptor TLX in adult neural stem cells. Nature 427, 78-83 (2004).
Shimizu D. et al. Identification of intragenic methylation in the TUSC1 gene as a novel prognostic marker of hepatocellular carcinoma. Oncol Rep. (2014, Epub Dec. 20, 2013) 31(3):1305-13.
Sim, F.J. et al. (Nov. 29, 2006). "Neurocytoma is a tumor of adult neuronal progenitor cells," J Neurosci 26(48):12544-12555.
Singh, S. K. et al. Identification of human brain tumour initiating cells. Nature 432, 396-401 (Nov. 18, 2004).
Song, S. J. et al. MicroRNA-Antagonism Regulates Breast Cancer Stemness and Metastasis via TET-Family-Dependent Chromatin Remodeling. Cell 154, 311-324 (Jul. 2013, Epub Jul. 3, 2013).
Song, S. J. et al. The oncogenic microRNA miR-22 targets the TET2 tumor suppressor to promote hematopoietic stem cell self-renewal and transformation. Cell Stem Cell 13, 87-101 (Jul. 3, 2013).
Sugahara, K. N. et al. Tissue-penetrating delivery of compounds and nanoparticles into tumors. Cancer Cell 16, 510-520 (2009).
Sun, G. et al. Orphan nuclear receptor TLX recruits histone deacetylases to repress transcription and regulate neural stem cell proliferation. PNAS USA 104, 15282-15287 (2007, Epub Sep. 14, 2007).
Tahiliani, M. et al. Conversion of 5-methylcytosine to 5-hydroxymethylcytosine in mammalian DNA by MLL partner TET1. Science 324, 930-935 (2009, Epub Apr. 16, 2009).
Tan, B. T. et al. The cancer stem cell hypothesis: a work in progress. Lab Invest 86, 1203-1207 (2006 Epub Oct. 30, 2006).
Taylor, M.D. et al. (Oct. 2005). "Radial glia cells are candidate stem cells of ependymoma," Cancer Cell 8(4):323-335.
Teesalu, T. et al. C-end rule peptides mediate neuropilin-1-dependent cell, vascular, and tissue penetration. Proc Natl Acad Sci USA 106, 16157-16162 (2009, Epub Sep. 2, 2009).
Tseng, Y. C. et al. Lipid-based systemic delivery of siRNA. Adv Drug Deliv Rev 61, 721-731 (2009, Epub Mar. 26, 2009).

(56) References Cited

OTHER PUBLICATIONS

Verhaak, R. G. et al. Integrated genomic analysis identifies clinically relevant subtypes of glioblastoma characterized by abnormalities in PDGFRA, IDH1, EGFR, and NFL Cancer Cell 17, 98-110 (2010).

Whitehead, K. A., Langer, R., and Anderson, D. G. Knocking down barriers: advances in siRNA delivery. Nat Rev Drug Discov 8, 129-138 (2009).

Wolinsky, J. B. and Grinstaff, M. W. Therapeutic and diagnostic applications of dendrimers for cancer treatment. Adv Drug Deliv Rev 60, 1037-1055 (2008 Epub Mar. 4, 2008).

Xu, W. et al. Oncometabolite 2-hydroxyglutarate is a competitive inhibitor of alpha-ketoglutarate-dependent dioxygenases. Cancer Cell 19, 17-30 (2011).

Xu, Y. et al. Tet3 CXXC domain and dioxygenase activity cooperatively regulate key genes for Xenopus eye and neural development. Cell 151, 1200-1213 (2012).

Yan, K. et al. Glioma cancer stem cells secrete Gremlini to promote their maintenance within the tumor hierarchy. Genes Dev 28, 1085-1100 (May 15, 2014 Epub May 1, 2014).

Yang, H., et al. Tumor development is associated with decrease of TET gene expression and 5-methylcytosine hydroxylation. Oncogene 32, 663-669 (2013).

Yu T et al. An amphiphilic dendrimer for effective delivery of small interfering RNA and gene silencing in vitro and in vivo, (Aug. 20, 2012 Epub Jul. 24, 2012). Angew Chem Int Ed Engl 51(34):8478-84.

Yu, R.T. et al. Relationship between *Drosophila* gap gene tailless and a vertebrate nuclear receptor Tlx Nature 370, 375-379 (1994).

Zhang, Y. et al. (Aug. 6, 2015). "MicroRNA-587 antagonizes 5-FU-induced apoptosis and confers drug resistance by regulating PPP2R1B expression in colorectal cancer," *Cell Death Dis* 2015: 6:e1845.

Zhao, C. et al. microRNA let-7b regulates neural stem cell proliferation and differentiation by targeting nuclear receptor TLX signaling. PNAS USA 107, 1876-1881 (Feb. 2010, Epub Jan. 19, 2010.).

Zhu, Z. et al. (Aug. 7, 2014, e-published May 15, 2014). "Targeting self-renewal in high-grade brain tumors leads to loss of brain tumor stem cells and prolonged survival," Cell Stem Cell 15(2):185-198.

Zhou, J. et al. Biodegradable poly(amine-co-ester) terpolymers for targeted gene delivery. Nat Mater 11, 82-90 (2012).

Zhou, J. et al. "Systemic administration of combinatorial dsiRNAs via nanoparticles efficiently suppresses HIV-1 infection in humanized mice," Mol Ther. Dec. 2011;19(12):2228-38. Epub Sep. 27, 2011.

Zhou, J. et al. "PAMAM dendrimers for efficient siRNA delivery and potent gene silencing," Chem Commun (Camb). Jun. 14, 2006;(22):2362-4. Epub May 10, 2006.

Zou, Y. et al. (Dec. 2012, Epub Oct. 1, 2012). "The nuclear receptor TLX is required for gliomagenesis within the adult neurogenic niche," Mol Cell Biol 32(23):4811-4820.

International Search Report dated Apr. 7, 2017, for PCT Application No. PCT/US2017/013505, filed Jan. 13, 2017, 4 pages.

Written Opinion dated Apr. 7, 2017, for PCT Application No. PCT/US2017/013505, filed Jan. 13, 2017, 8 pages.

* cited by examiner

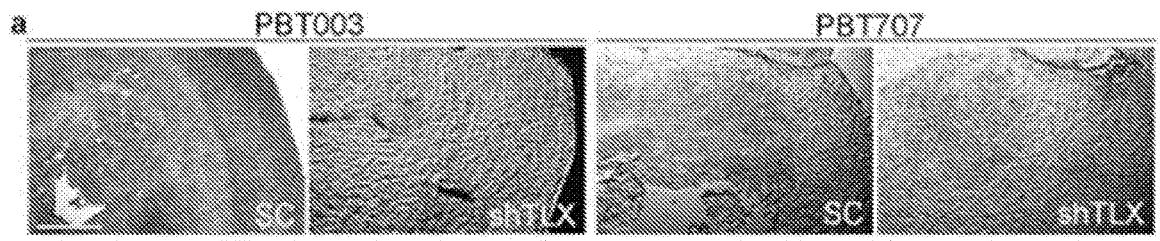
FIG. 3A
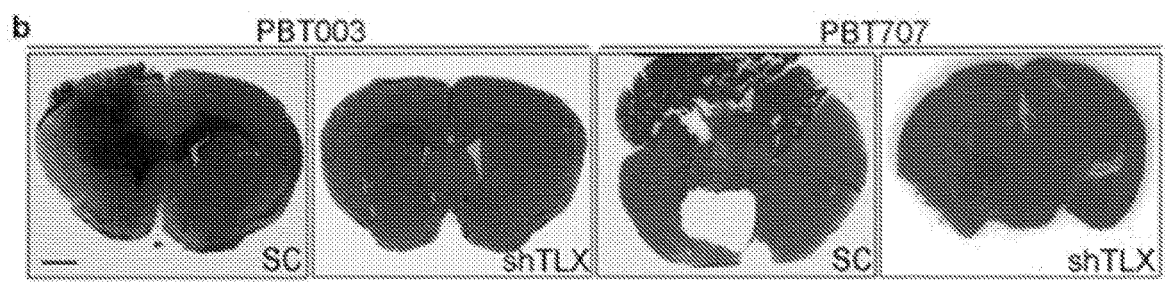
FIG. 3B
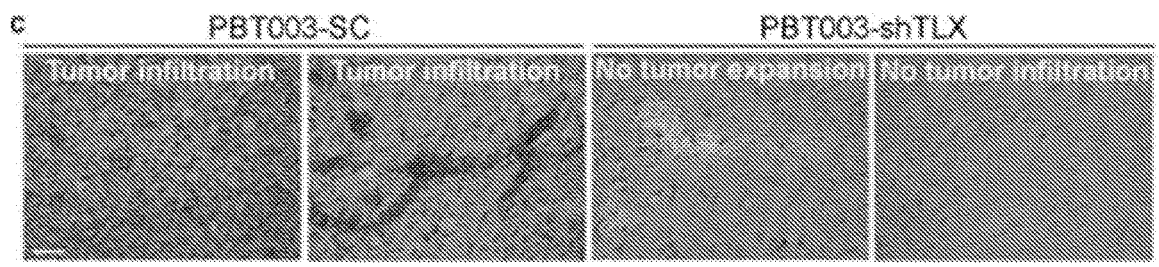
FIG. 3C
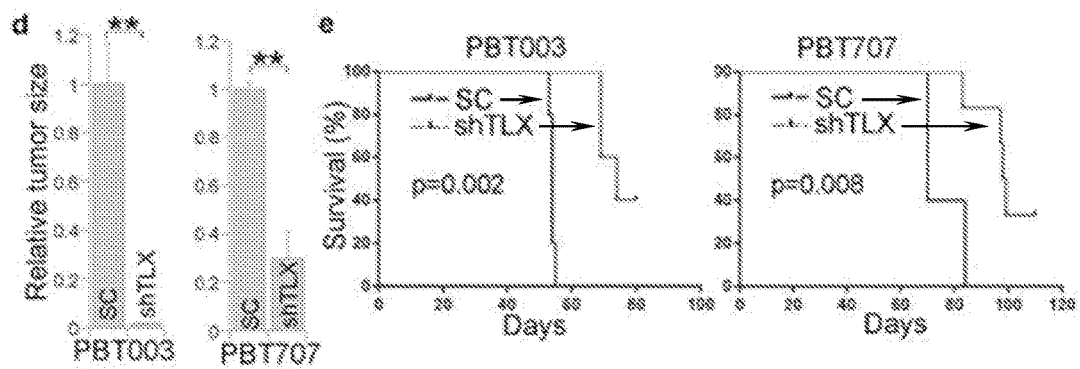
FIG. 3D
FIG. 3E

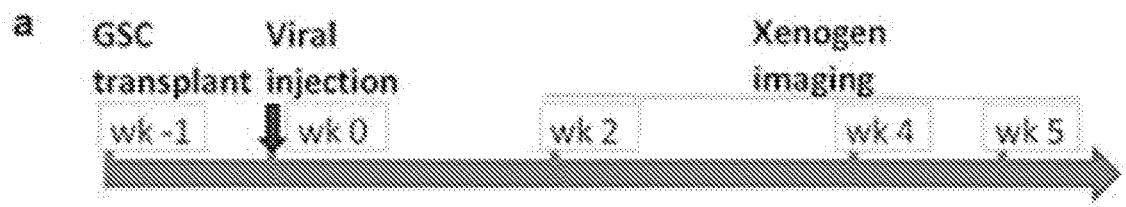
FIG. 4A
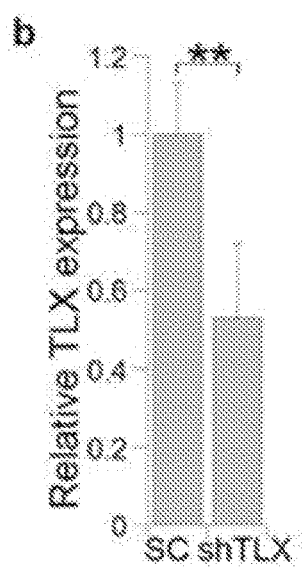
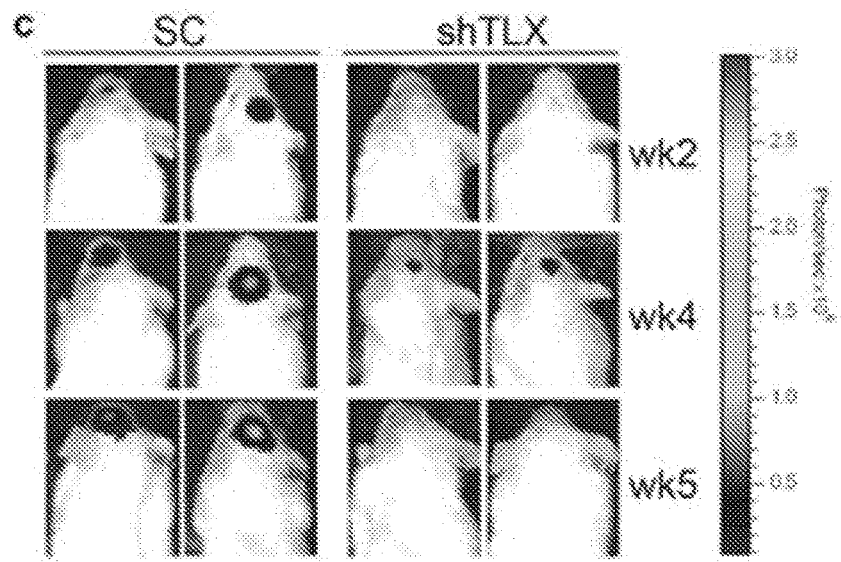
FIG. 4B
FIG. 4C

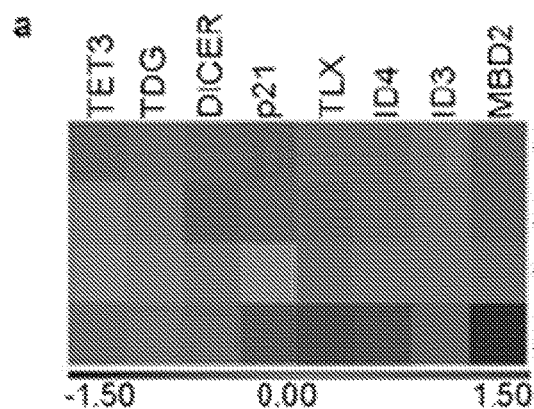
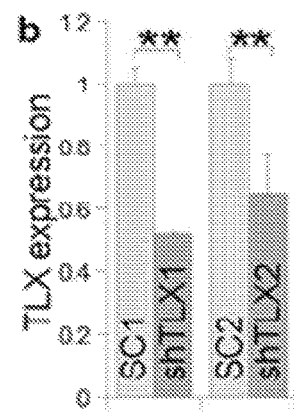
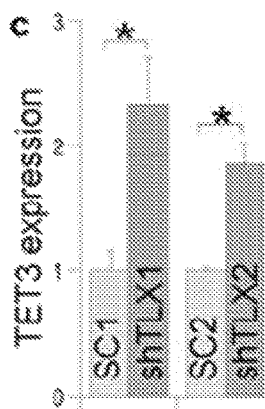
FIG. 7A FIG. 7B FIG. 7C
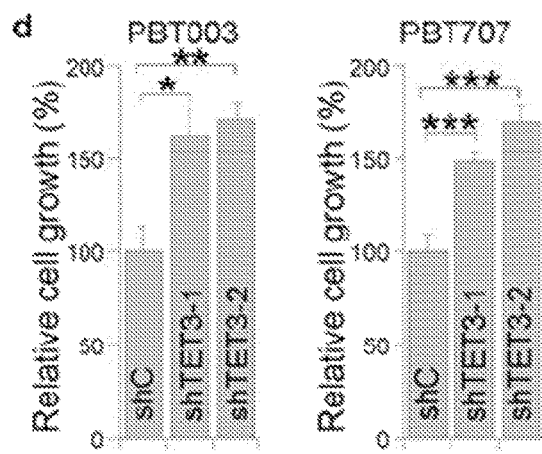
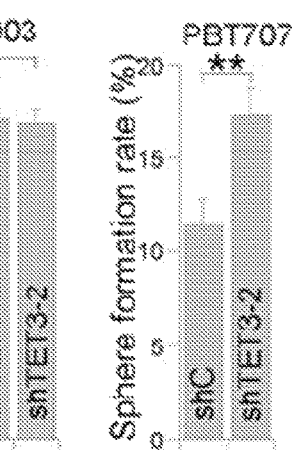
FIG. 7D FIG. 7E
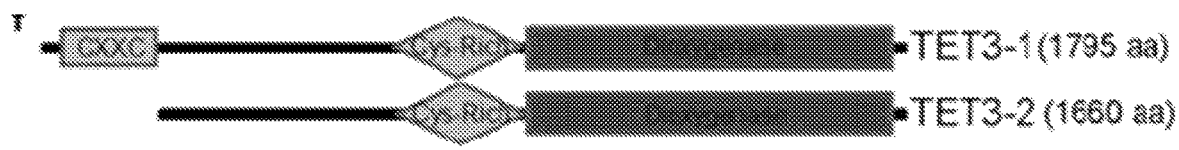
FIG. 7F FIG. 10A
FIG. 10B
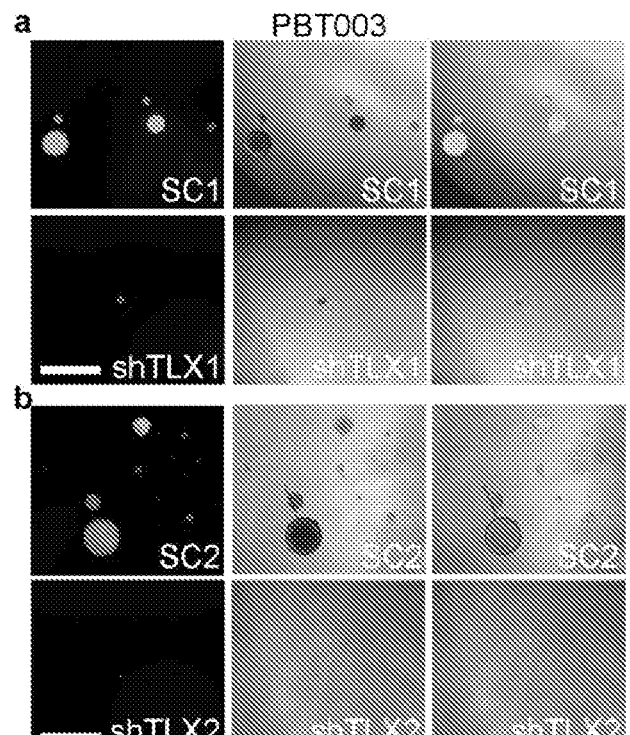
FIG. 10C
FIG. 10D
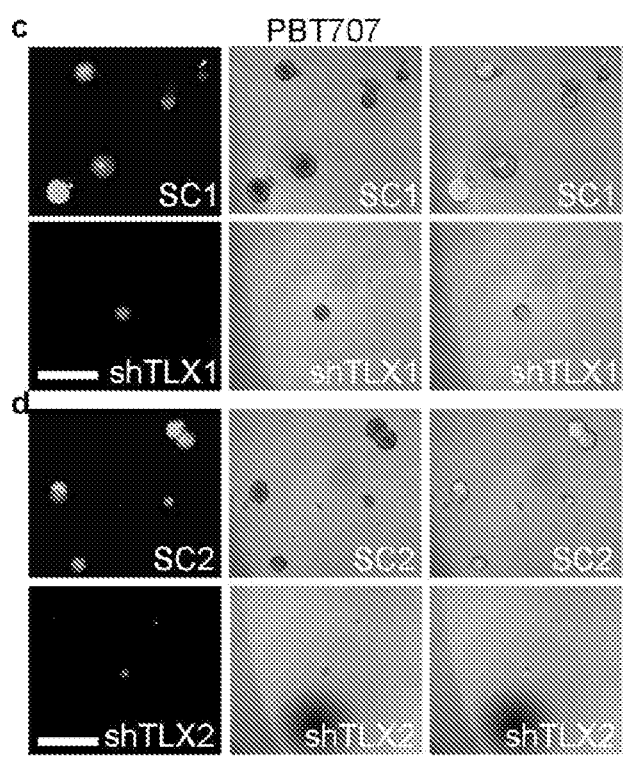

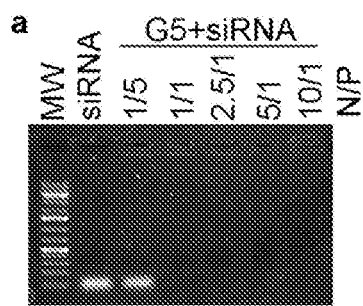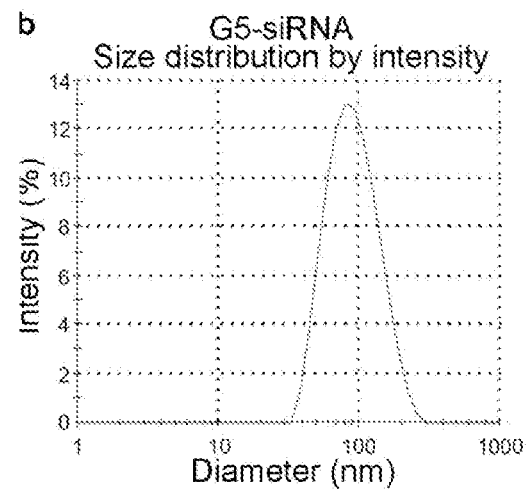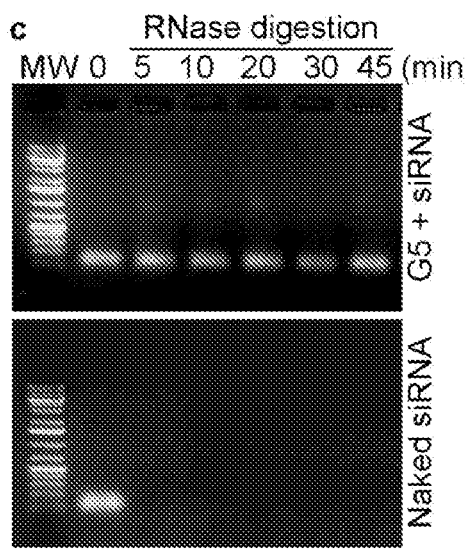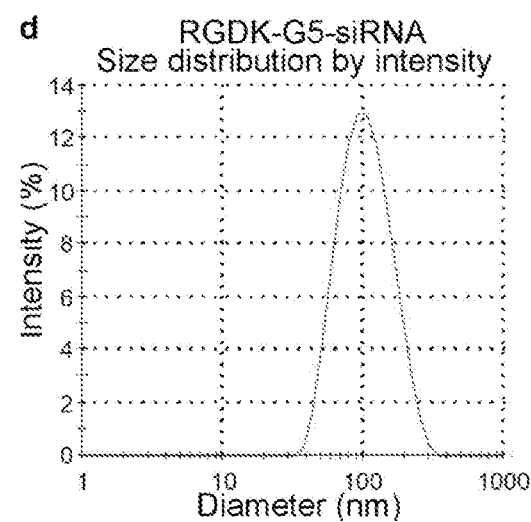
FIG. 13A
FIG. 13B
FIG. 13C
FIG. 13D

TARGETING GLIOBLASTOMA STEM CELLS THROUGH THE TLX-TET3 AXIS

CROSS REFERENCE TO RELATED APPLICATIONS

This application is a National Stage Application, filed under 35 U.S.C. § 371, of International Application No. PCT/US2017/013505, filed Jan. 13, 2017, which claims the benefit of U.S. Provisional Application No. 62/279,588, filed Jan. 15, 2016, the entire contents of each of which are incorporated herein in their entireties and for all purposes.

INCORPORATION-BY-REFERENCE OF SEQUENCE LISTING

The contents of the text file named "48440-602001WO_SL.TXT", which is filed herewith, was created on Jan. 13, 2017, and is 11,098 bytes is size, is hereby incorporated by reference in its entirety.

BACKGROUND

Glioblastoma is the most common and aggressive primary brain tumor with median survival time of 14 months after diagnosis[1]. No effective treatment has been developed for glioblastoma patients yet. Recent studies have led to the hypothesis that glioblastomas are maintained by a small population of cancer stem cells that retain stem cell properties, are highly tumorigenic and resistant to radiotherapy and chemotherapy[2-4]. The cancer stem cell hypothesis proposes that a tumor comprises a cellular hierarchy, in which cancer stem cells reside at the top and have the ability to give rise to the heterogeneous populations of the tumor bulk[5-7]. The presence of these cancer stem cells together with the heterogeneity of the tumor mass renders glioblastoma treatment-resistant and recurring[8]. Therefore new therapies are needed to target these cancer stem cells[4,9].

TLX (NR2E1) is a nuclear receptor expressed in vertebrate forebrains[10] and essential for neural stem cell self-renewal[11,12]. Recently, TLX has been shown to be expressed in human glioblastoma tissues and cell lines[13,14], and play a role in glioblastoma development in mouse tumor models[14]. However, the function of TLX in human glioblastoma stem cells (GSCs)—initiated tumorigenesis and the effect of modulating TLX expression in human GSCs on the development of glioblastoma remain to be determined.

5-hydroxymethylcytosine (5hmC) is a form of DNA modification derived from hydroxylation of 5-methylcytosine (5mC). The level of 5hmC is considerably reduced in many types of human cancers[15-17], including gliomas[18-20]. The level of 5hmC is tightly controlled by the TET family of dioxygenases, which catalyze the conversion of 5mC to 5hmC[21,22]. TET proteins have been shown to inhibit hematopoietic transformation[23-25], breast and prostate cancer invasion and metastasis[26]. However the role of TET proteins, especially TET3, in glioblastoma tumorigenesis remains largely unknown.

Glioblastomas have been proposed to be maintained by highly tumorigenic GSCs that are resistant to current therapy. Therefore targeting GSCs is critical for developing effective therapies for glioblastoma. Novel insights described herein indicate the role of TET3 in TLX signalling. Compositions and methods of the present invention target the TLX-TET3 pathway to provide a novel therapy for brain cancers including glioblastoma.

SUMMARY

The disclosure or invention provided herewith generally relates to methods and compositions treating an individual suspected of or diagnosed with brain cancer. The methods and compositions, at least in some aspects, are capable of modulating TLX (NR2E1) activity, a nuclear receptor essential for neural stem cell self-renewal, e.g., by downregulating TLX expression, and/or modulating its downstream component(s) such as TET3, thereby providing a novel therapy for brain cancer including, but not limited to, glioblastoma.

In a first aspect, provided herein is a method of treating an individual suspected of or diagnosed with brain cancer by administering a composition that modulates TLX expression or activity. In another aspect, the brain cancer is selected from the group consisting of glioblastoma, oligodendroglioma, dysembryoplastic neuroepithelial tumor, mesenchymal gliomas, pilocytic astrocytomas, neurocytoma, and ependymoma.

In another aspect, the composition that modulates TLX expression and/or activity acts at a DNA level, an RNA level, or at a translational level. In another aspect, the composition that modulates TLX expression and/or activity comprises an shRNA suitable to induce degradation of TLX. In another aspect, the shRNA comprises one or more of SEQ ID NO: 1 or SEQ ID NO: 3. In another aspect, the composition that modulates TLX expression and/or activity comprises an siRNA suitable to induce degradation of TLX. In another aspect, the siRNA comprises one or more of SEQ ID NO: 51-54. In another aspect, the composition that modulates TLX expression and/or activity is complexed with a nanoparticle. In another aspect, the nanoparticle comprises a dendrimer. In another aspect, the dendrimer is a poly(amidoamine) (PAMAM) dendrimer.

In another aspect, the composition upregulates expression of TET3.

In another aspect, the composition that modulates TLX activity comprises a small molecule that binds to a TLX ligand binding site. In another aspect, the small molecule comprises all-trans retinoic acid (ATRA).

In another aspect, provided herein is a method of downregulating TLX expression by administering an agent to target TLX for degradation to a subject in need thereof. In another aspect, the agent comprises an siRNA suitable to induce degradation of TLX. In another aspect, the siRNA comprises one or more of SEQ ID NO: 51-54. In another aspect, the agent is complexed with a nanoparticle. In another aspect, the nanoparticle comprises a dendrimer. In another aspect, the dendrimer is a poly(amidoamine) (PAMAM) dendrimer.

In another aspect, the subject in need thereof is an individual diagnosed with brain cancer. In another aspect, the brain cancer is selected from the group consisting of glioblastoma, oligodendroglioma, dysembryoplastic neuroepithelial tumor, mesenchymal gliomas, pilocytic astrocytomas, neurocytoma, and ependymoma.

In another aspect, provided herein is a composition for the treatment of brain cancer comprising an siRNA targeting TLX complexed with a dendrimer. In another aspect, the brain cancer is selected from the group consisting of glioblastoma, oligodendroglioma, dysembryoplastic neuroepithelial tumor, mesenchymal gliomas, pilocytic astrocytomas, neurocytoma, and ependymoma.

In another aspect, the siRNA comprises one or more of SEQ ID NO: 51-54. In another aspect, the dendrimer is a poly(amidoamine) (PAMAM) dendrimer. In another aspect, the PAMAM dendrimer comprises a peptide coating. In another aspect, the peptide coating comprises RGDK.

In another aspect, provided herein is a pharmaceutical formulation comprising the composition for the treatment of brain cancer comprising an siRNA targeting TLX complexed with a dendrimer and a pharmaceutically acceptable excipient.

In another aspect, provided herein is a method of treating an individual suspected of, having, or diagnosed with brain cancer by administering a composition that modulates TET3. In another aspect, the brain cancer is selected from the group consisting of glioblastoma, oligodendroglioma, dysembryoplastic neuroepithelial tumor, mesenchymal gliomas, pilocytic astrocytomas, neurocytoma, and ependymoma. In another aspect, the composition that modulates TET3 acts at a DNA level, an RNA level, or at a translational level. In another aspect, the composition comprises a small molecule.

BRIEF DESCRIPTION OF THE DRAWINGS

FIG. 1A is a series of graphs showing RT-PCR analysis of TLX expression in GSCs transduced with TLX shRNAs. Scrambled RNAs (SC1 and SC2) were included as negative controls. N=3, *p<0.05, p<0.01, *p<0.001 by Student's t-test. Error bars are s.d. of the mean. FIG. 1B is a series of graphs showing growth kinetic analysis of the GSC lines transduced with scrambled control RNAs (SC1, SC2) or TLX shRNAs (shTLX1, shTLX2). N=4. Error bars are s.d. of the mean.

FIG. 2A is a series of graphs showing quantification of sphere formation rate of GSCs transduced with scrambled control RNAs (SC1, SC2) or TLX shRNAs (shTLX1, shTLX2). N=6, p<0.01, *p<0.001 by Student's t-test. Error bars are s.d. of the mean. FIG. 2B is a series of graphs of limiting dilution assay (LDA) analysis of GSCs transduced with scrambled control RNAs (SC) or TLX shRNAs (shTLX). N=20.

FIG. 3A-3E demonstrate that knocking down TLX expression dramatically reduced the tumor growth and prolonged the survival of mice transplanted with GSCs. FIG. 3A is a series of images showing GFP fluorescence of PBT003 cells or PBT707 cells transduced with scrambled control RNAs (SC) or TLX shRNAs (shTLX) and a GFP reporter. Merged images of GFP fluorescence and phase contrast images are shown. FIG. 3B is a series of images showing H&E staining of brain tumor tissues derived from transplanted PBT003 cells and PBT707 cells, transduced with scrambled control RNA (SC), or TLX shRNA (shTLX). FIG. 3C is a series of images showing H&E staining showing typical tumor infiltration characteristics of glioblastoma. FIG. 3D is a graph showing relative sizes (volumes) of brain tumors derived from PBT003 or PBT707 cells that were transduced with scrambled control RNA (SC) or TLX shRNA (shTLX). FIG. 3E is a set of survival curves of NSG mice transplanted with PBT003 or PBT707 cells transduced with scrambled control RNA (SC) or TLX shRNA (shTLX). X axis represents days after GSC transplantation. For FIG. 3A-3D, N=4, **p<0.01 by Student's t-test. Error bars are s.d. of the mean. For FIG. 3E, N=5, log-rank test. Scale bar: 200 μm for FIG. 3A; 1 mm for FIG. 3B; 50 μm for FIG. 3C.

FIG. 4A-4H demonstrate that viral delivery of TLX shRNA inhibited GSC-initiated tumor formation in vivo in a xenograft mouse model. FIG. 4A is a schematic of the experimental design, including GSC transplantation, viral treatment and xenogen imaging of xenografted tumors. FIG. 4B is a graph of RT-PCR analysis showing TLX knockdown in vivo. N=3, p<0.01 by Student's t-test. Error bars are s.e. of the mean. FIG. 4C is a series of xenogen images of brain tumors in NSG mice treated with virus expressing scrambled control (SC) or TLX shRNA (shTLX). The scale for bioluminescence intensity is shown on the right. FIG. 4D is a graph showing quantification of the bioluminescence intensity of tumors treated with scrambled control (SC) or TLX shRNA (shTLX) in the brains of engrafted NSG mice. N=6, p<0.01 by Student's t-test. Error bars are s.e. of the mean. FIG. 4E is a graph of survival curves of PBT003-engrafted NSG mice treated with virus expressing either scrambled control (SC) or TLX shRNA (shTLX). X axis represents days after viral injection. N=10 for each treatment group. p<0.05 by log-rank test. FIG. 4F is a set of images showing H&E staining of brain tumor tissues derived from transplanted PBT003 cells in NSG mice treated with scrambled control (SC) or TLX shRNA (shTLX). Scale bar: 1 mm. FIG. 4G is a set of xenogen images of NSG mice survived over 200 days after treatment with virus expressing TLX shRNA (shTLX). FIG. 4H is an image of H&E staining showing typical tumor infiltration characteristics of glioblastoma. Scale bar: 50 μm.

FIG. 5A is a series of images showing cellular uptake of Cy3-siRNA delivered by siRNA alone or G5 dendrimers (at N/P ratio of 5) to PBT003 cells. Scale bar: 200 μm. Assays were repeated three times. FIG. 5B is a set of graphs showing cellular uptake of Cy3-siRNA analyzed by flow cytometry. Uptake of Cy3-siRNA delivered by G5 dendrimer complexes into PBT003 cells was 98.4%. FIG. 5C is a series of images showing that expression of integrin αv and neuropilin-1 on PBT003 GSCs revealed by immunostaining. Scale bar: 100 μm. FIG. 5D is a series of images showing that cellular uptake of Cy3-labeled siRNA delivered by siRNA alone, G5 dendrimers, or RGDK-coated G5 dendrimers (at N/P ratio of 5) to PBT003 cells. Scale bar: 200 μm. Assays were repeated three times. FIG. 5E is a graph showing knockdown of TLX expression in PBT003 cells by the G5 dendrimer-TLX siRNA complex (G5-siTLX) and RGDK-coated G5-siTLX, analyzed by RT-PCR. G5 dendrimer-scrambled control RNA (G5-SC) and RGDK-coated G5-SC nanoparticles were included as controls. FIG. 5F is a graph showing the growth inhibitory effect of the G5-siTLX and RGDK-G5-siTLX. PBT003 cells treated with G5 dendrimers or RGDK-coated G5 dendrimers complexes with SC or siTLX (at the N/P ratio of 5) were analyzed by CellTiter-Glo luminescent assay. N=3 for FIG. 5E; N=6 for FIG. 5F. For both FIGS. 5E and 5F, *p<0.05, p<0.01, *p<0.001 by Student's t-test. Error bars are s.d. of the mean.

FIG. 6A is a schematic of the experimental design, including GSC transplantation, dendrimer-siTLX complex treatment and xenogen imaging of xenografted tumors. The mice were treated with RGDK coated G5 dendrimer-siTLX complex or RGDK coated G5 dendrimer-SC complex. FIG. 6B is a graph showing in vivo knockdown of TLX using RGDK-GS-siTLX nanocomplex. N=3, ***p<0.001 by Student's t-test. Error bars are s.e. of the mean. FIG. 6C is a series of xenogen images of brain tumors in NSG mice treated with scrambled control (SC) or TLX siRNA (siTLX). The scale for bioluminescence intensity is shown on the right. FIG. 6D is a graph showing quantification of the bioluminescence intensity of tumors treated with scrambled control (SC) or TLX siRNA (siTLX) in the brains of engrafted NSG mice. N=7, *p<0.05, **p<0.01 by Student's t-test. Error bars are s.e. of the mean. FIG. 6E is a graph of survival curves of PBT003-engrafted NSG mice treated with scrambled control (SC) or TLX siRNA (siTLX). X axis represents days after dendrimer-siRNA treatment. N=7 for each treatment group. p<0.01 by log-rank test. FIG. 6F and FIG. 6G are images of H&E staining showing typical tumor infiltration characteristics of glioblastoma. Scale bar: 1 mm (FIG. 6F) and 50 µm (FIG. 6G).

FIG. 7A-7K demonstrate that TET3 regulates GSC growth, self-renewal and tumorigenesis. FIG. 7A is an image of microarray analysis of PBT003 cells transduced with virus expressing scrambled control (SC) or TLX shRNA (shTLX). FIG. 7B and FIG. 7C are graphs of RT-PCR analysis showing TET3 up-regulation upon TLX knockdown. N=3, *p<0.05, **p<0.01 by Student's t-test. Error bars are s.d. of the mean. FIGS. 7D and 7E are graphs showing cell growth (FIG. 7D) and sphere formation (FIG. 7E) analyses of the GSC lines transduced with control RNA (shC) or TET3 shRNAs (shTET3-1, shTET3-2). FIG. 7F shows schematics of TET3-1 and TET3-2 proteins with characteristic domains. FIG. 7G and FIG. 7H are graphs showing cell growth (FIG. 7G) and sphere formation (FIG. 7H) analyses of GSCs transduced with control (C) or TET3-expressing lentivirus, TET3-1 or TET3-2. FIG. 7I is an image of RT-PCR analysis showing overexpression of TET3 in GSCs. FIG. 7J is a graph of relative sizes (volumes) of brain tumors derived from PBT003 cells that were transduced with control RNA (shC) or TET3 shRNA (shTET3). FIG. 7K is a set of survival curves of NSG mice transplanted with PBT003 cells transduced with control RNA (shC) or TET3 shRNA (shTET3). X axis represents days after GSC transplantation. For FIG. 7D and FIG. 7G, N=4; For FIG. 7E and FIG. 7H, N=6. Error bars are s.e. of the mean. *p<0.05, p<0.01, *p<0.001 by Student's t-test. For FIG. 7J, N=3, ***p<0.001 by Student's t-test. Error bars are s.d. of the mean. For FIG. 7K, N=8, p<0.001 by log-rank test.

FIG. 8A-FIG. 8C are graphs of RT-PCR analysis of dox-induced knockdown of TLX (FIG. 8A) and TET3 (FIGS. 8B and 8C) in PBT003 and PBT707 cells transduced with lentivirus expressing dox-inducible TLX shRNA (shTLX) and or with dox-inducible TET3 shRNA (shTET3 or shTET3+shTLX). N=3, error bars are s.d. of the mean. *p<0.05, p<0.01, *p<0.001 by Student's t-test for all the quantifications in this figure. FIGS. 8D and 8E are graphs showing cell growth (FIG. 8D) and sphere formation (FIG. 8E) analyses of PBT003 and PBT707 cells transduced with lentivirus expressing dox-inducible shTLX alone or together with dox-inducible shTET3. N=4 for FIG. 8D and N=6 for FIG. 8E, error bars are s.e. of the mean. FIG. 8F is an image of a heatmap of differentially expressed genes in PBT003 cells transduced with virus expressing TLX shRNAs (shTLX1, shTLX2) or TET3 shRNAs (shTET3-1, shTET3-2), in microarray analysis. FIG. 8G is an image of a heatmap of six differentially expressed genes in PBT003 cells transduced with virus expressing TLX shRNAs (shTLX1, shTLX2) or TET3 shRNAs (shTET3-1, shTET3-2), in microarray analysis. FIGS. 8H and 8I show an image and graph of 5hmC dot blot analysis of total 5hmC level in TLX knockdown or TET3 knockdown PBT003 cells. FIGS. 8J and 8K are graphs showing hydroxymethylated DNA immunoprecipitation (hMeDIP)-qPCR analysis of BTG2 and PPP2R1B (PPP2R) promoter in PBT003 cells transduced with virus expressing shTLX or shTET3. N=4, error bars are s.d. of the mean.

FIG. 9A is an image showing immunostaining of primary GSC spheres from GSC lines. Nestin (neural progenitor marker, red), TLX (green). Merged images of nestin, TLX and DAPI staining (blue) are shown on the right. Scale bar: 20 µm. FIG. 9B is an image showing multipotency of the GSCs. When induced to differentiate, the GSCs gave rise to both Tuj1-positive neurons (red) and GFAP-positive astrocytes (green). A merged image of Tuj1, GFAP, and DAPI staining (blue) is shown on the right. Scale bar: 25 µm. FIG. 9C is an image showing tumor formation by GSCs. When transplanted into the brains of immunodeficient NSG mice, GSC lines (PBT003, PBT707) formed brain tumors with typical infiltrative characteristics of glioblastoma, as revealed by H&E staining. Scale bar: 1 mm (left); 50 µm (right).

FIG. 10A-10D demonstrate knockdown of TLX reduces GSC self-renewal. FIGS. 10A and 10B are images showing clonal analysis of PBT003 cells transduced with a GFP reporter and scrambled control RNAs (SC1, SC2) or TLX shRNAs (shTLX1, shTLX2). GFP fluorescence images are shown on the left, phase contrast images are shown in the center, and merged images are shown on the right. FIGS. 10C and 10D are images showing clonal analysis of PBT707 cells transduced with a GFP reporter and scrambled control RNAs (SC1, SC2) or TLX shRNAs (shTLX1, shTLX2). Assays were repeated three times. Scale bar: 200 µm.

FIG. 12A is a schematic of the experimental design, including GSC transplantation, viral treatment and xenogen imaging of xenografted tumors. FIG. 12B is a series of xenogen images of brain tumors in NSG mice treated with virus expressing scrambled control (SC) or TLX shRNA (shTLX). The scale for bioluminescence intensity is shown on the right. FIG. 12C is a graph of quantification of the bioluminescence intensity of tumors treated with scrambled control (SC) or TLX shRNA (shTLX) in the brains of engrafted NSG mice. N=3, error bars are s.e. of the mean. *p<0.05 by Student's t-test.

FIG. 13A-13D illustrate characterization of the TLX siRNA nanocomplex. FIG. 13A is an image showing the binding ability of G5 with TLX siRNA at N/P ratios ranging from 1 to 10 tested using agarose gel electrophoresis. Naked TLX siRNA was used as a control. FIG. 13B is a graph of size distribution of the G5-TLX siRNA complexes at N/P ratio of 5 measured by dynamic light scattering (DLS). FIG. 13C is an image of RNase digestion assay. Naked TLX siRNA and the G5-TLX siRNA complexes at N/P ratio of 5 were incubated with 0.01 µg per µl RNase A at 37° C. for 0-45 min, followed by agarose gel electrophoresis analysis. FIG. 13D is a graph of size distribution of the RGDK-G5-TLX siRNA nanoparticles at N/P ratio of 5 determined by DLS.

FIGS. 15A and 15B are graphs of RT-PCR showing TET3 up-regulation upon TLX knockdown (FIG. 15A) and TET3 down-regulation upon TET3 knockdown (FIG. 15B) in GSCs. SC is the control RNA for shTLX, and shC is the control RNA for shTET3-1 and shTET3-2. N=3, *p<0.05, p<0.01, *p<0.001 by Student's t-test, error bars are s.d. of the mean. FIGS. 15C and 15D are images of full gels for images in FIG. 7I.

FIG. 17A is a schematic of TET3 promoter and proximal intron regions. The location of primers used for mapping TLX binding and histone modifications on TET3 is indicated with (a). The lines indicated with (b) represent exons, while the unlabeled lines represent regions outside of exons. P1 to P7: position 1 to position 7. FIG. 17B is a set of graphs quantifying ChIP assays showing TLX binding to TET3 promoter and proximal introns in PBT003 and PBT707 cells. FIG. 17C is a set of graphs quantifying ChIP assays showing H3K4me3 and H3K9me3 histone modifications on TET3 promoter and proximal introns in PBT003 and PBT707 cells. N=4, error bars are s.d. of the mean.

FIGS. 18A and 18B are graphs showing RT-PCR analysis confirming altered expression of six tumor suppressor genes after TLX (FIG. 18A) or TET3 (FIG. 18B) knockdown in PBT003 cells. N=3, error bars are s.d. of the mean. *p<0.05, p<0.01, *p<0.001 by Student's t-test.

FIG. 19A is a graph showing that ATRA activates TLX. Neurons were transfected with a Gal4-responsive luciferase reporter and the fusion protein of the Gal4 DNA binding domain and the TLX full length (FL) protein (G4-TLX FL). The transfected cells were treated with vehicle control (DMSO) or ATRA, and luciferase activity was measured. The fold induction was quantified by dividing the luciferase activity in cells treated with ATRA by that in cells treated with DMSO. FIG. 19B is a graph showing ATRA binds to the TLX LBD. The binding of ATRA to the wild type (WT) or mutant (MT) TLX LBD was measured by mass spectrometry. FIG. 19C is a graph showing that treatment of PBT003 GSCs with ATRA reduced GSC self-renewal capacity as revealed by sphere formation assay. Error bars are s.d. of the mean. p<0.01, *p<0.001 by Student's t-test.

DETAILED DESCRIPTION OF INVENTION

Figure 1A:
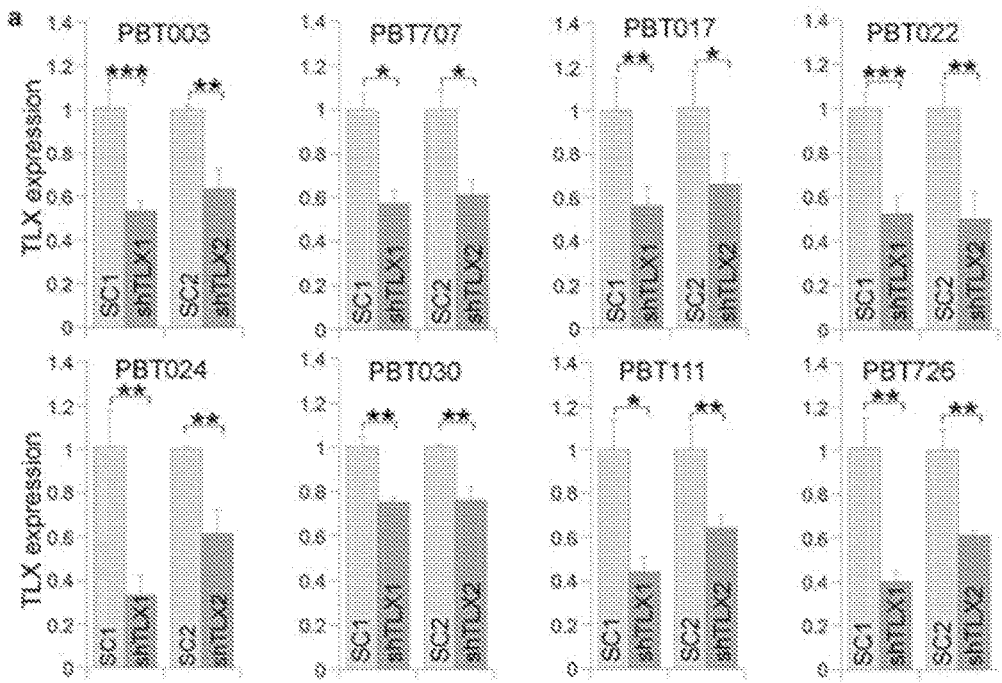
FIGS. 1A and 1B demonstrate that knocking down TLX expression dramatically reduced the growth of GSCs.

The disclosure or invention herewith provides, inter alia, methods and compositions capable of modulating TLX (NR2E1) expression and/or activity, e.g., by downregulating TLX expression, and/or modulating TET3. The compositions provided herein are useful for treating and preventing the progression of brain cancer, e.g., glioblastoma multiforme. Further described herein are pathways by which TLX, a nuclear receptor essential for neural stem cell self-renewal, can be targeted and modulated in the treatment of brain cancers.

Modulation of TLX expression and/or activity by method and composition described herein is useful in the treatment of brain cancer. Compositions for the modulation of TLX expression and/or activity include those that alter TLX expression at the DNA, RNA and translation levels. Any agent (e.g. siRNA, shRNA, small molecule, antibody, or gene editing) capable of modulating TLX expression and/or activity (e.g. downregulating TLX expression or affecting TLX function) can be utilized in the methods of the present disclosure or invention. Without being bound by theory, ribonucleic acid targeted degradation of TLX can inhibit the growth and self-renewal of brain cancer stem cells, and/or can upregulate TLX pathway protein TET3, which can have tumor suppressive effects and/or enhancing survival of animals. In addition, downregulation of TLX activity and/or expression suppresses the progression of established tumors and increased the lifespan of animals, thereby being an effective target to suppress cancer cell self-renewal and tumorigenesis.

Cancer stem cells are critical for tumor maintenance, metastasis, and resistance to therapy. Therefore, targeting cancer stem cells is a priority in the development of novel cancer therapies that can completely cure and eradicate cancer by eliminating residual tumor-initiating cells, or can prevent progression of the cancer. By way of example, glioblastoma stem cells (GSCs) are implicated in the initiation and development of glioblastoma, the most aggressive and invariably lethal brain tumor. Data described herein identifies nuclear receptor TLX and TET3 regulatory axis as a target for GSCs. TLX is fundamental for maintaining GSC growth, self-renewal, and in vivo tumor formation capacity, whereas TET3 is a potential tumor suppressor that inhibits GSC growth and self-renewal. Knockdown of TLX expression using either virally-expressed shRNA or nanoparticle-delivered siRNA, or by other known means, may reduce the growth and self-renewal of GSC and impair the ability of GSCs to form brain tumors in vivo, resulting in suppression of tumor formation. TLX is a promising therapeutic target for brain cancer therapy (e.g. for anti-glioblastoma therapy).

TET3 is a potential tumor suppressor that acts downstream of TLX to regulate GSC growth and self-renewal. TLX represents the first transcription factor that has been identified to regulate TET3 expression. TET3 is a member of the TET family proteins that are known to be epigenetic regulators that control DNA demethylation. Although growing evidence showing that epigenetic regulation plays an important role in cancer development, knowledge on the role of TET family members, especially TET3, in tumor development is rather limited. As described herein, TET3 can suppress the growth and self-renewal of GSCs downstream of TLX. Also, as illustrated herein, downregulation of TET3, e.g. via treatment of its shRNA significantly shorten survival compared to control animals not having TET3-shRNA. Together, the present disclosure or invention shows that knockdown of TET3 increases tumor progression and decreases the lifespan of animals, especially affected with cancer, in a manner opposite to knockdown of TLX. In view of this disclosure, modulation of TET3 activity provides a novel tool in preventing and/or treating tumor or cancer in animals.

Definitions

While various embodiments and aspects of the present disclosure or invention are shown and described herein, it will be obvious to those skilled in the art that such embodiments and aspects are provided by way of example only. Numerous variations, changes, and substitutions will now occur to those skilled in the art without departing from the disclosure or invention. It should be understood that various alternatives to the embodiments of the disclosure or invention described herein may be employed in practicing the disclosure or invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this disclosure or invention. The following definitions are provided to facilitate understanding of certain terms used frequently herein and are not meant to limit the scope of the present disclosure.

"Nucleic acid" refers to deoxyribonucleotides or ribonucleotides and polymers thereof in either single- or double-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, and 2-O-methyl ribonucleotides.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The terms "transfection", "transduction", "transfecting" or "transducing" can be used interchangeably and are defined as a process of introducing a nucleic acid molecule or a protein to a cell. Nucleic acids are introduced to a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) *Gene Therapy* 8:1-4 and Prochiantz (2007) *Nat. Methods* 4:119-20.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual*, 18.1-18.88.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell. Expression of a transfected gene can further be accomplished by transposon-mediated insertion into to the host genome. During transposon-mediated insertion, the gene is positioned in a predictable manner between two transposon linker sequences that allow insertion into the host genome as well as subsequent excision. Stable expression of a transfected gene can further be accomplished by infecting a cell with a lentiviral vector, which after infection forms part of (integrates into) the cellular genome thereby resulting in stable expression of the gene.

The term "plasmid" refers to a nucleic acid molecule that encodes for genes and/or regulatory elements necessary for the expression of genes. Expression of a gene from a plasmid can occur in cis or in trans. If a gene is expressed in cis, the gene and the regulatory elements are encoded by the same plasmid. Expression in trans refers to the instance where the gene and the regulatory elements are encoded by separate plasmids.

The term "promoter" or "regulatory element" refers to a region or sequence determinants located upstream or downstream from the start of transcription and which are involved in recognition and binding of RNA polymerase and other proteins to initiate transcription. Promoters need not be of viral origin, for example, mammalian cellular promoters, may be used in the present disclosure or invention.

A "siRNA", "small interfering RNA", "small RNA", or "RNAi" as provided herein refers to a nucleic acid that forms a double stranded RNA, which double stranded RNA has the ability to reduce or inhibit expression of a gene or target gene when expressed in the same cell as the gene or target gene. The complementary portions of the nucleic acid that hybridize to form the double stranded molecule typically have substantial or complete identity. In one embodiment, a siRNA or RNAi refers to a nucleic acid that has substantial or complete identity to a target gene and forms a double stranded siRNA. In embodiments, the siRNA inhibits gene expression by interacting with a complementary cellular mRNA thereby interfering with the expression of the complementary mRNA. Typically, the nucleic acid is at least about 15-50 nucleotides in length (e.g., each complementary sequence of the double stranded siRNA is 15-50 nucleotides in length, and the double stranded siRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length. Non-limiting examples of siRNAs include ribozymes, RNA decoys, short hairpin RNAs (shRNA), micro RNAs (miRNA) and small nucleolar RNAs (snoRNA).

The term "dendrimer" refers to a branched molecule and is synonymous with "arborol" or "cascase molecule." Dendrimers are monodisperse, highly symmetric molecules. Methods of synthesizing dendrimers are known in the art, and are commercially available. Dendrimers can be characterized as high or low molecular weight. In embodiments, the dendrimers of the present disclosure or invention are poly(amidoamine), or PAMAM, dendrimers with tertiary amines at their branching points. Metal ions can be introduced into solution to form a complex with the tertiary amine.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and plants are those that express a heterologous gene or coding sequence, typically as a result of recombinant methods.

The term "exogenous" refers to a molecule or substance (e.g., a compound, nucleic acid or protein) that originates from outside of a given cell or organism. For example, an "exogenous promoter" as referred to herein is a promoter that does not originate from the plant it is expressed by. Conversely, the term "endogenous" or "endogenous promoter" refers to a molecule or substance that is native to, or originates within, a given cell or organism.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "purified" denotes that a nucleic acid or protein gives rise to essentially one band in an electrophoretic gel. In some embodiments, the nucleic acid or protein is at least 50% pure, optionally at least 65% pure, optionally at least 75% pure, optionally at least 85% pure, optionally at least 95% pure, and optionally at least 99% pure.

The term "isolated" may also refer to a cell or sample cells. An isolated cell or sample cells are a single cell type that is substantially free of many of the components which normally accompany the cells when they are in their native state or when they are initially removed from their native state. In certain embodiments, an isolated cell sample retains those components from its natural state that are required to maintain the cell in a desired state. In some embodiments, an isolated (e.g. purified, separated) cell or isolated cells, are cells that are substantially the only cell type in a sample. A purified cell sample may contain at least 60%, 70%, 75%, 80%, 85%, 90%, 95%, 96%, 97%, 98%, 99%, or 100% of one type of cell. An isolated cell sample may be obtained through the use of a cell marker or a combination of cell markers, either of which is unique to one cell type in an unpurified cell sample. In some embodiments, the cells are isolated through the use of a cell sorter. In some embodiments, antibodies against cell proteins are used to isolate cells.

As used herein, the term "conjugate" refers to the association between atoms or molecules. The association can be direct or indirect. For example, a conjugate between a nucleic acid (e.g., ribonucleic acid) or a small molecule and a compound moiety as provided herein can be direct, e.g., by covalent bond, or indirect, e.g., by non-covalent bond. Optionally, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. Thus, the nucleic acid acids can be attached to a compound moiety through its backbone. Optionally, the ribonucleic acid includes one or more reactive moieties, e.g., an amino acid reactive moiety, that facilitates the interaction of the ribonucleic acid with the compound moiety. Additionally, small molecules can be complexed, or altered by a variety of conjugation methods.

Useful reactive moieties or functional groups used for conjugate chemistries herein include, for example:
- (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
- (b) hydroxyl groups which can be converted to esters, ethers, aldehydes, etc.
- (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;
- (d) dienophile groups which are capable of participating in Diels-Alder reactions such as, for example, maleimido groups;
- (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;
- (f) sulfonyl halide groups for subsequent reaction with amines, for example, to form sulfonamides;
- (g) thiol groups, which can be converted to disulfides, reacted with acyl halides, or bonded to metals such as gold;
- (h) amine or sulfhydryl groups, which can be, for example, acylated, alkylated or oxidized;
- (i) alkenes, which can undergo, for example, cycloadditions, acylation, Michael addition, etc;
- (j) epoxides, which can react with, for example, amines and hydroxyl compounds;
- (k) phosphoramidites and other standard functional groups useful in nucleic acid synthesis;
- (l) metal silicon oxide bonding;
- (m) metal bonding to reactive phosphorus groups (e.g. phosphines) to form, for example, phosphate diester bonds; and
- (n) sulfones, for example, vinyl sulfone.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, "about" means a range extending to +/−10% of the specified value. In embodiments, "about" means the specified value.

The terms "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

The terms "identical" or percent "identity", in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical". This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For specific proteins described herein (e.g., TLX, TET3, BTG2, TUSC1, BAK1, LATS2, FZD6, and PPP2R1B), the named protein includes any of the protein's naturally occurring forms, or variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference or functional fragment or homolog thereof.

As used herein, "treatment" or "treating", or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance.

The terms "prevent", "preventing" or "prevention", and other grammatical equivalents as used herein, include to keep from developing, occur, hinder or avert a disease or condition symptoms as well as to decrease the occurrence of symptoms. The prevention may be complete (i.e., no detectable symptoms) or partial, so that fewer symptoms are observed than would likely occur absent treatment. The terms further include a prophylactic benefit. For a disease or condition to be prevented, the compositions may be administered to a patient at risk of developing a particular disease (e.g. cancer), or to a patient reporting one or more of the physiological symptoms of a disease, even though a diagnosis of this disease may not have been made.

An "effective amount" is an amount sufficient to accomplish a stated purpose (e.g. achieve the effect for which it is administered, treat a disease, reduce enzyme activity, reduce one or more symptoms of a disease or condition, reduce viral replication in a cell). An example of an "effective amount" is an amount sufficient to contribute to the treatment, prevention, or reduction of a symptom or symptoms of a disease, which could also be referred to as a "therapeutically effective amount". A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

"Patient" or "subject in need thereof" refers to a living organism suffering from or prone to a disease or condition that can be treated by using the methods provided herein. The term does not necessarily indicate that the subject has been diagnosed with a particular disease, but typically refers to an individual under medical supervision. Non-limiting examples include humans, other mammals, bovines, rats, mice, dogs, monkeys, goat, sheep, cows, deer, and other non-mammalian animals. In embodiments, a patient is human.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. Contacting may include allowing two species to react, interact, or physically touch, wherein the two species may be a recombinant viral particle as described herein and a cell.

As defined herein, the term "inhibition", "inhibit", "inhibiting" and the like in reference to an siRNA or protein-inhibitor interaction means negatively affecting (e.g., decreasing) the activity or function of the protein (e.g. decreasing gene transcription or translation) relative to the activity or function of the protein in the absence of the inhibitor. In embodiments, inhibition refers to reduction of a disease or symptoms of disease (e.g., cancer). In embodiments, inhibition refers to a reduction in the activity of a signal transduction pathway or signaling pathway (e.g.

reduction of viral replication). Thus, inhibition includes, at least in part, partially or totally blocking stimulation, decreasing, preventing, or delaying activation, or inactivating, desensitizing, or down-regulating transcription, translation, signal transduction or enzymatic activity or the amount of a protein (e.g. a viral protein or a cellular protein).

The terms "inhibitor", "repressor" or "antagonist" or "downregulator" interchangeably refer to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. An "inhibitor" is a siRNA, (e.g., shRNA, miRNA, snoRNA, RNA decoy, ribozyme), compound or small molecule that targets TLX or a TLX pathway protein e.g., by binding, partially or totally blocking stimulation, decrease, prevent, or delay activation, or inactivate, desensitize, or down-regulate signal transduction, gene expression or enzymatic activity necessary for protein activity. Inhibition as provided herein may also include decreasing or blocking a protein activity by expressing a mutant form of said protein thereby decreasing or blocking its activity.

"Pharmaceutically acceptable excipient" and "pharmaceutically acceptable carrier" refer to a substance that aids the administration of an active agent to and absorption by a subject and can be included in the compositions of the present disclosure or invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure or invention. One of skill in the art will recognize that other pharmaceutical excipients are useful in the present disclosure or invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the disclosure or invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure or invention can be delivered by transdermally, by a topical route, formulated as applicator sticks, solutions, suspensions, emulsions, gels, creams, ointments, pastes, jellies, paints, powders, and aerosols.

The term "aberrant" as used herein refers to different from normal. When used to described enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

The recombinant nucleic acid provided herein may form part of a viral expression vector. A "viral vector" or "viral expression vector" is a viral-derived nucleic acid that is capable of transporting another nucleic acid into a cell. A viral vector is capable of directing expression (i.e. transcription and/or translation) of an RNA, a protein or proteins encoded by one or more genes carried by the vector when it is present in the appropriate environment. A viral expression vector may include a viral expression vector promoter (e.g., LTR) controlling transcription of an RNA, a protein or proteins encoded by one or more genes carried by the vector when it is present in the appropriate environment. Antisense constructs or sense constructs that are not or cannot be translated are expressly included by this definition. Examples for viral vectors include, but are not limited to retroviral, adenoviral, lentiviral and adeno-associated viral vectors. The viral expression vector provided herein may include nucleic acid sequences encoding for a selectable marker protein to select for cells including the viral expression vector. The viral expression vector may include nucleic acid sequences encoding for an antiviral protein The viral expression vector may further include regulatory sequences necessary to express the selectable marker and/or the antiviral protein. The promoter controlling expression of the selectable marker protein and the antiviral protein is referred to herein as "protein promoter". In embodiments, the viral expression marker includes a protein promoter. In embodiments, the protein promoter is a polymerase II promoter.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), or adrenocortical suppressant (e.g., mitotane, aminoglutethimide), epipodophyllotoxins (e.g., etoposide). In embodiments, chemotherapies may be used in combination with methods and compositions of the present disclosure or invention.

Further examples of anti-cancer agents include, but are not limited to, antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein kinase C inhibitors, protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to 111In, 90Y, or 131I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

The term "sample" includes sections of tissues such as biopsy and autopsy samples, and frozen sections taken for histological purposes. Such samples include blood and blood fractions or products (e.g., bone marrow, serum, plasma, platelets, red blood cells, and the like), sputum, tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish. In some embodiments, the sample is obtained from a human.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely varied in controls, variation in test samples will not be considered as significant.

"Disease" or "condition" refer to a state of being or health status of a patient or subject capable of being treated with a compound, pharmaceutical composition, or method provided herein. In embodiments, the disease is cancer. In embodiments, the disease is a disease related to (e.g. caused by) an aberrant activity of TLX, TET3, including TET3-1 and TET3-2, or other TLX pathway activity, or pathway activated by TLX. In some embodiments, the disease is a brain cancer (e.g. glioblastoma, oligodendroglioma, dysembryoplastic neuroepithelial tumor, mesenchymal gliomas, pilocytic astrocytomas, neurocytoma, or ependymoma) although other cancers are contemplated (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma).

TLX Expression and/or Activity Modulating Agents

The TLX expression and/or activity modulating agents described herein alter the effects of TLX and its pathway proteins. Direct modulation of TLX expression and/or activity can occur at the DNA, RNA, and protein levels. In an embodiment, TLX modulating agents can target TLX DNA (e.g., by gene editing via known methods including Zinc finger nucleases, transcription activator-like effector-based nucleases/TALEN®, CRISPR/Cas9, engineered meganuclease, viral transfections or episomal transfection of TLX-expressing vectors, or activation and/or modulation of the endogenous TLX promoter). In an embodiment, TLX expression and/or activity modulating agents can downregulate the expression of TLX (e.g., by targeting for degradation the mRNA transcript of TLX, or by inhibiting or preventing the transcription or translation of TLX). In an embodiment, TLX expression and/or activity modulating agents can inhibit the expression and/or activity of TLX protein (e.g. by targeting TLX for degradation by antibody binding, or by inhibiting the activity of TLX by small molecule inhibition.)

Furthermore, methods and compositions provided herein can affect the expression and/or activity of the TLX pathway. TLX pathway effectors can also be targeted at the DNA, RNA, or protein level, modulation by TLX expression and/or activity modulating agents. In one embodiment, the therapeutic benefits that are achieved do not necessarily require or involve the loss of p53 activity. In other words, in contrast to what has been previously reported with respect to how the initiation of the glioblastoma and the progression of glioblastoma growth require loss of p53 activity, in one embodiment the disclosure or invention described herein requires only the modulation of the TLX pathway to inhibit glioblastoma tumorigenesis.

Also, the disclosure or invention provided herein identify several potential downstream targets that were not associated with TLX before. Such potential downstream targets of TLX include, but not limited to, TET3, TDG, DICER1, ID3, ID4 and MBD2 genes. The expression of TET3, TDG and DICER1 can be up-regulated and the expression of ID3, ID4, and MBD2 genes can be down regulated upon down-regulation of TLX activity and/or expression.

Therefore, in one aspect, modulation of one or more of such downstream targets of TLX can exhibits effects in preventing and/or treating cancer or tumor in animals. In one embodiment, TET3 expression or activity can be increased (e.g. by viral transduction or episomal transfection of TET3 expressing vectors, transfection of TET3 mRNAs or proteins, activation of the endogenous TET3 promoter, or activation of TET3 activity by small molecules). In particular, the TET3 expression and/or activity modulating agents described herein can alter the effects of TET3 and its pathway proteins. Direct modulation of TET3 can occur at the DNA, RNA, and protein levels. In an embodiment, TET3 modulating agents can target TET3 DNA (e.g., by gene editing via known methods including Zinc finger nucleases, transcription activator-like effector-based nucleases/TALEN®, CRISPR/Cas9, engineered meganuclease, viral transfections or episomal transfection of TET3-expressing vectors, or activation of the endogenous TET3 promoter). In an embodiment, TET3 expression and/or activity modulating agents can downregulate the expression of TET3 (e.g., by targeting for degradation the mRNA transcript of TET3, or by inhibiting or preventing the transcription or translation of TET3). In an embodiment, TET3 expression and/or activity modulating agents can inhibit activity of TET3 protein (e.g. by targeting TET3 for degradation by antibody binding, or by inhibiting the activity of TET3 by small molecule inhibition.)

In embodiments, additional genes for targeting include BTG2, TUSC1, BAK1, LATS2, FZD6, and PPP2R1 as these genes are targets of TLX and TET3. These genes have been shown to be potent tumor suppressors (e.g., BTG2 inhibits proliferation of osteosarcoma[61], TUSC1 is a putative tumor suppressor in gastric cancer[62], hepatocellular carcinoma[63], and lung cancer[64]; LATS2 is involved in pathogenesis of schwannomas as a negative regulator of oncogene YAP[65]; Inhibition of PPP2R1B mediates the drug resistance in colorectal cancer[66]). In one embodiment, modulation of tumor suppressor proteins (e.g. TET3, BTG2, TUSC1, BAK1, LATS2, FZD6, and PPP2R1) does not require modulation of TLX.

Additionally, TLX activity modulating agents can be used in combination (e.g. with other TLX activity modulating agents, or with other known anti-cancer agents). TLX activity modulating agents can further be complexed with delivery agents and pharmaceutically acceptable excipients. In an embodiment, TLX targeted siRNA is complexed with a dendrimer nanoparticle for delivery. In an embodiment, targeted shRNA is delivered by lentiviral delivery.

Ribonucleic Acid Compounds

The ribonucleic acid compounds provided herein, including embodiments thereof, are, inter alia, capable of delivery into a cell and inducing degradation of TLX and/or its downstream target(s) such as TET3. The ribonucleic acids of the present disclosure or invention include siRNA and shRNAs.

Example shRNAs include TLX shRNA-1 (SEQ ID NO: 1; 5'-GCC GCC ATT GCA GCC CTT CAA-3') and TLX shRNA-1 scrambled control (SEQ ID NO: 2; 5'-CAG TCC ATC AGA CCC TCG CTG-3'), TLX shRNA-2 (SEQ ID NO: 3; 5'-GGA AGT CAA CAT GAA CAA AGA-3') and TLX shRNA-2 scrambled control (SEQ ID NO: 4; 5'-ACT CAA AAG GAA GTG ACA AGA-3'), shRNA control for TET3 (SEQ ID NO: 5; 5'-GTT CAG ATG TGC GGC GAG T-3'), shTET3-1 (SEQ ID NO: 6; 5'-CCG AAG CTG TGT CCT CTT A-3'), and shTET3-2 (SEQ ID NO: 7; 5'-GGA GTC ACC TCT TAA GTA C-3').

Example siRNAs included sequence of sense: SEQ ID NO: 51; 5'-CCG CCA AUU GCA GCC CUU CAA GAU dGdA-3', antisense: SEQ ID NO: 52; 5'-UCA UCU UGA AGG GCU GCA AUG GCG GGG-3'. The control siRNA has the sequence of sense: SEQ ID NO: 53; 5'-CAU CCA UCA GAC CCU CGC UGG AU dGdA-3', antisense: SEQ ID NO: 54; 5'-UCA UCC AGC GAG GGU CUG AUG GAU GGG-3'.

RNA interference holds great promise for tumor therapy. However, efficient delivery of small RNAs in vivo represents a major challenge preventing RNA interference from achieving the potency required for successful clinical applications. After ups and downs, RNA interference is now regaining its momentum[27]. Various delivery technologies have been developed for RNA interference. Viral vectors have high delivery efficiency and allow sustained gene silencing with a single injection, offering practical advantage for diseases associated with hard-to-reach organs, such as the brain[27,28]. Non-viral vectors, such as cationic lipids and polymers, are developed to increase safety and efficiency of delivery[29,30].

Ribonucleic acid compounds of the present disclosure or invention can be delivered into a cell inducing knockdown of TLX, also known as NR2E1, having GenBank Accession No. NM_003269.4.

Small Molecule Activators

Small molecules may be used as activators of TLX. In embodiments, small molecule activators of TLX bind to the ligand binding domain of TLX. In embodiments, small molecular activators are known nuclear receptor ligands. In some embodiments, all-trans retinoic acid (ATRA) (structure 1. below) can activate TLX.

Structure 1

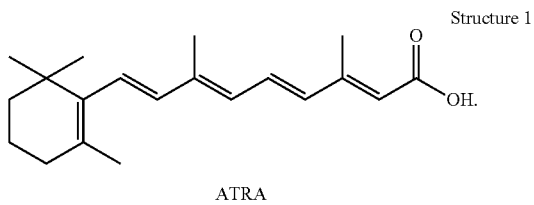

ATRA

In some embodiments, small molecule activators may be derivatives or conjugates of known nuclear receptor ligands.

In some embodiments, treatment of GSCs with ATRA can induce the expression of TET3, a tumor suppressor, to inhibit GSC growth, self-renewal and tumorigenesis, thereby proving that regulation, e.g. activation of TLX by small molecules can be used to inhibit GSC self-renewal and tumorigenesis.

Methods of Delivery

As described herein RNA compounds may, in embodiments, utilize nanoparticles to deliver compound moieties or compounds (e.g., therapeutic agents) into a cell. In embodiments, the nanoparticles are dendrimers (e.g. PAMAM dendrimers, amphiphilic dendrimers[58,59], and arginine-decorate amphiphilic dendrimers[60]). In embodiments, the dendrimers are PAMAM dendrimers. PAMAM dendrimers have been previously described and have been shown to compact small RNAs, such as the RNA compounds of the present disclosure or invention into nanoparticles, protecting the RNAs from enzymatic degradation. In embodiments, the dendrimers are polypeptide coated. In particular, a RGDK peptide (with the sequence of $E_{16}G_6RGDK$, SEQ ID NO: 55) coated dendrimer may increase delivery efficiency of the RNA compounds.

In some embodiments, use of dendrimer results in effective delivery of TLX-modulating agent by forming stable and compact nanoparticles with the agent, e.g. siRNA and/or shRNA of TLX, and protect siRNA and/or shRNA from degradation, leading to efficient and long-term gene silencing. The dendrimer-mediated delivery is also relatively safe without discernible toxicity.

Dendrimers, a type of synthetic polymers, are one of the most promising non-viral vectors for delivering small RNAs by virtue of their well-defined structure and unique multi-valent cooperativity alongside the high payload confined within a nanosized volume[31-33]. In particular, poly(amidoamine) dendrimers bear amine groups at the terminals, which can effectively interact with negatively-charged nucleic acids under physiological conditions[34]. They also have tertiary amines in the interior, which can promote the intracellular release of nucleic acids through the "proton sponge" effect[35]. However, dendrimer-based delivery of small interfering RNAs (siRNAs) into tumor stem cells was previously largely unexplored.

As illustrated herein, the present disclosure or invention show that dendrimer can form stable nanoparticles with small RNAs (e.g. siRNA and/or shRNA) and deliver small RNAs into GSCs effectively. The dendrimer-small RNA complex is able to protect small RNA from RNase-mediated degradation as compared to the treatment of naked small RNA, which is rapidly degraded upon RNase digestion.

In some embodiments, an N/P ([total terminal amines in a dendrimer]/[phosphates in small RNA]) ratio in a dendrimer-small RNA complex can be 1.0 or above. In certain embodiments, the N/P ration can be 1, 2, 3, 4, 5, 6, 7, 8, 9, 10, 15, 20, 25, 30 or more. In some embodiments, the N/P ration can be lower than 1.0 or higher than 30.0.

In some embodiments, nanoparticle(s) comprising dendrimer and small RNA with or without polypeptide coating can have a size around 100 nm in diameter. In some other embodiments, the diameter of nanoparticle(s) can be any range from about 1 to 10 nm, 10 to 20 nm, 20 to 30 nm, 30 to 40 nm, 40 to 50 nm, 50 to 60 nm, 60 to 70 nm, 70 to 80 nm, 80 to 90 nm, 90 to 100 nm, 100 nm to 200 nm, 200 nm to 500 nm, 500 nm to 1000 nm or higher. In some embodiments, the diameter of nanoparticle(s) can be less than about 1 nm.

In some embodiments, a dendrimer-small RNA nanocomplex can be coated with polypeptide. In certain embodiments, the nanocomplex can be coated with RGDK to achieve efficient knockdown of the target of small RNA. As illustrated herein, treatment with RGDK-coated a dendrimer-TLX siRNA nanocomplex induces even more potent TLX knockdown, presumably due to better cell penetration. Therefore, polypeptide-coated dendrimer-siRNA complex can efficiently knock down expression of the target of siRNA in tumor cells and suppresses growth of the tumor potently.

It is also illustrated in the present disclosure or invention that small RNA, e.g. TLX-siRNA, delivered by polypeptide-coated dendrimer can suppress tumor progression in a human GSC. Moreover, treatment with the polypeptide-coated dendrimer-siRNA complex can significantly extend a lifespan of an animal having GSC-affected animal. Therefore, a peptide-coated dendrimer-delivered siRNA can effectively decrease tumor growth and increase the lifespan of tumor-bearing animals.

In embodiments, viral vector delivery can be used to deliver the RNA compounds of the present disclosure or invention. Examples for viral vectors include, but are not limited to retroviral, adenoviral, lentiviral and adeno-associated viral vectors. The viral expression vector provided herein may include nucleic acid sequences encoding for a selectable marker protein (e.g., purimycin) to select for cells including the viral expression vector.

In embodiments, dendrimers for delivery of RNA compounds into a cell include, but are not limited to, PAMAM dendrimers at different generations (e.g. G4, G5, G6, or G7 PAMAM dendrimers), other type of dendrimers and their derivatives (e. g. amphiphilic dendrimer[58,59], arginine-decorated amphiphilic dendrimer[60]), or dendrimers with other coating or decorations (e.g. coating dendrimer-siRNA nanoparticles with an angiopep-2 peptide, which mediates active transport across the blood brain barrier).

In embodiments, other delivery vectors (e.g. lipid and polymers) could also be alternative way to deliver small RNA, e.g. TLX siRNA.

Methods of Treatment

The compositions and/or pharmaceutical formulations of the compositions described herein can be used to treat or providing palliative treatment to individuals having or are suspected of having brain cancer. The brain cancer can be, but is not limited to, glioblastoma, oligodendroglioma, dysembryoplastic neuroepithelial tumor, mesenchymal gliomas, pilocytic astrocytomas, neurocytoma, and ependymoma. In one aspect, the individual is a patient under the care of a physician. In other aspects or embodiments, the compositions and/or pharmaceutical formulations can be used to treat individuals who are not undergoing surgery. In other aspects, the compositions and/or pharmaceutical formulations can be used in conjunction with surgical treatment (e.g., de-bulking). In one embodiment, the compositions and/or pharmaceutical formulations can be administered about the same time as the surgical procedure. In other aspects, the compositions and/or pharmaceutical formulations can be administered after the surgery as part of post-surgical care. The compositions and/or pharmaceutical formulations can be administered before, during or after other types of anti-cancer treatments as well as as part of treatment plan to address any recurrence of cancer.

As used herein, "treatment" or "treating", or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a brain cancer (e.g. glioblastoma multiform), or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance. For example, certain methods herein treat cancer (e.g. glioblastoma, oligodendroglioma, dysembryoplastic neuroepithelial tumor, mesenchymal gliomas, pilocytic astrocytomas, neurocytoma, or ependymoma). For example certain methods herein treat cancer by decreasing or reducing or preventing the occurrence, growth, metastasis, or progression of cancer; or treat cancer by decreasing a symptom of cancer. Symptoms of cancer would be known or may be determined by a person of ordinary skill in the art.

An "effective amount" is an amount sufficient to accomplish a stated purpose (e.g. achieve the effect for which it is administered, treat a disease, reduce activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount". A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount", as used herein, refers to an amount of antagonist required to decrease the activity of an enzyme or protein relative to the absence of the antagonist. A "function disrupting amount", as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

In another aspect, a method of treating cancer is provided. The method includes administering to a subject in need thereof an effective amount of the ribonucleic acid compound as provided herein (including embodiments thereof). The method includes administering to a subject in need thereof an effective amount of an anticancer agent and the ribonucleic acid compound as provided herein including embodiments thereof.

In another aspect, a method of treating a cancer or proliferative disorder in a subject in need thereof is provided. The method includes administering to the subject a therapeutically effective amount of a nucleic acid compound or other modulator as provided herein including embodiments thereof. In embodiments, the cancer is a brain cancer. In embodiments, the cancer is glioblastoma.

Kits

In another aspect, a kit including nucleic acid compounds or small molecules of the ivnention are provided. In embodiments, the kit includes instructions for making a nucleic acid and/or small molecule compound of the disclosure or invention, including instructions for construct a compound for delivery (e.g. dendrimer, or peptide coated dendrimer). In embodiments the kit includes a recombinant nucleic acid compound, dendrimer, or peptide coating described herein, including in any aspect, embodiment, example, claim, or figure.

EXAMPLES

Methods
Cell Culture

Sphere cultures of GSCs were established from freshly dissociated surgical specimens as described[36]. Patients were newly diagnosed as grade IV glioblastoma multiforme based on WHO-established guidelines. All patient tissues were obtained in accordance with Institutional Review Board-approved protocols. The GSCs were maintained in DMEM-F12 medium (Omega Scientific) supplemented with 1× B27 (Invitrogen), 5 μg per ml heparin (Sigma), 2 mM L-glutamine (Media Tech), 27.4 mM HEPES (Fisher), 20 ng per ml EGF (PeproTech) and 20 ng per ml FGF (PeproTech) with growth factors replenished twice a week. GSCs were treated with accutase (Innovative Cell Technologies) for cell dissociation and induced into differentiation using 0.5% fetal bovine serum and 1 μM all-trans retinoic acid. All the cultures used in this study were confirmed for the lack of mycoplasma contamination using MycoAlert™ PLUS Mycoplasma Detection Kit (Lonza).

Plasmid DNA Preparation, Viral Production and Transduction shRNAs or the scrambled control RNAs were cloned into lentiviral pHIV7-GFP or pHIV-TetR-GFP vector. The sequences for shRNAs include TLX shRNA-1 (SEQ ID NO: 1. 5'-GCC GCC ATT GCA GCC CTT CAA-3') and TLX shRNA-1 scrambled control (SEQ ID NO: 2. 5'-CAG TCC ATC AGA CCC TCG CTG-3'), TLX shRNA-2 (SEQ ID NO: 3. 5'-GGA AGT CAA CAT GAA CAA AGA-3') and TLX shRNA-2 scrambled control (SEQ ID NO: 4. 5'-ACT CAA AAG GAA GTG ACA AGA-3'), shRNA control for TET3 (SEQ ID NO: 5. 5'-GTT CAG ATG TGC GGC GAG T-3'), shTET3-1 (SEQ ID NO: 6. 5'-CCG AAG CTG TGT CCT CTT A-3'), and shTET3-2 (SEQ ID NO: 7. 5'-GGA GTC ACC TCT TAA GTA C-3')[53]. Lentiviruses were produced using 293T cells. To transduce GSCs, spheres were dissociated and incubated with lentivirus and 4 μg per ml polybrene for 24 hours. Human TET3-expressing vector EX-H2292-M11 was purchased from GeneCopoeia and hTET3 sequences were subcloned into CSC lentiviral vector to get TET3-2-expressing vector. Human TET3 CXXC domain sequences were amplified from human neural stem cell cDNAs and subcloned into TET3-2-expressing vector to get TET3-1-expressing vector that expresses full length of TET3 gene.

RT-PCR

Total RNAs were isolated with Trizol reagent (Invitrogen) or RNeasy Mini Kit (Qiagen). Reverse transcription (RT) was performed using the Tetro cDNA synthesis Kit (Bio-LINE). RT-PCR reactions were performed using SYBR Green Master Mix (Thermo Scientific) on Step One Plus Real-Time PCR instrument (Applied Biosystems). The primers for RT-PCR are listed in Table 1. Actin or GAPDH was used as the reference gene for normalization. The ΔΔCt method was used for quantification analysis.

TABLE 1

Primer sequences for RT-PCR and ChIP

| Gene | Strand | Sequence | Assay | SEQ ID NO: |
|---|---|---|---|---|
| GAPDH | Forward | 5'-CCT GTT CGA CAG TCA GCC G-3' | RT-PCR | 8 |
|  | Reverse | 5'-CGA CCA AAT CCG TTG ACT CC-3' |  | 9 |
| Actin | Forward | 5'-CCG CAA AGA CCT GTA CGC CAA C-3' | RT-PCR | 10 |
|  | Reverse | 5'-CCA GGG CAG TGA TCT CCT TCT G-3' |  | 11 |
| TLX | Forward | 5'-CTA AGA GTG TGC CAG CCT TC-3' | RT-PCR | 12 |
|  | Reverse | 5'-TGT TAG CAT CAA CCG GAA TGG-3' |  | 13 |
| TET3 | Forward | 5'-CAG CAG CCG AGA AGA AGA AG-3' | RT-PCR | 14 |
|  | Reverse | 5'-GGA CAA TCC ACC CTT CAG AG-3' |  | 15 |
| BTG2 | Forward | 5'-CTC CAT CTG CGT CTT GTA CGA-3' | RT-PCR | 16 |
|  | Reverse | 5'-AGA CTG CCA TCA CGT AGT TCT-3' |  | 17 |
| TUSC1 | Forward | 5'-TGA AGA GGC CAG CAC GAA CC-3' | RT-PCR | 18 |
|  | Reverse | 5'-AGT CGG GTT CCT GTA GAG GC-3' |  | 19 |
| BAK1 | Forward | 5'-GCT CCC AAC CCA TTC ACT AC-3' | RT-PCR | 20 |
|  | Reverse | 5'-TCC CTA CTC CTT TTC CCT GA-3' |  | 21 |

TABLE 1-continued

Primer sequences for RT-PCR and ChIP

| Gene | Strand | Sequence | Assay | SEQ ID NO: |
|---|---|---|---|---|
| LATS2 | Forward | 5'-GTG TCT AAC TGT CGG TGT GG-3' | RT-PCR | 22 |
|  | Reverse | 5'-TCA CTC CAA CAC TCC ACC AG-3' |  | 23 |
| FZD6 | Forward | 5'-CGA TAG CAC AGC CTG CAA TA-3' | RT-PCR | 24 |
|  | Reverse | 5'-ACG GTG CAA GCC TTA TTT TG-3' |  | 25 |
| PPP2R1B | Forward | 5'-TTC CAC TGT TCA CTA GTC-3' | RT-PCR | 26 |
|  | Reverse | 5'-CCA AAG TCT CAA GGT CAT C-3' |  | 27 |
| hTLX | Forward | 5'-GAC AAC TCC GGT TAG ATG CTA C-3' | RT-PCR | 28 |
|  | Reverse | 5'-GAG CCT CAT CTT GAA GGG CTG-3' |  | 29 |
| hTET3 | Forward | 5'-CAG CAG CCG AGA AGA AGA AG-3' | RT-PCR | 14 |
|  | Reverse | 5'-GGC CTG GGT CCG ACG TAA TG-3' |  | 30 |
| hBTG2 | Forward | 5'-CCT ATG AGG TGT CCT ACC GC-3' | RT-PCR | 31 |
|  | Reverse | 5'-CTC CGG CCC AGC AGC ACT T-3' |  | 32 |
| TET3-P1 | Forward | 5'-TTG AGA AGA GGC ATC CAT CC-3' | ChIP | 33 |
|  | Reverse | 5'-AGA ACC ACA GTC GTT TCC TG-3' |  | 34 |
| TET3-P2 | Forward | 5'-TGT AAT CCC AGC TCC TGA GG-3' | ChIP | 35 |
|  | Reverse | 5'-GGT TGA CAG ACT GAA CAG GG-3' |  | 36 |
| TET3-P3 | Forward | 5'-ATT CTA GCC CAC CAC TCA CC-3' | ChIP | 37 |
|  | Reverse | 5'-TGT GCC AAC CAT GTT GTA GG-3' |  | 38 |
| TET3-P4 | Forward | 5'-TGG CTC AGA GAA CCT CAA GG-3' | ChIP | 39 |
|  | Reverse | 5'-ACT GCC CTC CTC TGT CAT TG-3' |  | 40 |
| TET3-P5 | Forward | 5'-CCT GTC GCA AAG TCA GAA TC-3' | ChIP | 41 |
|  | Reverse | 5'-TGC CCT TGT TCT CAG GAT AC-3' |  | 42 |
| TET3-P6 | Forward | 5'-GTG TGT ACA CAC AGG CTT GG-3' | ChIP | 43 |
|  | Reverse | 5'-TCA CAC AAA TGA GGC TCT CC-3' |  | 44 |
| TET3-P7 | Forward | 5'-GAA GAC CAG GTC AGG GTC TG-3' | ChIP | 45 |
|  | Reverse | 5'-AAG GCA AGG CTT AGA AGT GG-3' |  | 46 |
| BTG2 | Forward | 5'-ACC TCC CTG GAC CTC CTG AA-3' | hMeDIP-qPCR | 47 |
|  | Reverse | 5'-TCA GTG AGA GGT CTC GGG TG-3' |  | 48 |
| PPP2R1B | Forward | 5'-CAA CGA GCT GGA TGA ATC CC-3' | hMeDIP-qPCR | 49 |
|  | Reverse | 5'-TTA AGG CTC CCT TCT GAC CC-3' |  | 50 |

Immunostaining

For immunofluorescence, cells were fixed with 4% paraformaldehyde and permeabilized in 0.3% Triton X-100. Antibodies included rabbit anti-TLX (1:1000; Shi lab)[45], mouse anti-nestin (1:2000; BD Pharmingen; Catalog #611659)[54], rabbit anti-integrin αv (1:500; Chemicon; Catalog # AB1923)[43], mouse anti-neuropilin-1 (1:11; Miltenyi Biotec; Catalog #130-090-693)[43], mouse anti-GFAP (1:1000; Sigma; Catalog # G3893) and rabbit anti-Tuj1 (1:6000; Covance; Catalog # PRB-435P)[55].

Animals

All animal related work was performed under the IACUC protocol 05050 approved by the City of Hope Institutional Animal Care and Use Committee. NSG mice (the Jackson Laboratory) at 6-8 weeks old were used. The sample size was determined based on using t-test for two-group independent samples to reach power of 0.8 and the significance level of 0.05. p<0.05 was considered statistically significant. When monitoring tumor growth, investigators were blind to the group allocation during the bioluminescence xenogen imaging and aware of group allocation when assessing the outcome.

Viral Transduction Followed by Transplantation

GSCs were transduced with control RNA or relevant shRNA expressing lentivirus. Two days after virus transduction, 5×10^4 cells were transplanted into the frontal lobes of brains of 6-8 weeks old NSG mice by stereotaxic intracranial injection. Briefly, 2 μl dissociated cells in PBS were injected into the following site (AP +0.6 mm, ML +1.6 mm and DV −2.6 mm) with a rate of 1 μl per min. The same coordinates were used for all intracranial injections in this study. Mouse brains were harvested when severely sick mouse was found in treated or control group. H&E staining was performed on 20 μm coronal sections of frozen brain samples, followed by tumor size analysis. The tumor volume was measured by multiplying the area of the tumor tissues (quantified by Image J) by the thickness of the sections, then multiplying by the number of the sections that contain the tumor tissues. In a separate set of experiment, the survival of grafted mice was recorded and analyzed.

Intracranial Viral Transduction

PBT003 cells (2×10^5) transduced with luciferase expressing lentivirus were intracranially transplanted into the frontal lobe of 6-8 week-old NSG mice. One week or two weeks later, mice were randomly grouped and treated with scrambled control RNA or TLX shRNA-expressing lentivirus by intratumoral injection. Tumor growth was monitored by bioluminescence xenogen imaging. The bioluminescence intensity was quantified. Six weeks after virus treatment, mouse brains were collected and H&E staining was performed on brain sections. In a separate set of experiment, the survival of mice after virus treatment was recorded and analyzed.

Dendrimer-Based siRNA Delivery In Vitro

The G5 dendrimer and RGDK peptide were synthesized as previously described[40]. The TLX siRNA has the sequence of sense: SEQ ID NO: 51: 5'-CCG CCA UUG CAG CCC UUC AAG AU dGdA-3', antisense: SEQ ID NO: 52: 5'-UCA UCU UGA AGG GCU GCA AUG GCG GGG-3'. The control siRNA has the sequence of sense: SEQ ID NO: 53: 5'-CAU CCA UCA GAC CCU CGC UGG AU dGdA-3', antisense: SEQ ID NO: 54: 5'-UCA UCC AGC GAG GGU CUG AUG GAU GGG-3'. To form RGDK-coated G5 dendrimer-siRNA complexes, G5 was first mixed with siRNAs at N/P ([total terminal amines in G5]/[phosphates in siRNA]) ratio of 5 and kept at 37° C. for 30 min. Then RGDK peptide was added to the G5-siRNA complex at G5/RGDK molar ratio of 0.426 and incubated at 37° C. for another 10 min. The G5-siRNA or RGDK-G5-siRNA complexes were then added to GSCs. PBT003 cells ($2\times10^5$) were treated with Cy3-siRNA alone (50 nM), G5 dendrimer-siRNA, or RGDK-coated G5 dendrimer-siRNA (N/P ratio of 5; G5/RGDK ratio of 0.426). Two days after, cellular uptake of Cy3-labeled siRNA delivered by siRNA alone, G5 dendrimers, or RGDK-coated G5 dendrimers was monitored by fluorescence microscopy and flow cytometry. For knocking down of TLX, PBT003 cells were treated with the G5 dendrimer-TLX siRNA complex or G5-control siRNA complex with or without RGDK coating, TLX expression was analyzed by RT-PCR after two days of dendrimer-TLX siRNA treatment.

Intracranial Delivery of Dendrimer-siRNA Nanoparticles

PBT003 cells ($2\times10^5$) transduced with luciferase expressing lentivirus were intracranially transplanted into the frontal lobe of 6-8 week-old NSG mice. One week after transplant, tumors were detected by bioluminescence imaging and mice were treated with RGDK coated G5 dendrimer-TLX siRNA complex or RGDK coated G5 dendrimer-SC complex (2.5 nmole siRNA per mouse with N/P ratio of 5, G5/RGDK ratio of 0.426) by intratumoral injection once a week for six weeks. Tumor growth was monitored by bioluminescence imaging once a week for 7 weeks. The bioluminescence intensity, mouse body weight and mouse survival were analyzed.

Microarray Analysis and Glioblastoma Subtype Determination

For glioblastoma (GBM) subtype characterization, total RNAs were extracted from ten lines of GSCs using RNeasy Mini Kit (Qiagen). Microarray analysis was performed using GeneChip Human Genome U133A 2.0 Array (Affymetrix). Microarray labeling, hybridization, and quality control measurements were performed in the Integrative Genomics Core of City of Hope. The microarray expression data of the ten GSC samples were pooled together with published microarray expression data of 173 TCGA samples[37]. After batch removal, principle component analysis (PCA) was performed on the pooled dataset using Partek Genomics Suite software, version 6.6 (2014 Partek Inc.) 747 relevant genes were used for PCA according to the data filtering approach as described[37]. Centroids of the four GBM subtype clusters were defined by PCA and the Euclidean distance of each GSC sample to the centroids were calculated. Samples were classified to the GBM subtype that has the least Euclidean distance value.

To identify TLX or TET3 downstream target genes, PBT003 cells were transduced with scrambled control RNA or TLX shRNA expressing lentivirus (for shTLX microarray), or control RNA or TET3 shRNA expressing lentivirus (for shTET3 microarray). Three days after virus transduction, total RNA was extracted using RNeasy Mini Kit (Qiagen). Microarray analysis was performed using GeneChip PrimeView Human Gene Expression Array (Affymetrix). Microarray labeling, hybridization, and quality control measurements were performed in the Integrative Genomics Core of City of Hope. Microarray analysis was performed using Partek Genomics Suite (Partek, Inc., St. Louis, Mo.). Expression values were RMA normalized[56], and fold-change values were calculated using least-squares mean between samples. Genes were defined as differentially expressed if they showed an absolute value of fold-change larger than 1.5. Heatmaps to visualize differentially expressed genes were produced in Partek using Euclidian distance for hierarchical clustering of standardized expression values.

Cell Growth and Sphere Formation Analysis

PBT cells were transduced with relevant shRNA or specific gene-expressing lentivirus. For growth analysis, the transduced cells were cultured for 4 to 10 days in 24-well plates, and cell numbers were counted using a hemocytometer every 2 or 3 days. For sphere formation assay, the transduced cells were seeded at 100 cells per well in 48-well plates and cultured for 2 to 3 weeks followed by analysis of sphere number under microscope. The sphere formation rate was defined as the percentage of sphere-forming cells out of the 100 starting cells.

In Vitro Limiting Dilution Assay

PBT cells transduced with control RNA or relevant shRNA expressing lentivirus were seeded at 1, 5, 10, 20, 50, and 100 cells per well into a 96-well plate. Ten days after seeding, the number of neurospheres in each well was counted. Extreme limiting dilution analysis was performed as described[51,57] using software available at http://bioinf.wehi.edu.au/software/elda.

CellTiter-Glo Luminescent Assay

PBT003 cells were treated with G5 dendrimers or RGDK-coated G5 dendrimers complexed with 100 nM scrambled control RNA or TLX siRNA at N/P ratio of five. Three days after treatment, cells were seeded at 5,000 cells per well in a 96-well plate. After another three days, cells were subjected to CellTiter-Glo luminescent assay (Promega). The luminescent intensity is an indication of relative cell number.

Dox Inducible Knockdown

PBT003 or PBT707 cells were transduced with lentivirus expressing dox-inducible TLX shRNA, with or without lentivirus expressing dox-inducible TET3 shRNA. PBT003 cells ($1\times10^5$) or PBT707 cells ($5\times10^4$) were induced with dox (5 μg per ml for PBT003, 2 μg per ml for PBT707) or without dox every other day for 6 days (for PBT003) or 4 days (for PBT707), followed by cell counting using a hemocytometer. PBT003 or PBT707 cells without viral transduction were used as controls to test toxicity from dox. For gene knockdown effect, total RNA was extracted 4 days after dox induction, followed by RT-PCR.

In Vivo Gene Knockdown

PBT003 cells ($2\times10^5$) were intracranially transplanted into the frontal lobes of 6-8 weeks old NSG mice. One week later, the transplanted mice were treated with scrambled control RNA or TLX shRNA-expressing lentivirus by intratumoral injection. Three days after viral transduction, total RNA was extracted from tumor tissues and RT-PCR was performed using human gene-specific primers to determine in vivo TLX knockdown and expression of downstream target genes TET3, BTG2, and PPP2R1B.

ChIP Assay

ChIP assay was performed as previously described[45]. Briefly, 5 million PBT003 or PBT707 cells and 5 µg TLX antibody[45], 0.5 µg trimethyl H3K4 antibody (HeK4me3, Cell Signaling; Catalog #9727), or 0.5 µg trimethyl H3K9 antibody (H3K9me3, Abcam; Catalog # Ab8898-25) were used for each immunoprecipitation assay. The precipitation was performed using magnetic beads conjugated protein G (Thermo fisher). Primers used are listed in Table 1.

5hmC Dot Blot

PBT003 cells were transduced with relevant shRNA-expressing lentivirus. Three days after, genomic DNA was extracted (QIAamp DNA Mini Kit) and subjected to dot blot analysis using an antibody specific for 5hmC (1:5,000; Active Motif; Catalog #39770)[50].

Hydroxymethylated DNA Immunoprecipitation (hMeDIP)-qPCR

PBT003 cells were transduced with relevant shRNA-expressing lentivirus. Three days after, hydroxymethylated DNA immunoprecipitation assay was performed using 5 million cells and 1 µl rabbit anti-5hmC antibody (Active Motif; Catalog #39770)50 for each reaction. The immunoprecipitation was carried out using magnetic beads conjugated protein G (Thermo fisher). Primers used for BTG and PPP2R1B RT-PCR are listed in Table 1.

Agarose Gel Analysis of the G5-siRNA Complexes

Dendrimer G5 was diluted to an appropriate concentration in 50 mM Tris-HCl buffer (pH 7.4) and stored at 4° C. The TLX siRNA was diluted in H2O. The G5 and TLX siRNA were mixed at indicated N/P ratios and incubated at 37° C. for 30 min. The final concentration of siRNA was adjusted to 25 ng per µl. Four µl of the G5-siRNA complexes were analyzed by electrophoretic mobility shift assays using 1.2% agarose gel and standard TAE buffer. The siRNA bands were stained by ethidium bromide and detected by a Kodak EDAS 290 camera.

The G5-siRNA Complex Protects siRNA from RNase Digestion

TLX siRNA (1.2 µg) and G5 at N/P ratio of 5 were kept at 37° C. for 30 min. Then the complexes were incubated in the presence of 0.01 µg per µl RNase A (QIAGEN) for 0, 5, 10, 20, 30, or 45 min at 37° C. Five µl of siRNA-dendrimer complexes at each condition were added to 1.875 µl 1% SDS solution on ice and then subjected to electrophoresis in 1.2% agarose gel and standard TAE buffer. The siRNA bands were stained by ethidium bromide and detected by a Kodak EDAS 290 camera.

Size Measurement of G5-siRNA Complexes

The TLX siRNA aqueous solution was mixed with indicated amount of the dendrimer G5 aqueous solution at N/P ratio of 5 in the absence or presence of the RGDK peptide. The final concentration of the siRNA was 1 µM. After incubation at 37° C. for 30 min, size measurement was performed using Zetasizer Nano-ZS (Malvern, Ltd. Malvern, U. K.) with a He—Ne ion laser of 633 nm.

Example 1

Knockdown of TLX Reduces GSC Self-Renewal and Tumorigenesis

Figure 9A:
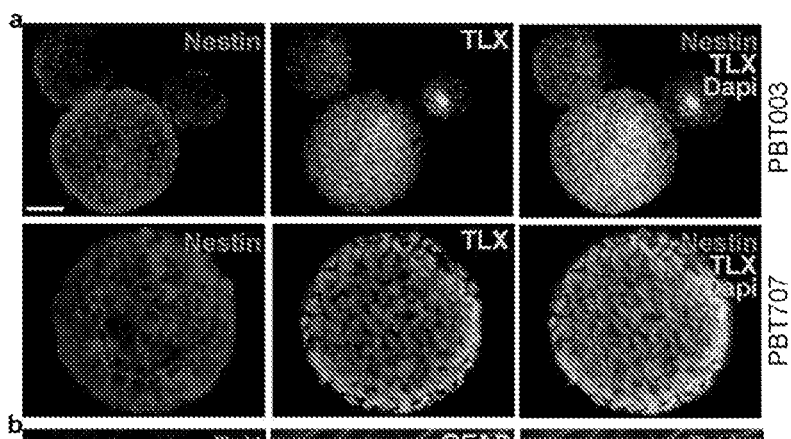
FIG. 9A-9C are images showing characterization of GSCs.
Figure 9B:
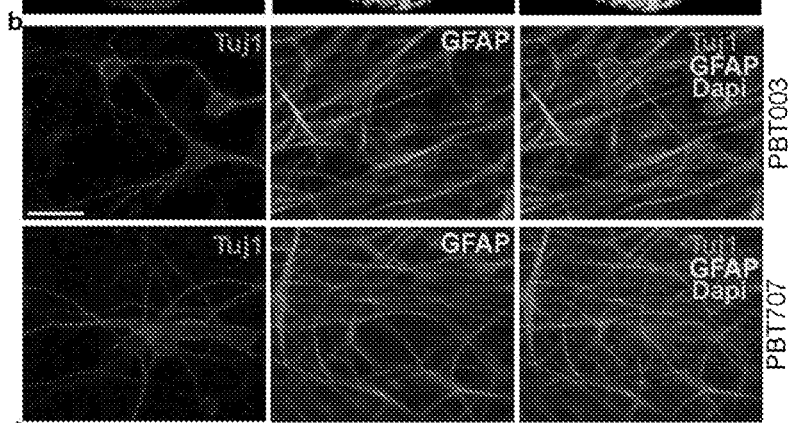
Figure 9C:
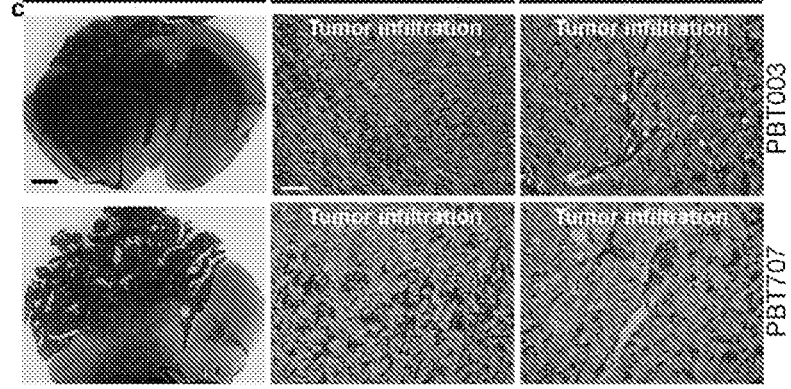

To determine the role of TLX in human GSCs, ten primary GSC lines were isolated from tumor tissues of newly diagnosed human WHO grade IV glioblastoma patients and cultured them as three-dimensional tumor-spheres in DMEM F12 media supplemented with B27, EGF and FGF, a culture condition for GSC enrichment[36]. These GSCs were classified into glioblastoma subtypes as previously reported[37]. Among them, PBT003, PBT022, PBT726 and PBT1030 are classical, PBT017, PBT030 and PBT1008 are mesenchymal, while PBT024, PBT111 and PBT707 are proneural. These GSCs expressed human neural stem cell markers, Nestin and TLX (FIG. 9a). They are also multipotent. When cultured in differentiation condition, they were able to differentiate into βIII tubulin-positive neurons and GFAP-positive astrocytes (FIG. 9b). After transplantation into NSG mice, these cells could form brain tumors with typical infiltrative features of glioblastoma (FIG. 9c).

Figure 1B:
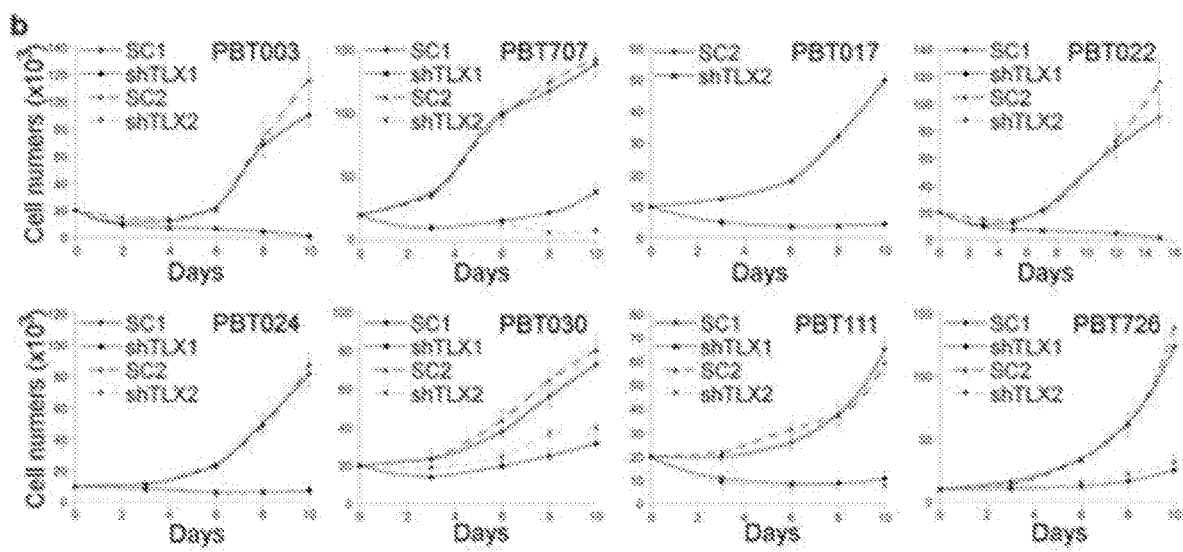

To study the function of TLX in GSCs, two shRNAs were designed to knockdown TLX expression in GSCs with two scrambled RNAs as negative controls. After stably transducing TLX shRNA-expressing lentivirus into GSCs, efficient knockdown of TLX was confirmed (FIG. 1a). Knockdown of TLX expression dramatically reduced the growth rate of all GSC lines tested (FIG. 1b), suggesting that TLX plays an important role in the expansion of GSCs.

Figure 2A:
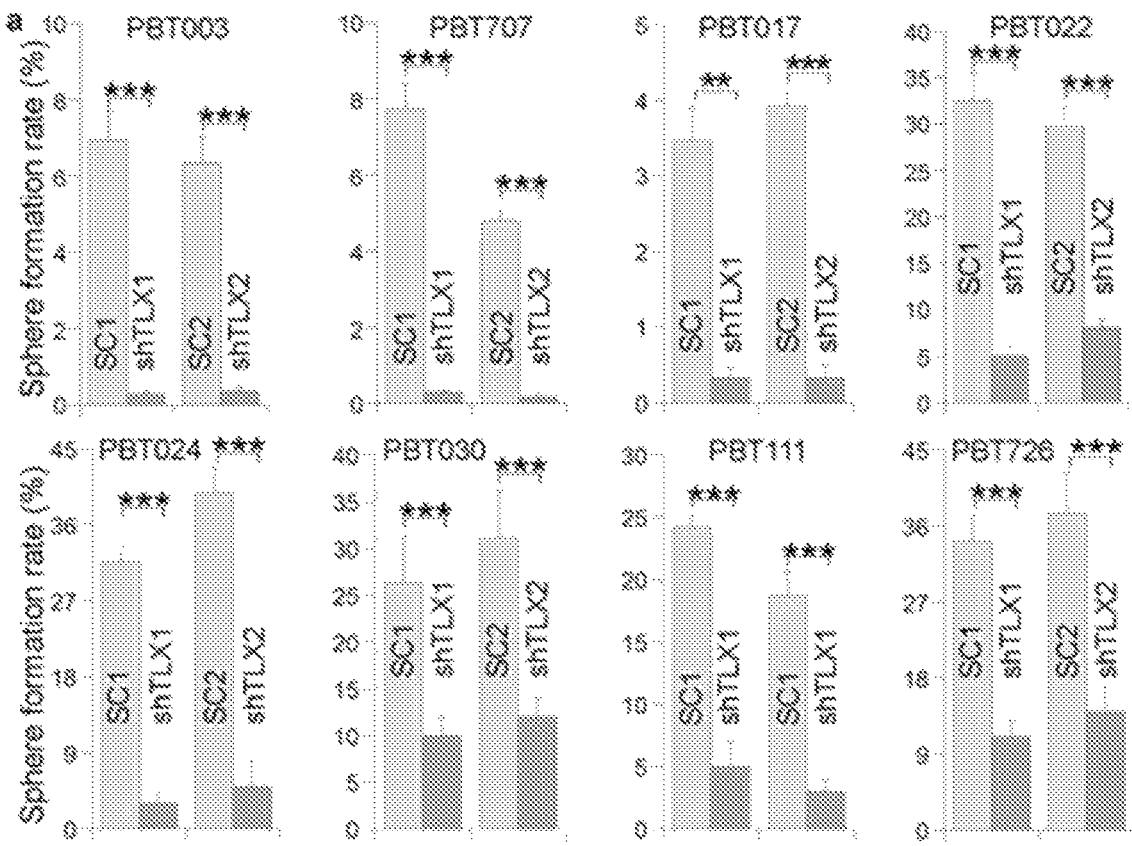
FIGS. 2A and 2B demonstrate that knocking down TLX expression dramatically reduced the self-renewal of GSCs.
Figure 2B:
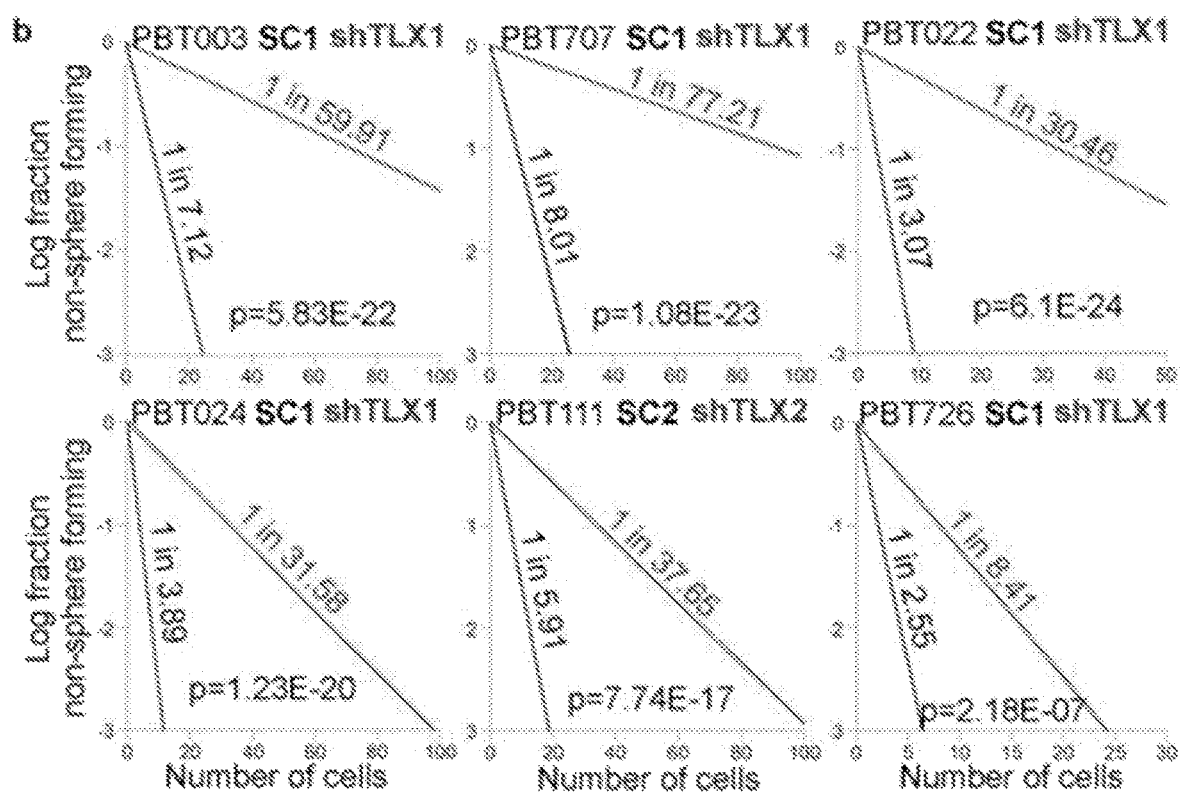
Figure 11:
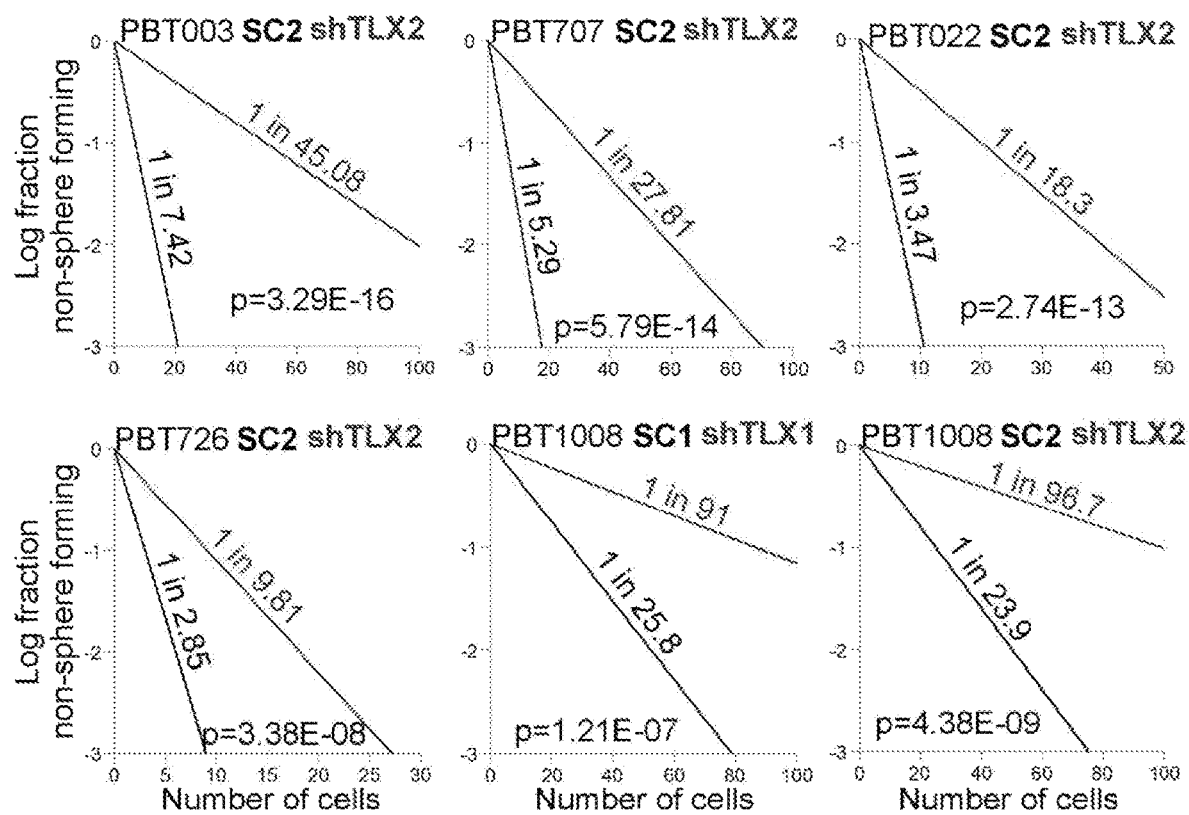
FIG. 11 is a series of graphs showing limiting dilution assay of GSCs. Limiting dilution assay (LDA) analysis of GSCs transduced with control RNAs (SC) or TLX shRNAs (shTLX), N=20.

The effect of knocking down TLX on the self-renewal ability of GSCs was determined using clonal analysis and limiting dilution assay. Knockdown of TLX dramatically reduced the self-renewal capacity of GSCs, as revealed by the sharply decreased sphere formation rate and stem cell frequency in TLX shRNA-transduced cells (FIG. 2 and FIG. 10, 11). Together, these results indicate that TLX is essential for maintaining GSC growth rate and self-renewal ability.

The dramatic inhibitory effect of TLX shRNAs on GSC growth and self-renewal in vitro prompted us to test whether knockdown of TLX affects the ability of GSCs to form tumors in vivo. Two GSC lines, PBT003 and PBT707 cells, were transduced with a lentiviral vector expressing a TLX shRNA and a GFP reporter. The transduced cells were transplanted into the frontal lobe of NSG mouse brains. Tumor formation and expansion by the TLX shRNA-transduced GSCs were compared with scrambled control RNA-transduced GSCs. Although the same number of GFP-positive cells was injected into each mouse, GFP fluorescence imaging revealed large masses of GFP-positive cells in brains transplanted with control RNA-transduced GSCs, but there was barely any GFP signal in brains transplanted with TLX shRNA-transduced GSCs (FIG. 3a). H&E staining showed that mice received control GSCs developed large tumor masses with typical infiltrative features of glioblastoma (FIG. 3b, c). Conversely, GSCs treated with TLX shRNAs did not form tumors, or only formed small lesions that were confined to the injection sites (FIG. 3b, c). Stereological measurement of tumor volumes confirmed significantly smaller tumors in brains transplanted with GSCs treated with TLX shRNA, compared to that in brains transplanted with control GSCs (FIG. 3d).

Kaplan-Meier survival analysis revealed that mice transplanted with TLX shRNA-transduced PBT003 cells had much better survival outcome compared to mice transplanted with scrambled control RNA-transduced cells (FIG. 3e). All mice that were transplanted with TLX shRNA-transduced PBT003 cells survived for more than 70 days post-transplant, and 40% of them survived beyond 80 days, whereas all mice that received PBT003 cells transduced with scrambled control RNA died before 60 days post-transplant. Similarly, all mice that received PBT707 cells transduced with the control RNA died before day 85 post-transplant, whereas most mice that received PBT707 cells transduced with the TLX shRNA survived beyond this point, and 40% survived beyond day 110 (FIG. 3e). Together, these results indicate that knockdown of TLX suppresses tumor growth and increases the lifespan of GSC-grafted mice.

Example 2

Knockdown of TLX In Vivo Suppresses Tumor Progression

Figure 4D:
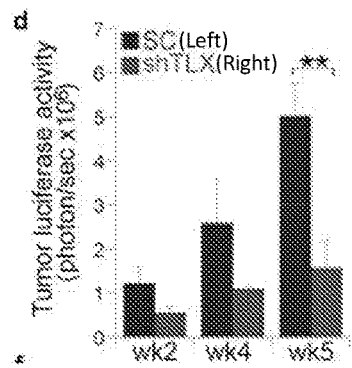

Knockdown down TLX in vivo was assayed for suppressive effects on the progression of human GSC-initiated tumors in a xenograft model. PBT003 cells were transduced with luciferase-expressing lentivirus, which allowed us to monitor tumor growth in vivo by bioluminescence imaging. The luciferase-expressing PBT003 cells were orthotopically transplanted into the frontal lobe of NSC mouse brains to establish tumors. One week after, mice were treated with scrambled control RNA or TLX shRNA-expressing lentivirus by intratumoral injection (FIG. 4a). Knockdown of TLX in PBT003 cells in vivo was confirmed by RT-PCR using human TLX-specific primers (FIG. 4b). Tumor formation was monitored using bioluminescence xenogen imaging (FIG. 4c). Mice received control RNA-expressing virus developed large tumors, whereas mice treated by TLX shRNA-expressing lentivirus had much smaller tumors (FIG. 4c, d). Bioluminescence intensity measurement showed a significant decrease of tumor signal in mice treated with TLX shRNA-expressing virus at 5 weeks after treatment (FIG. 4d).

Figure 4E:
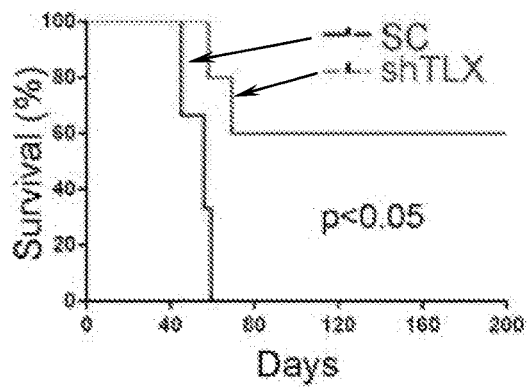

Moreover, PBT003-grafted mice treated with TLX shRNA-expressing virus had much better survival outcome compared to mice treated with scrambled control RNA (FIG. 4e). All mice that received control RNA died before day 60 post-treatment and the median survival was 56 days after viral treatment, whereas 60% of mice treated with TLX shRNA survived beyond 200 days post-treatment (FIG. 4e).

Figure 4F:
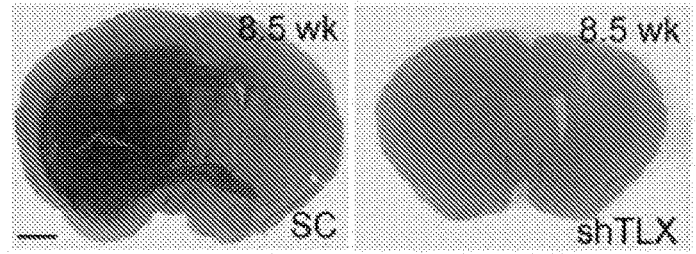
Figure 4G:
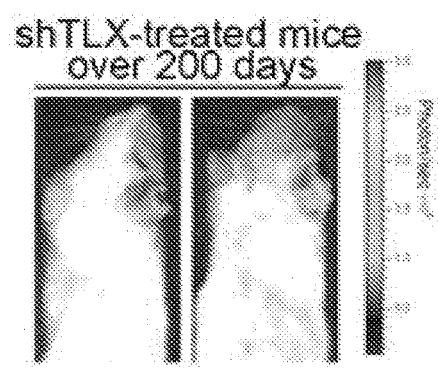
Figure 4H:

When mice in control group died, brain samples were collected for histological analysis. H&E staining revealed the development of big tumor mass and aggressive tumor invasion across the hemisphere in brains of control mice, whereas in brains of TLX shRNA-treated mice collected at the same time as the control mice, no tumor was detected or tumors were much smaller (FIG. 4f-h and data not shown). The tumors developed in control mice exhibited typical infiltrative features of glioblastoma (FIG. 4h). These results indicate that TLX shRNA-expressing virus suppressed the progression of established tumors and increased the lifespan of treated animals.

Figure 12A:
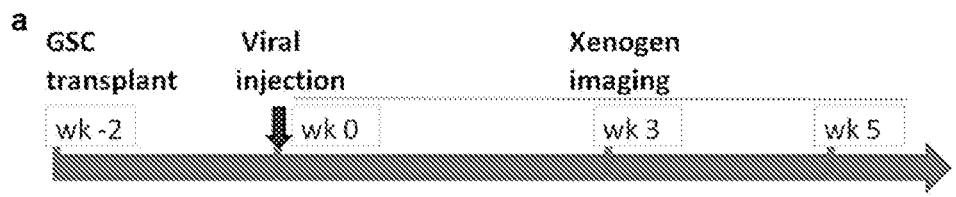
FIG. 12A-12C demonstrate that knockdown of TLX suppresses tumor progression.
Figure 12B:
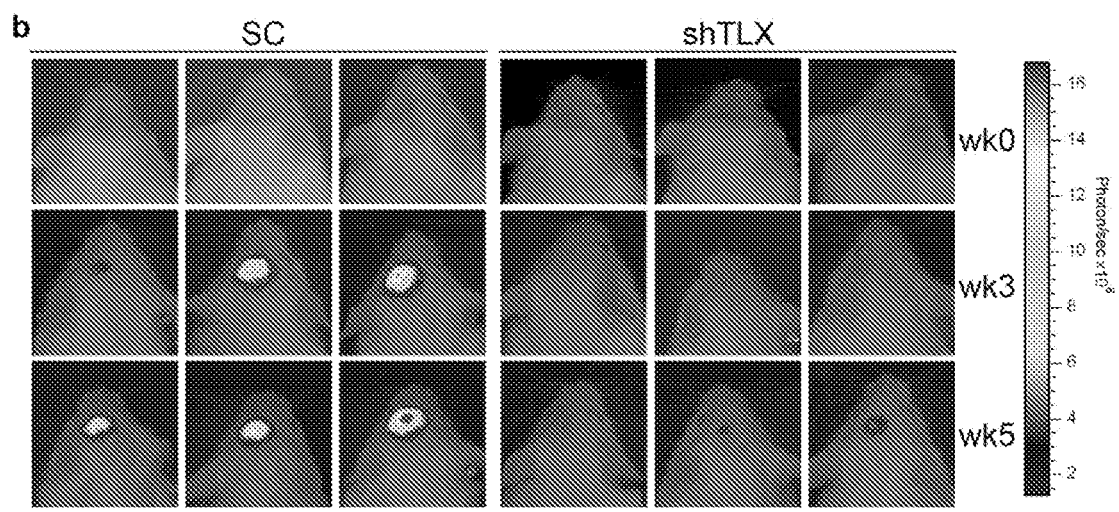
Figure 12C:
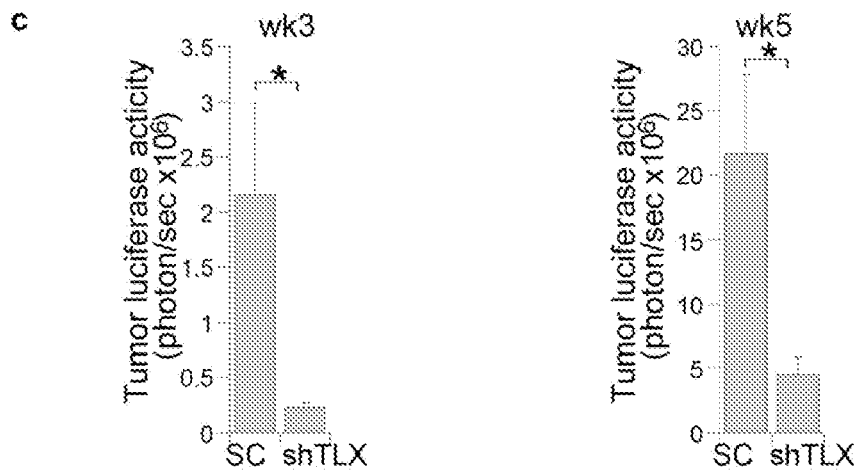

To determine the effect of TLX shRNA treatment on tumor progression at a different time point after tumor establishment, mice were treated with control RNA or TLX shRNA-expressing lentivirus two weeks after transplantation with luciferase reporter-bearing PBT003 cells (FIG. 12a). Bioluminescence imaging showed that TLX shRNA-expressing lentivirus dramatically inhibited tumor growth, compared to control virus (FIG. 12b). Bioluminescence intensity measurement showed a significant decrease of tumor size in TLX shRNA-expressing lentivirus-transduced mice, at 3 weeks and 5 weeks after treatment (FIG. 12c). These results demonstrate that treatment with TLX shRNA-expressing lentivirus suppressed the progression of established tumors and increased the lifespan of treated mice. The above results together strongly support the hypothesis that TLX could be an effective target to suppress human GSC self-renewal and tumorigenesis.

Example 3

The TLX siRNA Nanocomplex Inhibits GSC Tumor Progression

In addition to knocking down TLX using a TLX shRNA-expressing viral vector, the possibility of delivering TLX siRNA oligonucleotides was explored using a non-viral nanovector. The poly(amidoamine) PAMAM dendrimer of generation 5 (referred to as G5 thereafter) was chosen to deliver TLX siRNA because it has been shown to deliver siRNAs effectively by forming stable and compact nanoparticles with siRNAs and protect siRNAs from degradation, leading to efficient and long-term gene silencing[34,38]. The dendrimer-mediated delivery is also relatively safe without discernible toxicity[39].

Figure 5A:
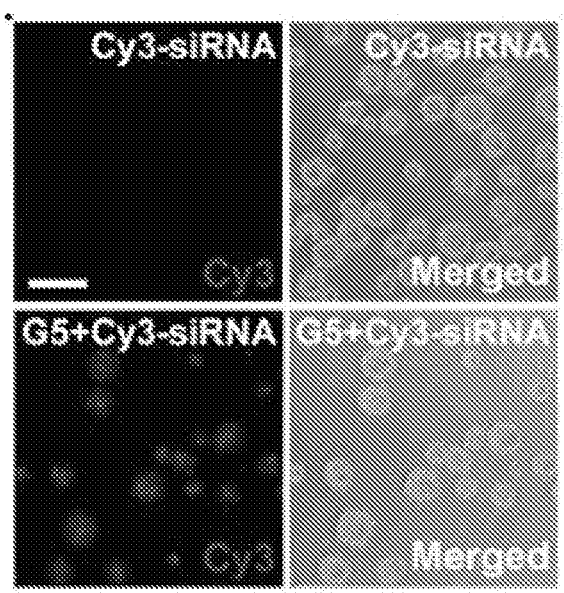
FIG. 5A-5F demonstrate effective dendrimer-based nanoparticle delivery of siRNA into GSCs.
Figure 5B:
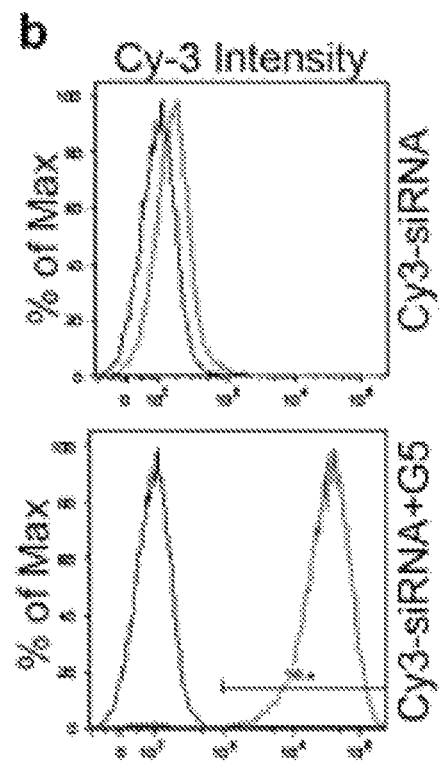

First it was tested whether the G5 dendrimer could form stable nanoparticles with siRNAs and deliver siRNAs into GSCs effectively. The G5 dendrimer was found to form stable complexes with TLX siRNA, as revealed by significant retardation on migration of the G5-siRNA complex at an N/P ratio of 1.0 or above in a gel shift assay (FIG. 13a). G5 and TLX siRNA readily formed stable and uniform nanoparticles with an average size slightly smaller than 100 nm in diameter at N/P ratio of 5 (FIG. 13b). Consistently, the G5-TLX siRNA complexes were able to protect siRNA from RNase-mediated degradation, whereas naked siRNA was rapidly degraded upon RNase digestion (FIG. 13c). When incubated with PBT003 cells, G5 efficiently delivered Cy3-labeled siRNA (Cy3-siRNA) into cells compared to Cy3-siRNA alone control (FIG. 5a). The cellular uptake of G5 delivered Cy3-siRNA was further confirmed by flow cytometry analysis (FIG. 5b).

Figure 5C:
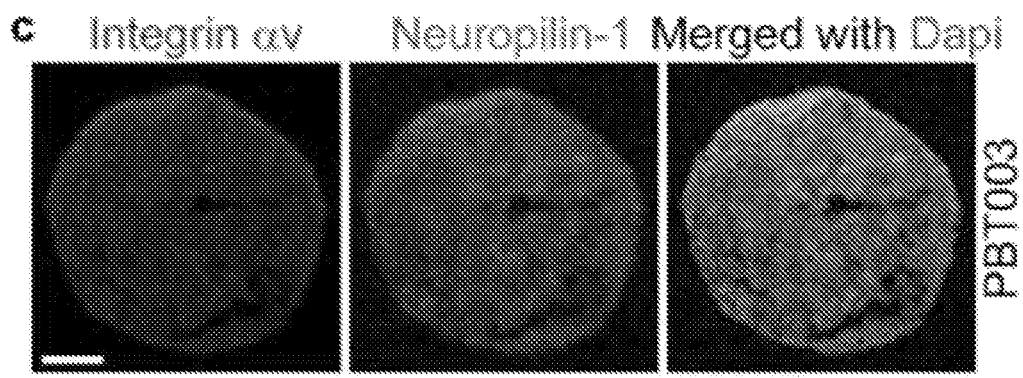
Figure 5D:
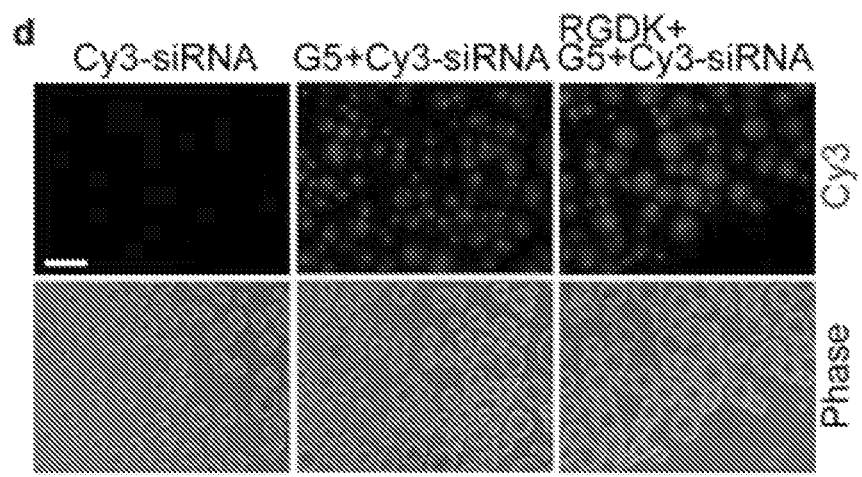

To achieve tumor cell-targeted delivery, the dendrimer-TLX siRNA nanoparticles were coated with a targeting peptide that contains the dual targeting RGDK motif[40]. The RGD motif in the RGDK peptide directs tumor-specific homing through integrin-dependent binding to tumor cells specifically[41], while the RXXK motif promotes cell and tissue penetration through interaction with neuropilin-1[41-44]. Both integrin αv and neuropilin-1 were expressed on the surface of PBT003 cells (FIG. 5c). Decoration of the TLX siRNA-G5 complexes with the RGDK peptide led to the formation of nanoparticles with a size around 100 nm in diameter (FIG. 13d), within a size range required for effective cellular uptake. Coating the G5 dendrimer with the RGDK peptide enhanced the uptake of Cy3-siRNA into GSCs, compared to the uptake of G5 dendrimer-delivered Cy3-siRNA or Cy3-siRNA alone, as revealed by increased intensity of intracellular Cy3 fluorescence (FIG. 5d).

Figures 5E, 5F:
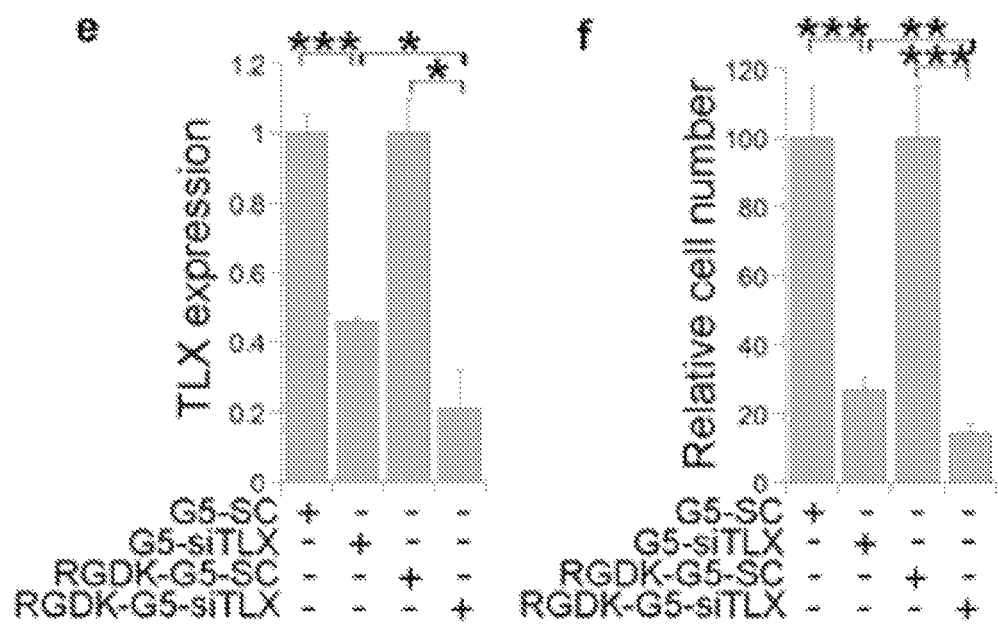

PBT003 cells were treated with the G5 dendrimer-TLX siRNA nanocomplex, with or without RGDK coating. RT-PCR confirmed efficient TLX knockdown by G5 dendrimer-delivered TLX siRNA. Treatment with RGDK-coated G5 dendrimer-TLX siRNA nanocomplex induced even more potent TLX knockdown, presumably due to better cell penetration (FIG. 5e). Compared to control RNA, TLX siRNA delivered by G5 dramatically reduced the growth of PBT003 cells, and TLX siRNA delivered by RGDK-coated G5 dendrimer suppressed the growth of PBT003 cells even more (FIG. 5f). Together, these results demonstrated that RGDK-coated dendrimer-TLX siRNA complex efficiently knocked down TLX expression in GSCs and suppressed GSC growth potently.

Figure 6A:
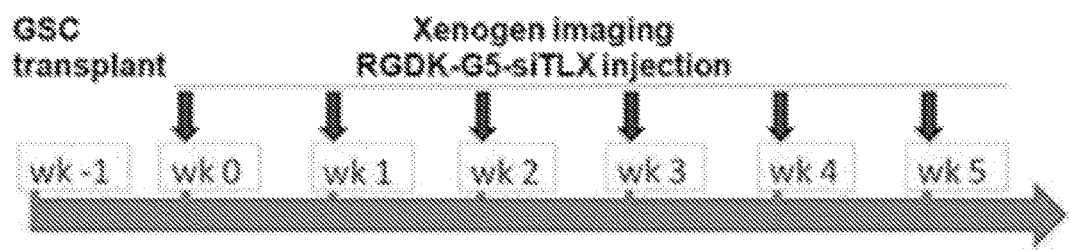
FIG. 6A-6G demonstrate that treatment with the RGDK coated G5 dendrimer-siTLX complex led to reduced tumor growth of GSC derived GBM and increased mouse survival.
Figures 6B, 6C:
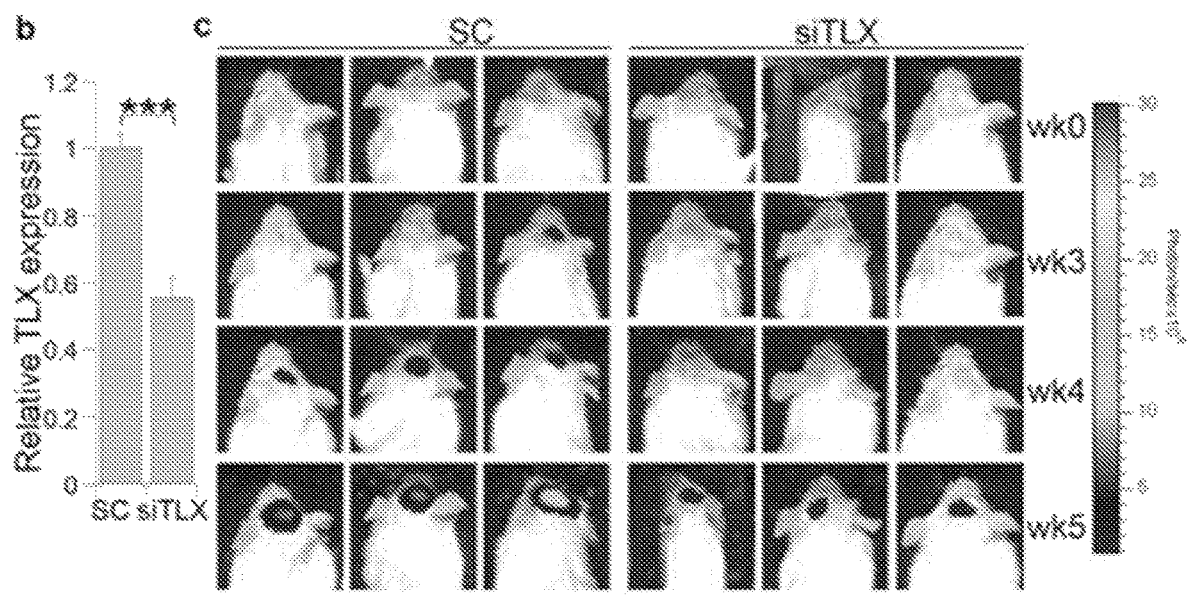
Figure 6D:
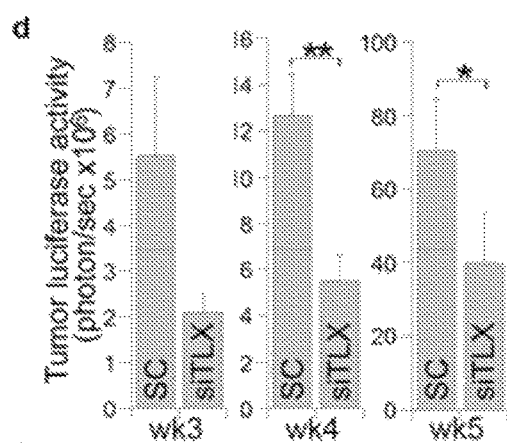
Figure 6E:
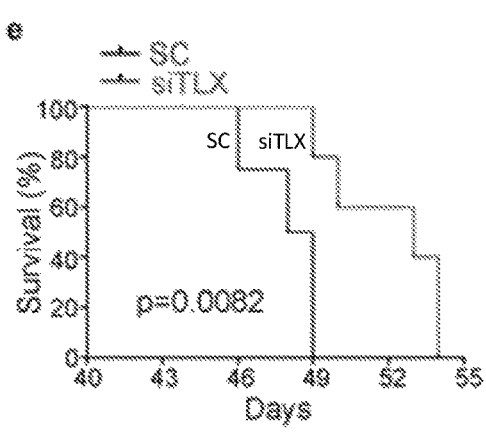
Figure 6F:
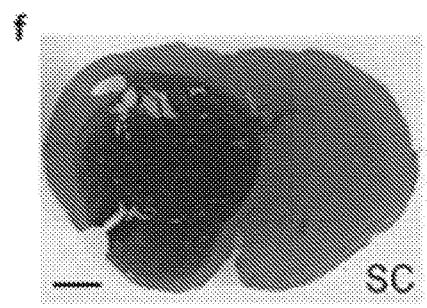
Figure 6G:
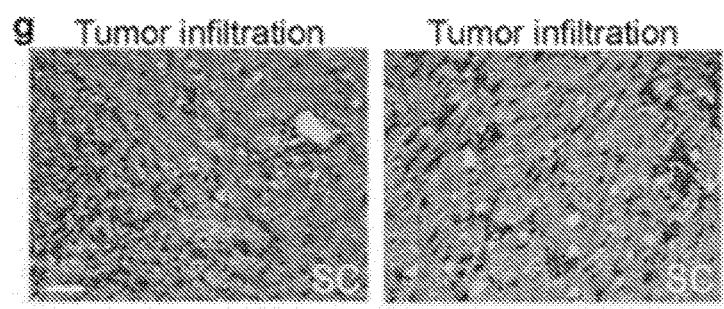
Figure 14:
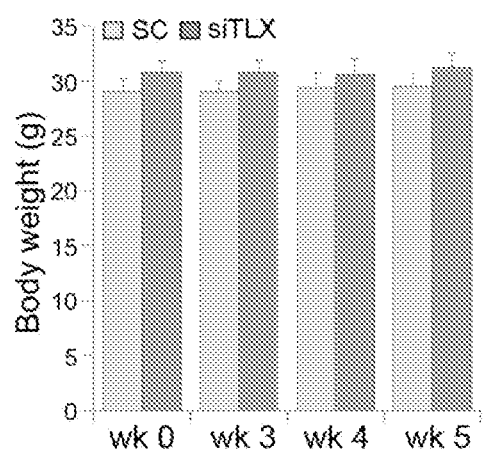
FIG. 14 is a graph of weight analysis of TLX siRNA nanocomplex-treated mice. Measurement of mouse body weight before and after treatment of tumor bearing NSG mice by RGDK-G5-TLX siRNA complex or RGDK-G5-SC RNA complex. N=7, error bars are s.d. of the mean.

Next it was investigated whether TLX siRNA delivered by RGDK-coated dendrimer could suppress tumor progression in a human GSC-induced xenograft tumor model. PBT003 cells with a luciferase reporter were orthotopically transplanted into the frontal lobe of NSG mouse brains to establish tumors. One week after transplantation, mice were treated with the RGDK-coated G5-TLX siRNA complex or RGDK-coated G5-control RNA complex by intratumoral injection (FIG. 6a). The in vivo TLX knockdown was confirmed by RT-PCR using human TLX-specific primers (FIG. 6b). No obvious body weight loss was resulted from surgery or treatment of the nanoparticles before tumor-induced symptoms developed (FIG. 14). Bioluminescence imaging revealed that mice treated with the RGDK-coated G5-TLX siRNA complex had dramatically reduced tumor growth compared to control mice (FIG. 6c). Bioluminescence intensity measurement confirmed that the tumor signals in RGDK-coated G5-TLX siRNA complex treated mice were significantly decreased compared to that in control mice (FIG. 6d). Moreover, treatment with the RGDK-coated G5-TLX siRNA complex significantly extended the lifespan of GSC-grafted mice (FIG. 6e). Tumors developed in control mice exhibited typical infiltrative features of glioblastoma (FIG. 6f, g), whereas mice treated with the RGDK-G5-TLX siRNA nanoparticles developed smaller tumor. These results indicate that RGDK-coated dendrimer-delivered TLX siRNA could effectively decrease tumor growth and increase the lifespan of tumor-bearing mice.

Example 4

TET3 Suppresses GSC Growth, Self-Renewal, and Tumorigenicity

Figure 15A:
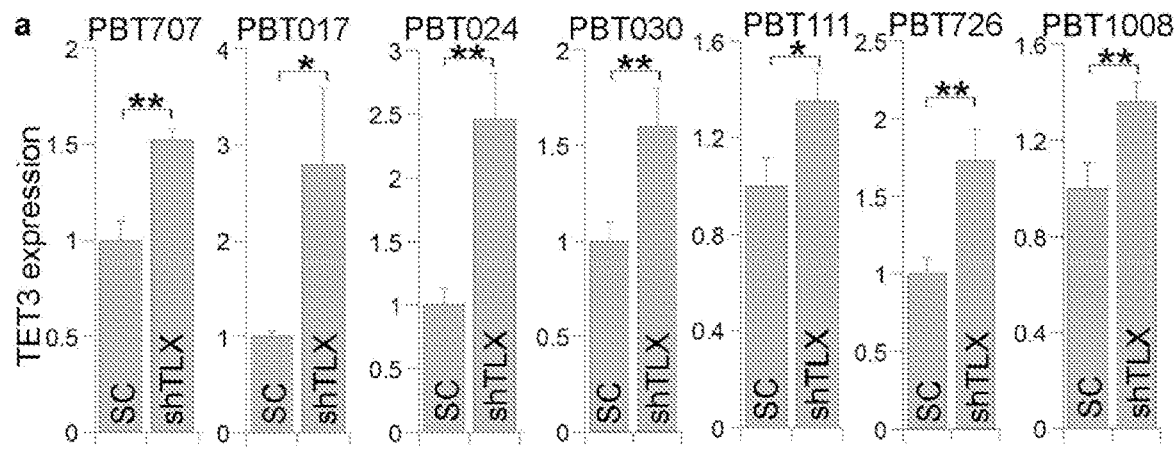
FIG. 15A-15D demonstrate up-regulation of TET3 in TLX knockdown GSCs.
Figure 16:
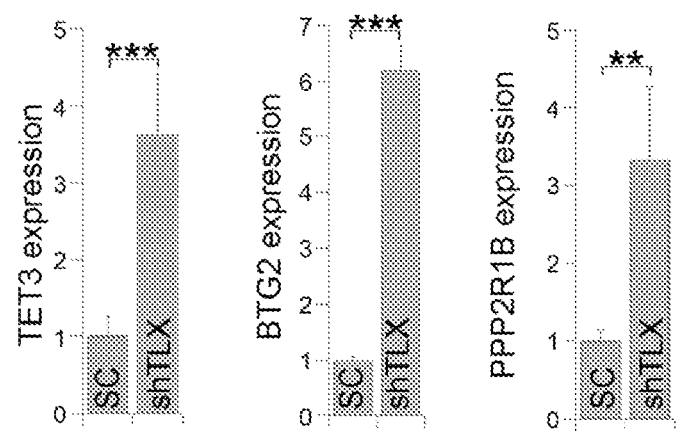
FIG. 16 is a graph showing regulation of TET3 and targets in TLX knockdown GSCs in vivo. RT-PCR analysis of TET3, BTG2, and PPP2R1B in PBT003-grafted brain tumors treated with scrambled control (SC) or TLX shRNA (shTLX) in NSG mice. N=3, error bars are s.e. of the mean. p<0.01, *p<0.001 by Student's t-test.

To investigate the mechanism by which TLX controls the growth, self-renewal, and tumorigenesis of GSCs, microarray analysis was performed to compare gene expression profiles in control and TLX shRNA-treated GSCs. TLX was identified in the down-regulated gene cohort, whereas the cyclin-dependent kinase inhibitor p21, a known downstream target that is repressed by TLX[45], was among the up-regulated genes, confirming the effectiveness of TLX knockdown in TLX shRNA-treated cells. Several potential downstream targets that were not associated with TLX before were identified by array analysis (FIG. 7a). Specifically, the expression of TET3, TDG, and DICER1 genes were up-regulated and the expression of ID3, ID4, and MBD2 genes were down regulated in TLX-shRNA treated PBT003 cells (FIG. 7a). The regulation of TET3 by TLX knockdown was confirmed in PBT003 cells and other GSC lines by RT-PCR (FIG. 7b, c and FIG. 15a). Up-regulation of TET3 upon TLX knockdown was also confirmed in PBT003-grafted brain tumors from NSG mice treated with virus expressing TLX shRNA compared to that in tumors from mice treated with control virus (FIG. 16). Of note, TET3, TDG, and MBD2 are all involved in DNA methylation modification, suggesting epigenetic regulation of DNA methylation may be an important downstream event of knocking down TLX in GSCs.

Figure 15B:
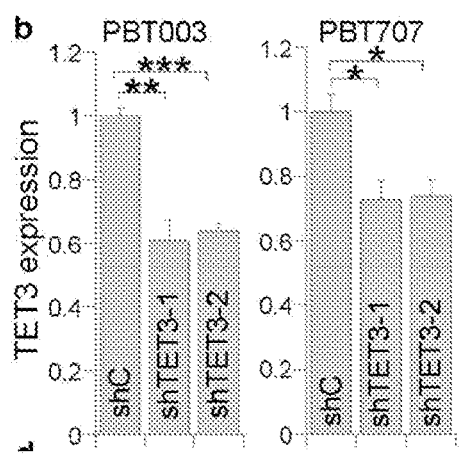

Recent studies showed that TET2 and TET3 act downstream of the oncogenic microRNA 22 to suppress stemness and metastasis of breast cancer[26]. However, the role of TET3 in GSC growth and self-renewal remains unknown. Based on the negative regulation of TET3 expression by TLX, it was hypothesized that TET3 could function as a tumor suppressor to control GSC growth and self-renewal. To test this hypothesis, two shRNAs were designed to knockdown TET3 in GSCs. Knockdown of TET3 was confirmed in PBT003 and PBT707 cells (FIG. 15b). PBT003 cells expressing TET3 shRNAs showed increased cell growth compared to control RNA-treated cells (FIG. 7d). Consistent with increased cell growth, PBT003 cells with TET3 knockdown also showed increased sphere formation rate compared to control cells (FIG. 7e). The increased cell growth and sphere formation rate after knockdown of TET3 were also observed in PBT707 cells (FIG. 7d, e). Taken together, these results demonstrated that knockdown of TET3 increased GSC growth and self-renewal.

Figure 7G:
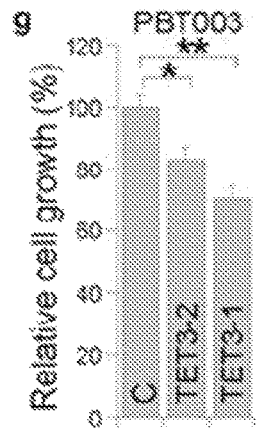
Figure 7G:
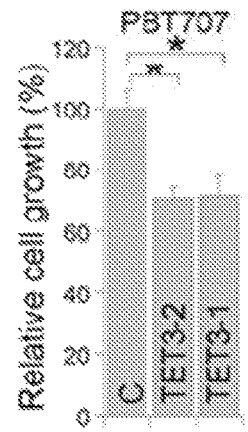
Figure 7H:
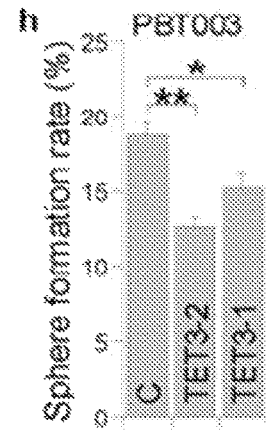
Figure 7H:
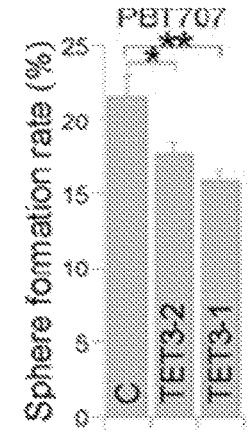
Figure 7I:
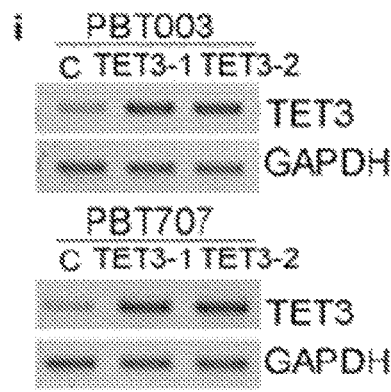
Figure 15C:
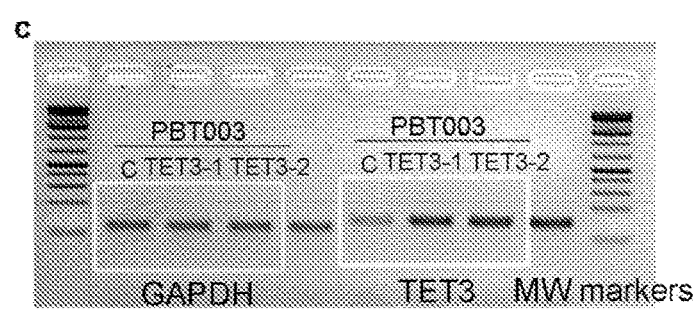
Figure 15D:
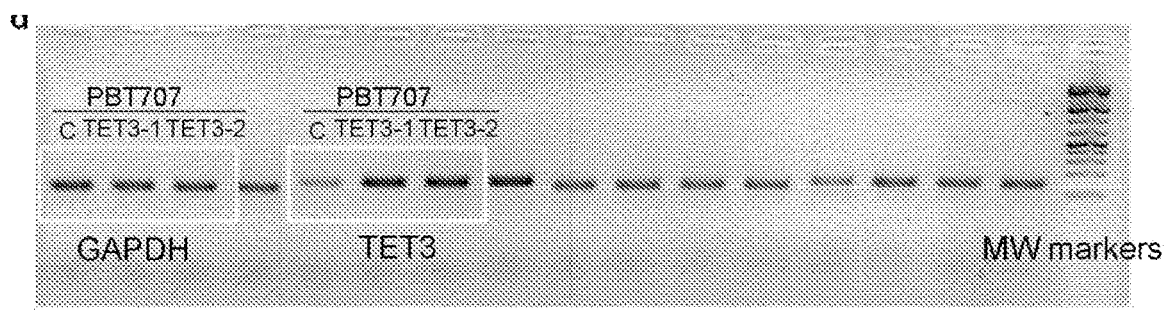

To investigate if TET3 is sufficient to regulate the growth and self-renewal of GSC, the effect of TET3 overexpression in GSCs was tested. Human TET3 gene (GenBank Accession No. NM_001287491.1), TET3-1 (GenBank Accession No. NM_001287491.1, with the CXXC domain) or TET3-2 (GenBank Accession No. NM_144993.1, without the CXXC domain) (FIG. 7f) was cloned into a lentivirus vector. Both TET3-1 and TET3-2 constructs contain the dioxygenase domain that is present in all TET proteins. Overexpression of TET3-1 and TET3-2 was confirmed by RT-PCR in PBT003 and PBT707 cells transduced with the TET3-expressing virus (FIG. 7i and FIGS. 15c & 15d). Overexpressing either TET3-1 or TET3-2 reduced the growth of both PBT003 and PBT707 cells (FIG. 7g). Consistent with decreased cell growth, PBT003 and PBT707 cells overexpressing TET3-1 or TET3-2 also showed decreased sphere formation rate compared to control cells (FIG. 7h). These results together indicate that TET3 inhibits GSC growth and self-renewal.

Figure 7J:
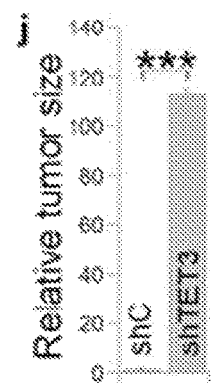
Figure 7K:
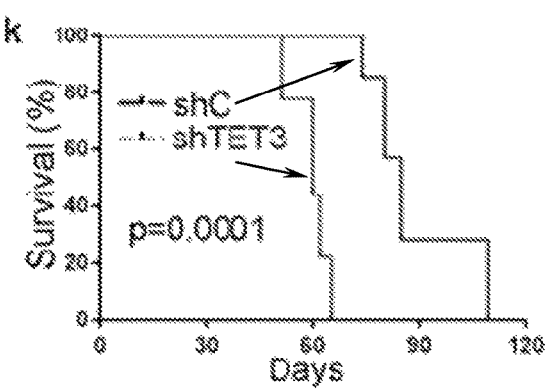

To investigate if TET3 regulates GSC tumorigenicity, PBT003 cells were transduced with a lentiviral vector expressing a TET3 shRNA or a control shRNA. The transduced cells were then transplanted into the frontal lobe in brains of immunodeficient NSG mice. Tumor formation and expansion by the TET3 shRNA-treated GSCs were compared to that by control RNA-treated GSCs that were maintained under identical conditions. Stereological measurement of tumor volumes confirmed the development of significantly larger tumors in brains transplanted with GSCs treated with TET3 shRNA, compared to that in brains transplanted with control GSCs (FIG. 7j). Kaplan-Meier survival analysis revealed that mice transplanted with TET3 shRNA-transduced PBT003 cells had significantly shorter survival compared to mice transplanted with control RNA-transduced cells (FIG. 7k). Together, these results indicate that knockdown of TET3 increases tumor progression and decreases the lifespan of GSC-grafted mice, in a manner opposite to knockdown of TLX.

It is shown that knockdown of TLX expression dramatically inhibits human GSC tumorigenicity. Treatment of human GSC-grafted mice with viral vector-delivered TLX shRNA or nanovector-delivered TLX siRNA inhibits tumor development and prolongs survival substantially. Moreover, TET3 has been identified as a potent tumor suppressor downstream of TLX to regulate the growth and self-renewal in GSCs.

Example 5

TET3 Acts Downstream of TLX to Regulate GSC Self-Renewal

Figures 8A, 8B:
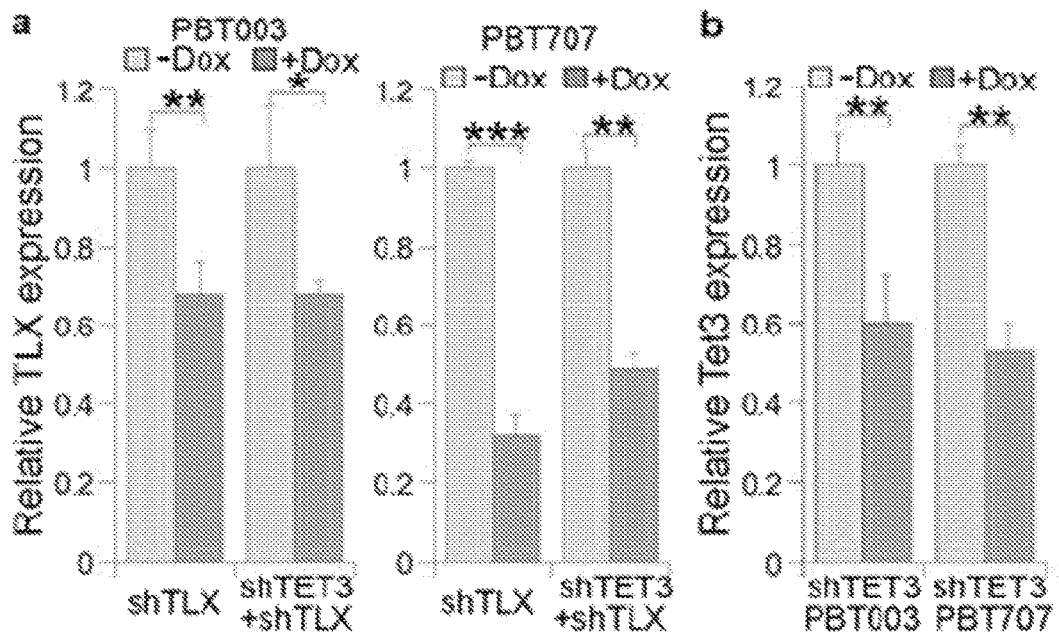
FIG. 8A-8K demonstrate that TET3 acts downstream of TLX to regulate GSC growth and self-renewal.
Figures 8C, 8D:
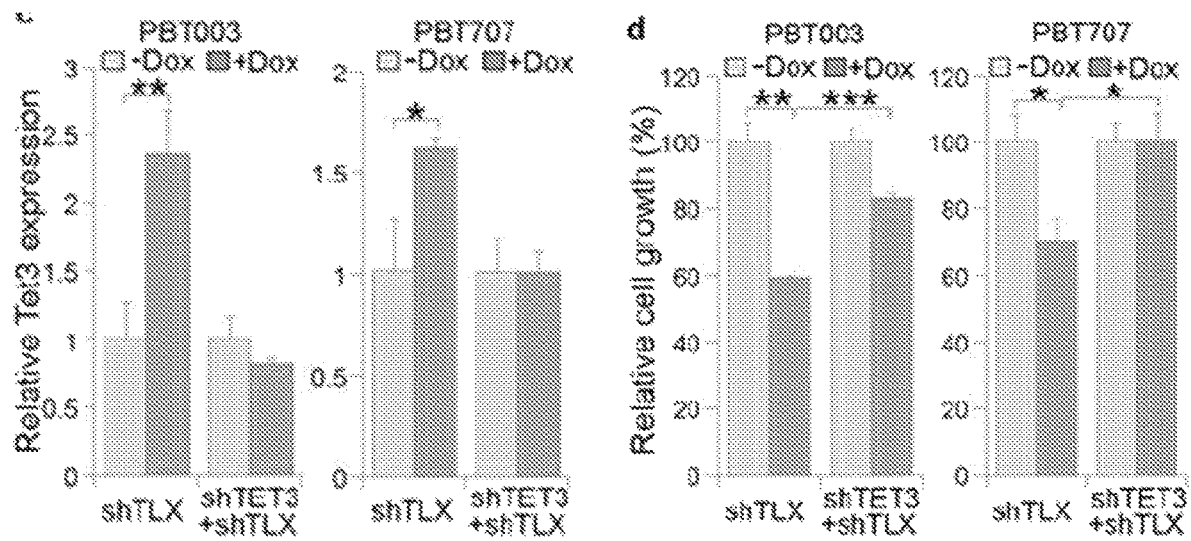

To test whether TET3 acts downstream of TLX to regulate GSC growth and self-renewal, an inducible system to double knock down TLX and TET3 was established. PBT003 and PBT707 cells were transduced with lentivirus that expresses doxycycline (dox)-inducible TLX shRNA together with a puromycin-resistant reporter gene. After puromycin selection, the stably transduced cells were then transduced with lentivirus expressing dox-inducible TET3 shRNA. Induced knockdown of TLX and TET3 was confirmed in dox-treated PBT003 and PBT707 cells transduced with lentivirus expressing dox-inducible TLX shRNA (FIG. 8a) or TET3 shRNA (FIG. 8b). As expected, the expression of TET3 was up-regulated after dox-induced knockdown of TLX (FIG. 8c). Dox-induced TET3 knockdown reversed the expression of TET3 to control levels in cells expressing both inducible TLX shRNA and inducible TET3 shRNA (FIG. 8c).

Figures 8E, 8F:
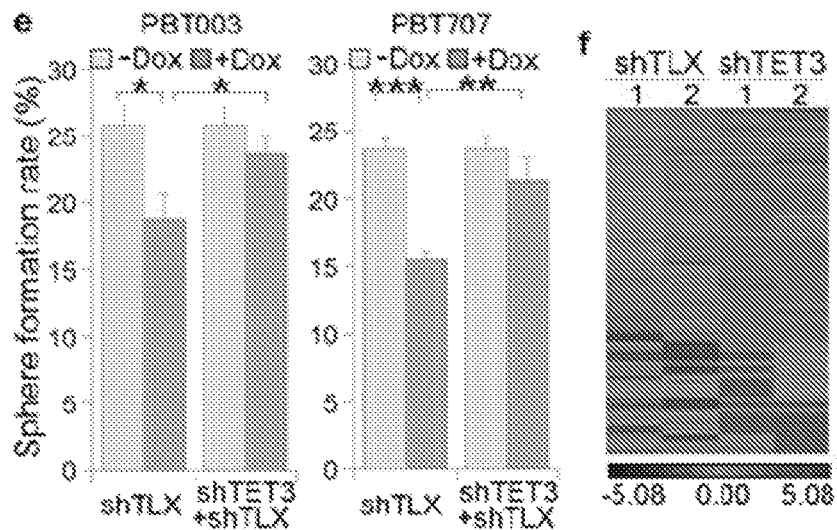

It further tested whether inducible TET3 knockdown could rescue the inhibitory effect of inducible TLX knockdown on GSC growth and self-renewal. After dox induction, the growth of PBT003 and PBT707 cells expressing inducible TLX shRNA was reduced when compared to non-induced cells (FIG. 8d). The decreased cell growth resulted from induced TLX knockdown was rescued substantially by induced TET3 knockdown in both PBT003 and PBT707 cells (FIG. 8d). The reduced self-renewal of PBT003 and PBT707 cells resulted from dox-induced TLX knockdown was also rescued by dox-induced TET3 knockdown (FIG. 8e). These results together indicate that TET3 is a critical downstream target of TLX in regulating GSC growth and self-renewal.

Figure 17A:
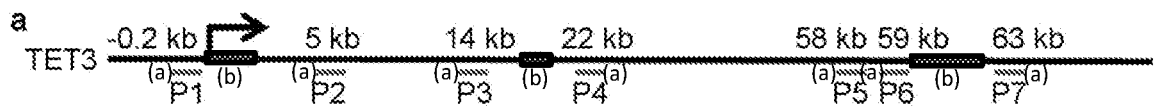
FIG. 17A-17C demonstrate that TLX binds to TET3 promoter and proximal introns in GSCs.
Figure 17B:
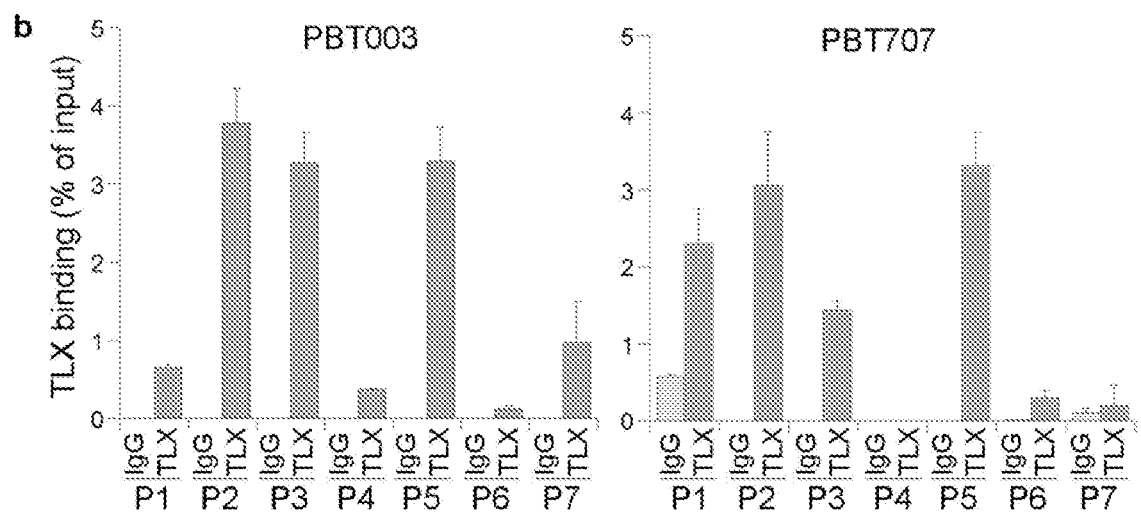
Figure 17C:
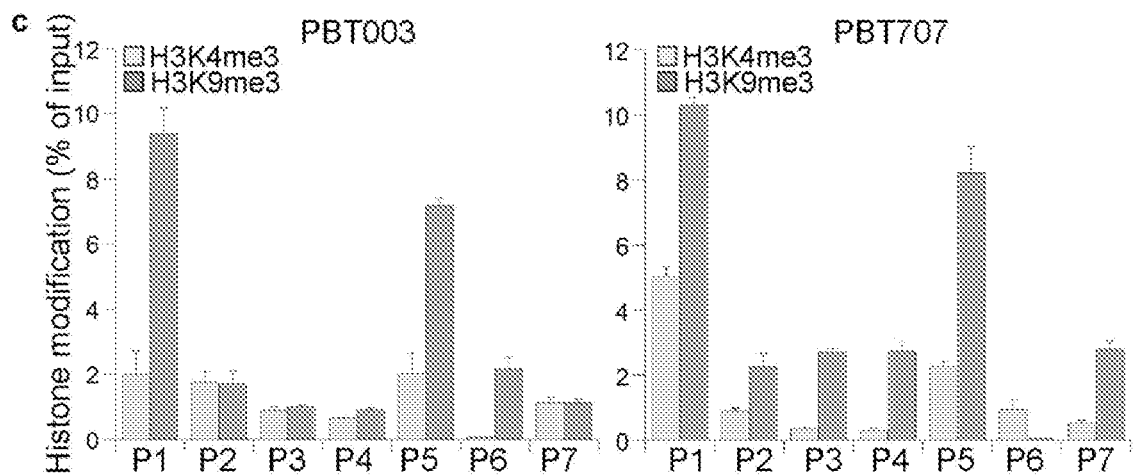

The inverse correlation between TET3 and TLX expression in TLX knockdown GSCs led us to hypothesize that TLX, a known transcription factor that usually works as a transcriptional repressor[45], could repress TET3 expression by directly binding to the promoter of the TET3 gene. Chromatin immunoprecipitation (ChIP) analysis using a TLX-specific antibody revealed that TLX bound to the promoter and proximal intron regions of TET3 containing the putative TLX binding sites in both PBT003 and PBT707 cells (FIG. 17a, 17b). At position 1 (P1, around the promoter region) and position 5 (P5, intron 2), the binding sites of TLX was associated with a higher level of repressive histone mark H3K9me3 than that of active histone mark H3K4me3 in both PBT003 and PBT707 cells (FIG. 17c). This data suggest that TLX could regulate the transcription of TET3 by directly binding to regulatory regions of the TET3 gene.

To identify downstream targets of TET3 in GSCs, microarray analysis was performed. The gene expression profile of PBT003 cells treated with TET3 shRNA-expressing lentivirus was compared to PBT003 cells expressing control shRNA. The genes down-regulated in TET3 shRNA-treated cells were shown in blue, whereas those up-regulated in TET3 shRNA-treated cells were shown in red. Data sets from microarray analysis of PBT003 cells transduced with TLX shRNA or control RNA were included for comparison. Among the differentially expressed genes, an inverse correlation in gene expression was observed in TLX knockdown cells and TET3 knockdown cells (FIG. 8f), consistent with the hypothesis that TLX represses TET3 expression. Specifically, genes related to tumor suppressive function, including BTG2, TUSC1, BAK1, LATS2, FZD6, and PPP2R1B, were up-regulated in TLX knockdown cells, but down-regulated in TET3 knockdown cells (FIG. 8g and FIG. 18), suggesting that the TLX-TET3 regulatory cascade could regulate the growth and self-renewal of GSCs through regulating these downstream tumor suppressors.

Figures 8G, 8H, 8I:
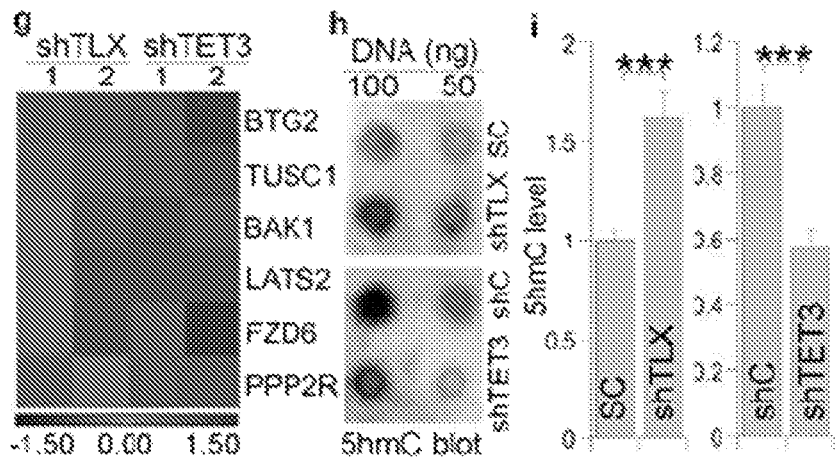

Because TET3 is a dioxygenase that converts 5mC to 5hmC, it was next tested whether the TLX-TET3 regulatory cascade could regulate 5hmC level in GSCs. Dot blot analysis using a 5hmC-specific antibody revealed increased 5hmC level upon TLX knockdown, but decreased 5hmC level upon TET3 knockdown in PBT003 cells (FIG. 8h, j).

Figures 8J, 8K:
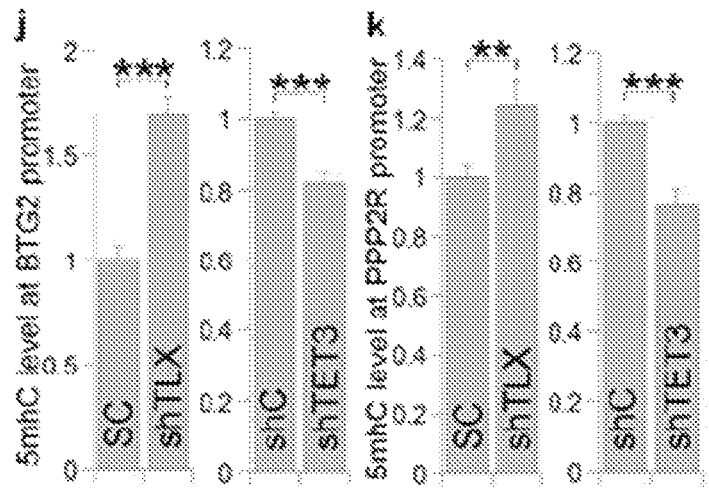
Figure 18A:
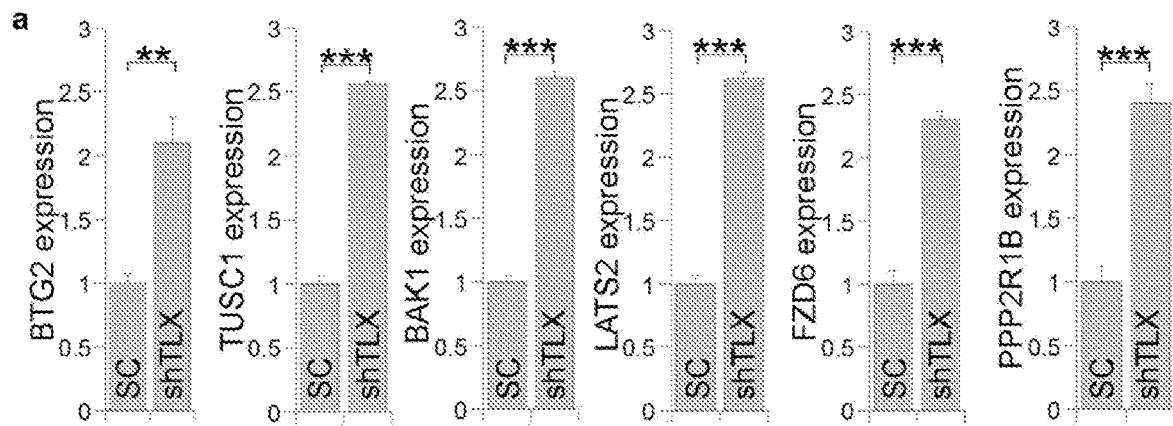
FIGS. 18A and 18B demonstrate that the TLX-TET3 axis regulates the expression of tumor suppressor genes.
Figure 18B:
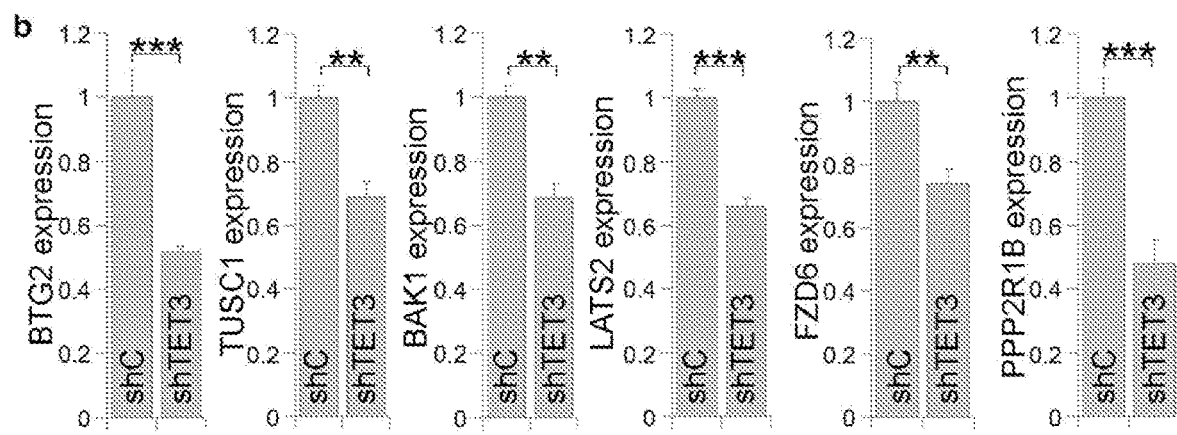

DNA microarray analyses have identified several tumor suppressors as candidate downstream targets of TLX and TET3, including BTG2 and PPP2R1B (FIG. 8g), which were also up-regulated upon TLX knockdown in PBT003-grafted brain tumors in NSG mice (FIG. 16). To test whether the TLX-TET3 cascade regulates 5hmC level at the promoter of these potential downstream targets, hydroxymethylated DNA immunoprecipitation (hMeDIP)-qPCR analysis was performed. The 5hmC levels at the promoter region of BTG2 and PPP2R1B genes were significantly increased in PBT003 cells transduced with TLX shRNA, compared to control cells (FIG. 8j, k), consistent with the elevated expression of these genes in TLX knockdown PBT003 cells (FIG. 18a). In contrast, knockdown of TET3 reduced 5hmC level at the promoter region of BTG2 and PPP2R1B (FIG. 8j, k), consistent with the reduced expression of these genes in TET3 knockdown PBT003 cells (FIG. 18b). These results indicate that the TLX-TET3 regulatory cascade could regulate the expression of downstream tumor suppressor genes by controlling the 5hmC level at their promoter regions.

A role for TLX in glioblastoma development has been proposed in studies using mouse models[14,46]. A recent study by lineage tracing demonstrated that TLX regulates the self-renewal of brain tumor stem cells in mouse brains[47]. Evidence described here shows that targeting TLX in GSCs derived from human glioblastoma patients efficiently inhibited the growth, self-renewal and tumorigenicity of GSCs in vitro and in vivo. The inhibitory effects of growth and self-renewal by TLX suppression were seen in all GSC lines tested, including classical, mesenchymal, and proneural subtypes. These results suggest a general role for TLX in maintaining human GSC self-renewal, independent of glioblastoma subtypes. Treatment of human GSC-grafted mice with TLX small interfering RNA dramatically reduced tumor growth and significantly prolonged survival of GSC-grafted mice. Targeting TLX in vivo is effective at different time points, both one week and two weeks after tumor establishment. Knocking down TLX in vivo provided proof-of-concept that targeting TLX is effective to suppress the progression of human GSC-derived tumors.

The knowledge on how TLX controls the self-renewal and tumorigenesis of human GSC is limited. The cyclin-dependent kinase inhibitor p21 is a known downstream target of TLX that can control cell cycle arrest. Microarray array data described herein confirms that p21 is up-regulated upon TLX knockdown as previously reported by us and others[45,47]. Up-regulation of reported tumor suppressor genes, such as CDKN2A, CDKN2B, and PML, and factors for neuronal differentiation, such as SMARCC1 and DLX2, was not seen in microarray analysis. This may be due to the difference of human samples and mouse samples used for analyses. Human GSCs after TLX knockdown were investigated here, whereas prior findings examined the expression of genes altered by TLX knockout using RNAs isolated from tumor tissues of a mouse tumor model[47].

Mammalian TET3 exists in isoforms either containing the CXXC domain (TET3-1) or not containing the CXXC domain (TET3-2)[48], with estimated transcript size of 11.6 kb and 10.9 kb, respectively. Of interest, the TET3-2 isoform that lack the CXXC domain is the major isoform in the brain and retina[48,49]. While the TET3-1 isoform can bind to DNA using its amino-terminal CXXC domain[50], the TET3-2 form can also bind to DNA, presumably through its interacting proteins, including the CXXC domain containing protein CXXC4[48], and transcription factors, such as REST[49]. It is clear that the TET3-2 isoform that lacks the CXXC domain is able to induce 5hmC formation and gene expression[49].

Therefore, it is not surprising that the CXXC domain of TET3 seems dispensable for the effect on inhibition of GSC growth and self-renewal as described herein.

As described herein TET3 is a potential tumor suppressor that acts downstream of TLX to regulate GSC growth and self-renewal. TLX represents the first transcription factor that has been identified to regulate TET3 expression. TET3 is a member of the TET family proteins that are known to be epigenetic regulators that control DNA demethylation. Although growing evidence showing that epigenetic regulation plays an important role in cancer development, knowledge on the role of TET family members, especially TET3, in tumor development is rather limited. As described herein TET3 suppresses the growth and self-renewal of GSCs downstream of TLX. Data presented defines the role of TET3 in cancer stem cells and in glioblastoma and provides additional targets for therapeutics. Decreased 5hmC level has been observed in human cancers, including malignant glioma[18-20], but the underling mechanisms were previously unknown. It is shown that TLX represses TET3 expression in GSCs. This finding may explain the decreased 5hmC level in glioblastoma. Furthermore, additional tumor suppressors, including BTG2, TUSC1, BAK1, LATS2, FZD6, and PPP2R1B, were identified as common targets of TLX and TET3. These tumor suppressors could be potential targets of the TLX-TET3 regulatory axis in GSCs that are worthy of further studies.

A potential clinical significance of this finding is derived from the ability of knocking down TLX in GSCs via lentivirus-delivered shRNA or nanoparticle-delivered siRNA to compromise the self-renewal and tumor formation potential of GSCs in vivo. Data presented herein demonstrate that TLX knockdown inhibited tumor initiation and progression from human GSCs in a xenografted tumor model and increased the survival of grafted animals substantially. Glioblastoma is highly aggressive brain tumor with a short life expectancy of a little over a year after diagnosis, and patient survival is only marginally increased by current therapies. The small RNA approach to knock down TLX in GSCs has the potential to help improve the outcome and survival of glioblastoma patients.

Knockdown of TLX using dendrimer nanovector-delivered synthetic siRNAs or virally expressed short hairpin RNAs (shRNAs) was shown to dramatically reduce GSC growth and self-renewal. By transplanting TLX shRNA-transduced GSCs into immunodeficient NOD SCID Gamma (NSG) mice, it was shown that knockdown of TLX expression leads to almost complete failure of GSCs to develop tumors in transplanted mouse brains. Furthermore, intratumoral delivery of TLX siRNAs using a dendrimer nanovector or TLX shRNAs using a viral vector dramatically inhibits GSC-induced tumorigenesis and significantly prolongs the lifespan of GSC-grafted animals. Moreover, TET3 was identified as a critical TLX downstream target and it was demonstrated that TET3 functions downstream of TLX to inhibit GSC growth and self-renewal.

Small RNAs have gained increasing attention as candidate agents for therapies. However, the success of therapeutic application of small RNAs depends on efficient intracellular delivery. Safe and efficient small RNA delivery is in urgent need. An efficient system of siRNA delivery into GSCs using polycationic PAMAM dendrimer G5 or alternatives and variants thereof is described herein. This dendrimer has been shown to compact small RNAs into nanoparticles and protect RNAs from enzymatic degradation, therefore providing an efficient delivery means for introducing small RNAs into GSCs. Moreover, coating the dendrimer-siRNA nanoparticles with the tumor-homing RGDK peptide allows tumor-specific targeting. Here it is shown that GSCs express both integrin αv and neuropilin-1. Furthermore, it is demonstrated that the RGDK-coated dendrimer-TLX siRNA nanoparticles were able to deliver TLX siRNAs into GSCs efficiently and exert potent gene knockdown and growth inhibitory effect. When delivered in vivo, the RGDK-coated dendrimer-TLX siRNA nanocomplex inhibited the growth of human GSC-initiated tumors. Moreover, treatment of the RGDK-coated G5-TLX siRNA complex significantly extended the lifespan of tumor-bearing mice, increasing the median survival from 48 days after the first treatment to 53 days, corresponding to about 7-month prolonged survival in patients. Similarly mild but significant increase of survival has also been observed by targeting other important GBM targets[51,52].

Example 6

Small Molecule Activators of TLX

Figure 19A:
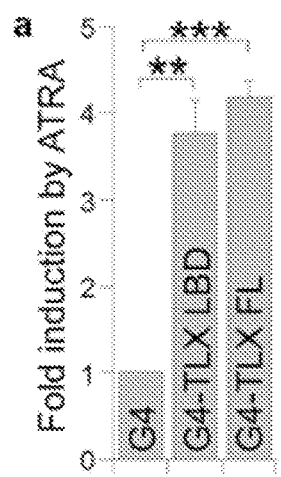
FIG. 19A-19C demonstrate that ATRA binds to the TLX ligand binding domain (LBD) and activates TLX.
Figure 19B:
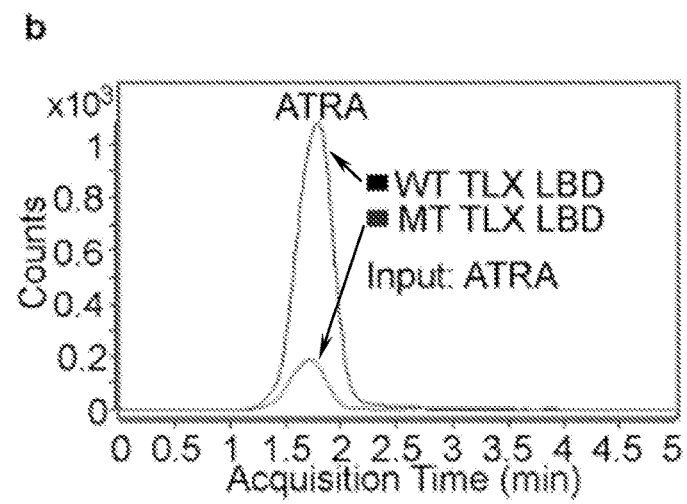
Figure 19C:
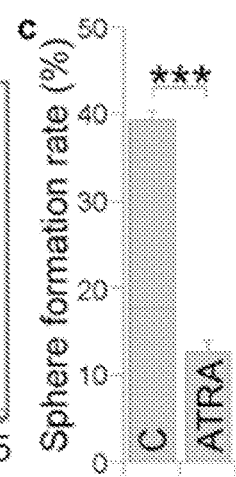

Known nuclear receptor ligands were assayed for their ability to activate TLX. It was discovered that all-trans retinoic acid (ATRA) can activate TLX through direct binding to the ligand binding domain of TLX (see FIG. 19A-19C). TLX functions as a transcriptional repressor to maintain stem cell self-renewal. For example, in GSCs, TLX represses TET3 expression to maintain GSC self-renewal. ATRA can activate TLX, turning it from a repressor to an activator.

It is expected that treatment of GSCs with ATRA would induce the expression of TET3, a tumor suppressor, to inhibit GSC growth, self-renewal and tumorigenesis. TET3 induction by ATRA would provide proof-of-concept that TLX can be activated by small molecules, which can be used to inhibit GSC self-renewal and tumorigenesis.

REFERENCES

1 Louis, D. N., Ohgaki, H., Wiestler, O. D., Cavenee, W. K., Burger, P. C., Jouvet, A., Scheithauer, B. W., and Kleihues, P. The 2007 WHO classification of tumours of the central nervous system. *Acta Neuropathol* 114, 97-109 (2007).
2 Singh, S. K., Hawkins, C., Clarke, I. D., Squire, J. A., Bayani, J., Hide, T., Henkelman, R. M., Cusimano, M. D., and Dirks, P. B. Identification of human brain tumour initiating cells. *Nature* 432, 396-401 (2004).
3 Bao, S., Wu, Q., McLendon, R. E., Hao, Y., Shi, Q., Hjelmeland, A. B., Dewhirst, M. W., Bigner, D. D., and Rich, J. N. Glioma stem cells promote radioresistance by preferential activation of the DNA damage response. *Nature* 444, 756-760 (2006).
4 Godlewski, J., Newton, H. B., Chiocca, E. A., and Lawler, S. E. MicroRNAs and glioblastoma; the stem cell connection. *Cell Death Differ* 17, 221-228 (2010).
5 Reya, T., Morrison, S. J., Clarke, M. F., and Weissman, I. L. Stem cells, cancer, and cancer stem cells. *Nature* 414, 105-111 (2001).
6 Tan, B. T., Park, C. Y., Ailles, L. E., and Weissman, I. L. The cancer stem cell hypothesis: a work in progress. *Lab Invest* 86, 1203-1207 (2006).
7 Antoniou, A., Hebrant, A., Dom, G., Dumont, J. E., and Maenhaut, C. Cancer stem cells, a fuzzy evolving concept: a cell population or a cell property? *Cell Cycle* 12, 3743-3748 (2013).

8. Sundar, S. J., Hsieh, J. K., Manjila, S., Lathia, J. D., and Sloan, A. The role of cancer stem cells in glioblastoma. *Neurosurg Focus* 37, E6 (2014).

9. Allegra, A., Alonci, A., Penna, G., Innao, V., Gerace, D., Rotondo, F., and Musolino, C. The cancer stem cell hypothesis: a guide to potential molecular targets. *Cancer Invest* 32, 470-495 (2014).

10. Yu, R. T., McKeown, M., Evans, R. M., and Umesono, K. Relationship between *Drosophila* gap gene tailless and a vertebrate nuclear receptor Tlx. *Nature* 370, 375-379 (1994).

11. Shi, Y., Lie, C. D., Taupin, P., Nakashima, K., Ray, J., Yu, R. T., Gage, F. H., and Evans, R. M. Expression and function of orphan nuclear receptor TLX in adult neural stem cells. *Nature* 427, 78-83 (2004).

12. Qu, Q., Sun, G., Li, W., Yang, S., Ye, P., Zhao, C., Yu, R. T., Gage, F. H., Evans, R. M., and Shi, Y. Orphan nuclear receptor TLX activates Wnt/beta-catenin signalling to stimulate neural stem cell proliferation and self-renewal. *Nat Cell Biol* 12, 31-40; sup pp 31-39 (2010).

13. Park, H. J., Kim, J. K., Jeon, H. M., Oh, S. Y., Kim, S. H., Park, M. J., Soeda, A., Nam, D. H., and Kim, H. The neural stem cell fate determinant TLX promotes tumorigenesis and genesis of cells resembling glioma stem cells. *Mol Cells* 30, 403-408 (2010).

14. Liu, H. K., Wang, Y., Belz, T., Bock, D., Takacs, A., Radlwimmer, B., Barbus, S., Reifenberger, G., Lichter, P., and Schutz, G. The nuclear receptor tailless induces long-term neural stem cell expansion and brain tumor initiation. *Genes Dev* 24, 683-695 (2010).

15. Yang, H., Liu, Y., Bai, F., Zhang, J. Y., Ma, S. H., Liu, J., Xu, Z. D., Zhu, H. G., Ling, Z. Q., Ye, D., Guan, K. L., and Xiong, Y. Tumor development is associated with decrease of TET gene expression and 5-methylcytosine hydroxylation. *Oncogene* 32, 663-669 (2013).

16. Haffner, M. C., Chaux, A., Meeker, A. K., Esopi, D. M., Gerber, J., Pellakuru, L. G., Toubaji, A., Argani, P., Iacobuzio-Donahue, C., Nelson, W. G., Netto, G. J., De Marzo, A. M., and Yegnasubramanian, S. Global 5-hydroxymethylcytosine content is significantly reduced in tissue stem/progenitor cell compartments and in human cancers. *Oncotarget* 2, 627-637 (2011).

17. Lian, C. G., Xu, Y., Ceol, C., Wu, F., Larson, A., Dresser, K., Xu, W., Tan, L., Hu, Y., Zhan, Q., Lee, C. W., Hu, D., Lian, B. Q., Kleffel, S., Yang, Y., Neiswender, J., Khorasani, A. J., Fang, R., Lezcano, C., Duncan, L. M., Scolyer, R. A., Thompson, J. F., Kakavand, H., Houvras, Y., Zon, L. I., Mihm, M. C., Jr., Kaiser, U. B., Schatton, T., Woda, B. A., Murphy, G. F., and Shi, Y. G. Loss of 5-hydroxymethylcytosine is an epigenetic hallmark of melanoma. *Cell* 150, 1135-1146 (2012).

18. Orr, B. A., Haffner, M. C., Nelson, W. G., Yegnasubramanian, S., and Eberhart, C. G. Decreased 5-hydroxymethylcytosine is associated with neural progenitor phenotype in normal brain and shorter survival in malignant glioma. *PLoS One* 7, e41036 (2012).

19. Jin, S. G., Jiang, Y., Qiu, R., Rauch, T. A., Wang, Y., Schackert, G., Krex, D., Lu, Q., and Pfeifer, G. P. 5-Hydroxymethylcytosine is strongly depleted in human cancers but its levels do not correlate with IDH1 mutations. *Cancer Res* 71, 7360-7365 (2011).

20. Xu, W., Yang, H., Liu, Y., Yang, Y., Wang, P., Kim, S. H., Ito, S., Yang, C., Wang, P., Xiao, M. T., Liu, L. X., Jiang, W. Q., Liu, J., Zhang, J. Y., Wang, B., Frye, S., Zhang, Y., Xu, Y. H., Lei, Q. Y., Guan, K. L., Zhao, S. M., and Xiong, Y. Oncometabolite 2-hydroxyglutarate is a competitive inhibitor of alpha-ketoglutarate-dependent dioxygenases. *Cancer Cell* 19, 17-30 (2011).

21. Tahiliani, M., Koh, K. P., Shen, Y., Pastor, W. A., Bandukwala, H., Brudno, Y., Agarwal, S., Iyer, L. M., Liu, D. R., Aravind, L., and Rao, A. Conversion of 5-methylcytosine to 5-hydroxymethylcytosine in mammalian DNA by MLL partner TET1. *Science* 324, 930-935 (2009).

22. Kriaucionis, S. and Heintz, N. The nuclear DNA base 5-hydroxymethylcytosine is present in Purkinje neurons and the brain. *Science* 324, 929-930 (2009).

23. Moran-Crusio, K., Reavie, L., Shih, A., Abdel-Wahab, O., Ndiaye-Lobry, D., Lobry, C., Figueroa, M. E., Vasanthakumar, A., Patel, J., Zhao, X., Perna, F., Pandey, S., Madzo, J., Song, C., Dai, Q., He, C., Ibrahim, S., Beran, M., Zavadil, J., Nimer, S. D., Melnick, A., Godley, L. A., Aifantis, I., and Levine, R. L. Tet2 loss leads to increased hematopoietic stem cell self-renewal and myeloid transformation. *Cancer Cell* 20, 11-24 (2011).

24. Quivoron, C., Couronne, L., Della Valle, V., Lopez, C. K., Plo, I., Wagner-Ballon, O., Do Cruzeiro, M., Delhommeau, F., Arnulf, B., Stern, M. H., Godley, L., Opolon, P., Tilly, H., Solary, E., Duffourd, Y., Dessen, P., Merle-Beral, H., Nguyen-Khac, F., Fontenay, M., Vainchenker, W., Bastard, C., Mercher, T., and Bernard, O. A. TET2 inactivation results in pleiotropic hematopoietic abnormalities in mouse and is a recurrent event during human lymphomagenesis. *Cancer Cell* 20, 25-38 (2011).

25. Song, S. J., Ito, K., Ala, U., Kats, L., Webster, K., Sun, S. M., Jongen-Lavrencic, M., Manova-Todorova, K., Teruya-Feldstein, J., Avigan, D. E., Delwel, R., and Pandolfi, P. P. The oncogenic microRNA miR-22 targets the TET2 tumor suppressor to promote hematopoietic stem cell self-renewal and transformation. *Cell Stem Cell* 13, 87-101 (2013).

26. Song, S. J., Poliseno, L., Song, M. S., Ala, U., Webster, K., Ng, C., Beringer, G., Brikbak, N. J., Yuan, X., Cantley, L. C., Richardson, A. L., and Pandolfi, P. P. MicroRNA-Antagonism Regulates Breast Cancer Stemness and Metastasis via TET-Family-Dependent Chromatin Remodeling. *Cell* 154, 311-324 (2013).

27. Haussecker, D. and Kay, M. A. RNA interference. Drugging RNAi. *Science* 347, 1069-1070 (2015).

28. Cambon, K. and Deglon, N. Lentiviral-mediated gene transfer of siRNAs for the treatment of Huntington's disease. *Methods Mol Biol* 1010, 95-109 (2013).

29. Tseng, Y. C., Mozumdar, S., and Huang, L. Lipid-based systemic delivery of siRNA. *Adv Drug Deliv Rev* 61, 721-731 (2009).

30. Whitehead, K. A., Langer, R., and Anderson, D. G. Knocking down barriers: advances in siRNA delivery. *Nat Rev Drug Discov* 8, 129-138 (2009).

31. Dutta, T., Garg, M., and Jain, N. K. Poly(propyleneimine) dendrimer and dendrosome mediated genetic immunization against hepatitis B. *Vaccine* 26, 3389-3394 (2008).

32. Wolinsky, J. B. and Grinstaff, M. W. Therapeutic and diagnostic applications of dendrimers for cancer treatment. *Adv Drug Deliv Rev* 60, 1037-1055 (2008).

33. Liu, X., Rocchi, P., and L., Peng Dendrimers as non-viral vectors for siRNA delivery. *New J Chem* 36, 256-263 (2012).

34. Liu, X., Liu, C., Catapano, C. V., Peng, L., Zhou, J., and Rocchi, P. Structurally flexible triethanolamine-core poly (amidoamine) dendrimers as effective nanovectors to deliver RNAi-based therapeutics. *Biotechnol Adv* 32, 844-852 (2014).

35 Behr, J. P. The proton sponge: A trick to enter cells the viruses did not exploit. *Chimia* 51, 34-36 (1997).
36 Brown, C. E., Starr, R., Martinez, C., Aguilar, B., D'Apuzzo, M., Todorov, I., Shih, C. C., Badie, B., Hudecek, M., Riddell, S. R., and Jensen, M. C. Recognition and killing of brain tumor stem-like initiating cells by CD8+ cytolytic T cells. *Cancer Res* 69, 8886-8893 (2009).
37 Verhaak, R. G., Hoadley, K. A., Purdom, E., Wang, V., Qi, Y., Wilkerson, M. D., Miller, C. R., Ding, L., Golub, T., Mesirov, J. P., Alexe, G., Lawrence, M., O'Kelly, M., Tamayo, P., Weir, B. A., Gabriel, S., Winckler, W., Gupta, S., Jakkula, L., Feiler, H. S., Hodgson, J. G., James, C. D., Sarkaria, J. N., Brennan, C., Kahn, A., Spellman, P. T., Wilson, R. K., Speed, T. P., Gray, J. W., Meyerson, M., Getz, G., Perou, C. M., and Hayes, D. N. Integrated genomic analysis identifies clinically relevant subtypes of glioblastoma characterized by abnormalities in PDGFRA, IDH1, EGFR, and NF1. *Cancer Cell* 17, 98-110 (2010).
38 Zhou, J., Wu, J., Hafdi, N., Behr, J. P., Erbacher, P., and Peng, L. PAMAM dendrimers for efficient siRNA delivery and potent gene silencing. *Chem Commun (Camb)*, 2362-2364 (2006).
39 Zhou, J., Neff, C. P., Liu, X., Zhang, J., Li, H., Smith, D. D., Swiderski, P., Aboellail, T., Huang, Y., Du, Q., Liang, Z., Peng, L., Akkina, R., and Rossi, J. J. Systemic administration of combinatorial dsiRNAs via nanoparticles efficiently suppresses HIV-1 infection in humanized mice. *Mol Ther* 19, 2228-2238 (2011).
40 Liu, X., Liu, C., Chen, C., Bentobji, M., Cheillan, F. A., Piana, J. T., Qu, F., Rocchi, P., and Peng, L. Targeted delivery of Dicer-substrate siRNAs using a dual targeting peptide decorated dendrimer delivery system. *Nanomedicine* 10, 1627-1636 (2014).
41 Desgrosellier, J. S. and Cheresh, D. A. Integrins in cancer: biological implications and therapeutic opportunities. *Nat Rev Cancer* 10, 9-22 (2010).
42 Teesalu, T., Sugahara, K. N., Kotamraju, V. R., and Ruoslahti, E. C-end rule peptides mediate neuropilin-1-dependent cell, vascular, and tissue penetration. *Proc Natl Acad Sci USA* 106, 16157-16162 (2009).
43 Sugahara, K. N., Teesalu, T., Karmali, P. P., Kotamraju, V. R., Agemy, L., Girard, O. M., Hanahan, D., Mattrey, R. F., and Ruoslahti, E. Tissue-penetrating delivery of compounds and nanoparticles into tumors. *Cancer Cell* 16, 510-520 (2009).
44 Zhou, J., Liu, J., Cheng, C. J., Patel, T. R., Weller, C. E., Piepmeier, J. M., Jiang, Z., and Saltzman, W. M. Biodegradable poly(amine-co-ester) terpolymers for targeted gene delivery. *Nat Mater* 11, 82-90 (2012).
45 Sun, G., Yu, R. T., Evans, R. M., and Shi, Y. Orphan nuclear receptor TLX recruits histone deacetylases to repress transcription and regulate neural stem cell proliferation. *Proc Natl Acad Sci USA* 104, 15282-15287 (2007).
46 Zou, Y., Niu, W., Qin, S., Downes, M., Burns, D. K., and Zhang, C. L. The nuclear receptor TLX is required for gliomagenesis within the adult neurogenic niche. *Mol Cell Biol* 32, 4811-4820 (2012).
47 Zhu, Z., Khan, M. A., Weiler, M., Blaes, J., Jestaedt, L., Geibert, M., Zou, P., Gronych, J., Bernhardt, O., Korshunov, A., Bugner, V., Lichter, P., Radlwimmer, B., Heiland, S., Bendszus, M., Wick, W., and Liu, H. K. Targeting Self-Renewal in High-Grade Brain Tumors Leads to Loss of Brain Tumor Stem Cells and Prolonged Survival. *Cell Stem Cell* 15, 185-198 (2014).
48 Liu, N., Wang, M., Deng, W., Schmidt, C. S., Qin, W., Leonhardt, H., and Spada, F. Intrinsic and extrinsic connections of Tet3 dioxygenase with CXXC zinc finger modules. *PLoS One* 8, e62755 (2013).
49 Perera, A., Eisen, D., Wagner, M., Laube, S. K., Kunzel, A. F., Koch, S., Steinbacher, J., Schulze, E., Splith, V., Mittermeier, N., Muller, M., Biel, M., Carell, T., and Michalakis, S. TET3 is recruited by REST for context-specific hydroxymethylation and induction of gene expression. *Cell Rep* 11, 283-294 (2015).
50 Xu, Y., Xu, C., Kato, A., Tempel, W., Abreu, J. G., Bian, C., Hu, Y., Hu, D., Zhao, B., Cerovina, T., Diao, J., Wu, F., He, H. H., Cui, Q., Clark, E., Ma, C., Barbara, A., Veenstra, G. J., Xu, G., Kaiser, U. B., Liu, X. S., Sugrue, S. P., He, X., Min, J., Kato, Y., and Shi, Y. G. Tet3 CXXC domain and dioxygenase activity cooperatively regulate key genes for Xenopus eye and neural development. *Cell* 151, 1200-1213 (2012).
51 Kim, Y., Kim, E., Wu, Q., Guryanova, O., Hitomi, M., Lathia, J. D., Serwanski, D., Sloan, A. E., Weil, R. J., Lee, J., Nishiyama, A., Bao, S., Hjelmeland, A. B., and Rich, J. N. Platelet-derived growth factor receptors differentially inform intertumoral and intratumoral heterogeneity. *Genes Dev* 26, 1247-1262 (2012).
52 Yan, K., Wu, Q., Yan, D. H., Lee, C. H., Rahim, N., Tritschler, I., DeVecchio, J., Kalady, M. F., Hjelmeland, A. B., and Rich, J. N. Glioma cancer stem cells secrete Gremlin1 to promote their maintenance within the tumor hierarchy. *Genes Dev* 28, 1085-1100 (2014).
53 Ito, S., D'Alessio, A. C., Taranova, O. V., Hong, K., Sowers, L. C., and Zhang, Y. Role of Tet proteins in 5mC to 5hmC conversion, ES-cell self-renewal and inner cell mass specification. *Nature* 466, 1129-1133 (2010).
54 Jin, K., Zhu, Y., Sun, Y., Mao, X. O., Xie, L., and Greenberg, D. A. Vascular endothelial growth factor (VEGF) stimulates neurogenesis in vitro and in vivo. *Proc Natl Acad Sci USA* 99, 11946-11950 (2002).
55 Zhao, C., Sun, G., Li, S., Lang, M., Yang, S., Li, W., and Shi, Y. microRNA let-7b regulates neural stem cell proliferation and differentiation by targeting nuclear receptor TLX signaling. *Proc Natl Acad Sci USA* 107, 1876-1881 (2010).
56 Irizarry, R. A., Hobbs, B., Collin, F., Beazer-Barclay, Y. D., Antonellis, K. J., Scherf, U., and Speed, T. P. Exploration, normalization, and summaries of high density oligonucleotide array probe level data. Biostatistics 4, 249-264 (2003).
57 Hu, Y. and Smyth, G. K. ELDA: extreme limiting dilution analysis for comparing depleted and enriched populations in stem cell and other assays. *J Immunol Methods* 347, 70-78 (2009).
58. Adaptive amphiphilic dendrimer-based nanoassemblies as robust and versatile siRNA delivery systems. Liu X, Zhou J, Yu T, Chen C, Cheng Q, Sengupta K, Huang Y, Li H, Liu C, Wang Y, Posocco P, Wang M, Cui Q, Giorgio S, Fermeglia M, Qu F, Pricl S, Shi Y, Liang Z, Rocchi P, Rossi J J, Peng L. Angew Chem Int Ed Engl. 2014; 53(44):11822-7. doi: 10.1002/anie.201406764.
59. An amphiphilic dendrimer for effective delivery of small interfering RNA and gene silencing in vitro and in vivo. Yu Tl, Liu X, Bolcato-Bellemin A L, Wang Y, Liu C, Erbacher P, Qu F, Rocchi P, Behr J P, Peng L. Angew Chem Int Ed Engl. 2012; 51(34):8478-84. doi: 10.1002/anie.201203920.
60. Promoting siRNA delivery via enhanced cellular uptake using an arginine-decorated amphiphilic dendrimer. Liu Xl, Liu C, Zhou J, Chen C, Qu F, Rossi J J, Rocchi P, Peng L. Nanoscale. 2015; 7(9):3867-75. doi: 10.1039/c4nr04759a.

61. BTG2 inhibits the proliferation and metastasis of osteosarcoma cells by suppressing the PI3K/AKT pathway. Li Y J, Dong B K, Fan M, Jiang W X. Int J Clin Exp Pathol. 2015; 8(10):12410-8. eCollection 2015. PMID: 26722427
62. Clinical significance of expression and epigenetic profiling of TUSC1 in gastric cancer. Kanda M, Shimizu D, Nomoto S, Hibino S, Oya H, Takami H, Kobayashi D, Yamada S, Inokawa Y, Tanaka C, Fujii T, Sugimoto H, Koike M, Fujiwara M, Kodera Y. J Surg Oncol. 2014; 110(2):136-44. doi: 10.1002/jso.23614. PMID: 24700496
63. Identification of intragenic methylation in the TUSC1 gene as a novel prognostic marker of hepatocellular carcinoma. Shimizu D, Kanda M, Nomoto S, Oya H, Takami H, Hibino S, Suenaga M, Inokawa Y, Hishida M, Takano N, Nishikawa Y, Yamada S, Fujii T, Nakayama G, Sugimoto H, Koike M, Fujiwara M, Kodera Y. Oncol Rep. 2014; 31(3):1305-13. doi: 10.3892/or.2013.2939. PMID: 24366000
64. TUSC1, a putative tumor suppressor gene, reduces tumor cell growth in vitro and tumor growth in vivo. Shan Z, Shakoori A, Bodaghi S, Goldsmith P, Jin J, Wiest J S. PLoS One. 2013; 8(6):e66114. doi: 10.1371/journal.pone.0066114. PMID: 23776618
65. Alterations in the NF2/LATS1/LATS2/YAP Pathway in Schwannomas. Oh JE1, Ohta T, Satomi K, Foll M, Durand G, McKay J, Le Calvez-Kelm F, Mittelbronn M, Brokinkel B, Paulus W, Ohgaki H. J Neuropathol Exp Neurol. 2015; 74(10):952-9. doi: 10.1097/NEN.0000000000000238.
66. MicroRNA-587 antagonizes 5-FU-induced apoptosis and confers drug resistance by regulating PPP2R1B expression in colorectal cancer. Zhang Y, Talmon G, Wang J. Cell Death Dis. 2015; 6:e1845. doi: 10.1038/cddis.2015.200.

What is claimed is:

1. A method of treating an individual suspected of, having, or diagnosed with brain cancer by administering a composition that modulates TLX activity, wherein the composition that modulates TLX activity comprises an shRNA suitable to induce degradation of TLX and, wherein the shRNA comprises one or more of SEQ ID NO: 1 or SEQ ID NO: 3.

2. The method of claim 1, wherein the brain cancer is selected from the group consisting of glioblastoma, oligodendroglioma, dysembryoplastic neuroepithelial tumor, mesenchymal gliomas, pilocytic astrocytomas, neurocytoma, and ependymoma.

3. A method of treating an individual suspected of, having, or diagnosed with brain cancer by administering a composition that modulates TLX activity, wherein the composition that modulates TLX activity comprises an siRNA suitable to induce degradation of TLX and, wherein the siRNA comprises one or more of SEQ ID NO: 51-54.

4. The method of claim 3, wherein the composition that modulates TLX activity is complexed with a nanoparticle.

5. The method of claim 4, wherein the nanoparticle comprises a dendrimer.

6. The method of claim 5, wherein the dendrimer is a poly(amidoamine) (PAMAM) dendrimer.

7. The method of claim 1, wherein the composition upregulates expression of TET3.

8. A method of downregulating TLX expression by administering an agent to target TLX for degradation to a subject in need thereof, wherein the agent comprises an siRNA suitable to induce degradation of TLX and, wherein the siRNA comprises one or more of SEQ ID NO: 51-54.

9. The method of claim 8, wherein the agent is complexed with a nanoparticle.

10. The method of claim 9, wherein the nanoparticle comprises a dendrimer.

11. The method of claim 10, wherein the dendrimer is a poly(amidoamine) (PAMAM) dendrimer.

12. The method of claim 8, wherein the subject in need thereof is an individual diagnosed with brain cancer.

13. The method claim 12, wherein the brain cancer is selected from the group consisting of glioblastoma, oligodendroglioma, dysembryoplastic neuroepithelial tumor, mesenchymal gliomas, pilocytic astrocytomas, neurocytoma, and ependymoma.

14. A composition for the treatment of brain cancer comprising an siRNA targeting TLX complexed with a dendrimer, wherein the siRNA comprises one or more of SEQ ID NO: 51-54.

15. The composition of claim 14, wherein the dendrimer is a poly(amidoamine) (PAMAM) dendrimer.

16. The composition of claim 15, wherein the PAMAM dendrimer comprises a peptide coating.

17. The composition of claim 16, wherein the peptide coating comprises RGDK.

* * * * *

SEQUENCE LISTING

```
<160> NUMBER OF SEQ ID NOS: 55

<210> SEQ ID NO 1
<211> LENGTH: 21
<212> TYPE: RNA
<213> ORGANISM: Artificial Sequence
<220> FEATURE:
<223> OTHER INFORMATION: TLX shRNA-1

<400> SEQUENCE: 1
gccgccattg cagcccttca a                                             21

<210> SEQ ID NO 2
<211> LENGTH: 21
<212> TYPE: RNA
<213> ORGANISM: Artificial Sequence
<220> FEATURE:
<223> OTHER INFORMATION: TLX shRNA-1 scrambled control

<400> SEQUENCE: 2
cagtccatca gaccctcgct g                                             21

<210> SEQ ID NO 3
<211> LENGTH: 21
<212> TYPE: RNA
<213> ORGANISM: Artificial Sequence
<220> FEATURE:
<223> OTHER INFORMATION: TLX shRNA-2

<400> SEQUENCE: 3
ggaagtcaac atgaacaaag a                                             21

<210> SEQ ID NO 4
<211> LENGTH: 21
<212> TYPE: RNA
<213> ORGANISM: Artificial Sequence
<220> FEATURE:
<223> OTHER INFORMATION: TLX shRNA-2 scrambled control

<400> SEQUENCE: 4
actcaaaagg aagtgacaag a                                             21

<210> SEQ ID NO 5
<211> LENGTH: 19
<212> TYPE: RNA
<213> ORGANISM: Artificial Sequence
<220> FEATURE:
<223> OTHER INFORMATION: shRNA control for TET3
```

```
<400> SEQUENCE: 5
gttcagatgt gcggcgagt                                              19

<210> SEQ ID NO 6
<211> LENGTH: 19
<212> TYPE: RNA
<213> ORGANISM: Artificial Sequence
<220> FEATURE:
<223> OTHER INFORMATION: shTET3-1

<400> SEQUENCE: 6
ccgaagctgt gtcctctta                                              19

<210> SEQ ID NO 7
<211> LENGTH: 19
<212> TYPE: RNA
<213> ORGANISM: Artificial Sequence
<220> FEATURE:
<223> OTHER INFORMATION: shTET3-2

<400> SEQUENCE: 7
ggagtcacct cttaagtac                                              19

<210> SEQ ID NO 8
<211> LENGTH: 19
<212> TYPE: DNA
<213> ORGANISM: Artificial Sequence
<220> FEATURE:
<223> OTHER INFORMATION: Primer Seqeunce

<400> SEQUENCE: 8
cctgttcgac agtcagccg                                              19

<210> SEQ ID NO 9
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 9
cgaccaaatc cgttgactcc                                             20

<210> SEQ ID NO 10
<211> LENGTH: 22
<212> TYPE: DNA
<213> ORGANISM: Artificial Sequence
<220> FEATURE:
<223> OTHER INFORMATION: Primer Seqeunce

<400> SEQUENCE: 10
ccgcaaagac ctgtacgcca ac                                          22

<210> SEQ ID NO 11
<211> LENGTH: 22
<212> TYPE: DNA
<213> ORGANISM: Artificial Sequence
<220> FEATURE:
<223> OTHER INFORMATION: Primer Seqeunce

<400> SEQUENCE: 11
ccagggcagt gatctccttc tg                                          22

<210> SEQ ID NO 12
```

```
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 12
ctaagagtgt gccagccttc                                               20

<210> SEQ ID NO 13
<211> LENGTH: 21
<212> TYPE: DNA
<213> ORGANISM: Artificial Sequence
<220> FEATURE:
<223> OTHER INFORMATION: Primer Seqeunce

<400> SEQUENCE: 13
tgttagcatc aaccggaatg g                                             21

<210> SEQ ID NO 14
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 14
cagcagccga gaagaagaag                                               20

<210> SEQ ID NO 15
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 15
ggacaatcca cccttcagag                                               20

<210> SEQ ID NO 16
<211> LENGTH: 21
<212> TYPE: DNA
<213> ORGANISM: Artificial Sequence
<220> FEATURE:
<223> OTHER INFORMATION: Primer Seqeunce

<400> SEQUENCE: 16
ctccatctgc gtcttgtacg a                                             21

<210> SEQ ID NO 17
<211> LENGTH: 21
<212> TYPE: DNA
<213> ORGANISM: Artificial Sequence
<220> FEATURE:
<223> OTHER INFORMATION: Primer Seqeunce

<400> SEQUENCE: 17
agactgccat cacgtagttc t                                             21

<210> SEQ ID NO 18
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 18
```
tgaagaggcc agcacgaacc                                               20

<210> SEQ ID NO 19
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 19
agtcgggttc ctgtagaggc                                               20

<210> SEQ ID NO 20
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 20
gctcccaacc cattcactac                                               20

<210> SEQ ID NO 21
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 21
tccctactcc ttttccctga                                               20

<210> SEQ ID NO 22
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 22
gtgtctaact gtcggtgtgg                                               20

<210> SEQ ID NO 23
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 23
tcactccaac actccaccag                                               20

<210> SEQ ID NO 24
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 24
cgatagcaca gcctgcaata                                               20

<210> SEQ ID NO 25
<211> LENGTH: 20
<212> TYPE: DNA

<213> ORGANISM: Artificial Sequence
<220> FEATURE:
<223> OTHER INFORMATION: Primer Seqeunce

<400> SEQUENCE: 25
acggtgcaag ccttatttttg                                              20

<210> SEQ ID NO 26
<211> LENGTH: 18
<212> TYPE: DNA
<213> ORGANISM: Artificial Sequence
<220> FEATURE:
<223> OTHER INFORMATION: Primer Seqeunce

<400> SEQUENCE: 26
ttccactgtt cactagtc                                                 18

<210> SEQ ID NO 27
<211> LENGTH: 19
<212> TYPE: DNA
<213> ORGANISM: Artificial Sequence
<220> FEATURE:
<223> OTHER INFORMATION: Primer Seqeunce

<400> SEQUENCE: 27
ccaaagtctc aaggtcatc                                                19

<210> SEQ ID NO 28
<211> LENGTH: 22
<212> TYPE: DNA
<213> ORGANISM: Artificial Sequence
<220> FEATURE:
<223> OTHER INFORMATION: Primer Seqeunce

<400> SEQUENCE: 28
gacaactccg gttagatgct ac                                            22

<210> SEQ ID NO 29
<211> LENGTH: 21
<212> TYPE: DNA
<213> ORGANISM: Artificial Sequence
<220> FEATURE:
<223> OTHER INFORMATION: Primer Seqeunce

<400> SEQUENCE: 29
gagcctcatc ttgaagggct g                                             21

<210> SEQ ID NO 30
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 30
ggcctgggtc cgacgtaatg                                               20

<210> SEQ ID NO 31
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 31
cctatgaggt gtcctaccgc                                               20

<210> SEQ ID NO 32
<211> LENGTH: 19
<212> TYPE: DNA
<213> ORGANISM: Artificial Sequence
<220> FEATURE:
<223> OTHER INFORMATION: Primer Seqeunce

<400> SEQUENCE: 32
ctccggccca gcagcactt                                                    19

<210> SEQ ID NO 33
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 33
ttgagaagag gcatccatcc                                                   20

<210> SEQ ID NO 34
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 34
agaaccacag tcgtttcctg                                                   20

<210> SEQ ID NO 35
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 35
tgtaatccca gctcctgagg                                                   20

<210> SEQ ID NO 36
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 36
ggttgacaga ctgaacaggg                                                   20

<210> SEQ ID NO 37
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 37
attctagccc accactcacc                                                   20

<210> SEQ ID NO 38
<211> LENGTH: 20
<212> TYPE: DNA
<213> ORGANISM: Artificial Sequence
<220> FEATURE:

<223> OTHER INFORMATION: Primer Seqeunce

<400> SEQUENCE: 38
tgtgccaacc atgttgtagg                                          20

<210> SEQ ID NO 39
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 39
tggctcagag aacctcaagg                                          20

<210> SEQ ID NO 40
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 40
actgccctcc tctgtcattg                                          20

<210> SEQ ID NO 41
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 41
cctgtcgcaa agtcagaatc                                          20

<210> SEQ ID NO 42
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 42
tgcccttgtt ctcaggatac                                          20

<210> SEQ ID NO 43
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 43
gtgtgtacac acaggcttgg                                          20

<210> SEQ ID NO 44
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 44
tcacacaaat gaggctctcc                                          20

```
<210> SEQ ID NO 45
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 45
gaagaccagg tcagggtctg                                               20

<210> SEQ ID NO 46
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 46
aaggcaaggc ttagaagtgg                                               20

<210> SEQ ID NO 47
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 47
acctccctgg acctcctgaa                                               20

<210> SEQ ID NO 48
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 48
tcagtgagag gtctcgggtg                                               20

<210> SEQ ID NO 49
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 49
caacgagctg gatgaatccc                                               20

<210> SEQ ID NO 50
<211> LENGTH: 20
<212> TYPE: DNA
<213> ORGANISM: Artificial Sequence
<220> FEATURE:
<223> OTHER INFORMATION: Primer Seqeunce

<400> SEQUENCE: 50
ttaaggctcc cttctgaccc                                               20

<210> SEQ ID NO 51
<211> LENGTH: 25
<212> TYPE: RNA
<213> ORGANISM: Artificial Sequence
<220> FEATURE:
<223> OTHER INFORMATION: TLX siRNA sense
<220> FEATURE:
```

```
<221> NAME/KEY: misc_feature
<222> LOCATION: (24)..(24)
<223> OTHER INFORMATION: n is deoxyguanosine (dG)
<220> FEATURE:
<221> NAME/KEY: misc_feature
<222> LOCATION: (25)..(25)
<223> OTHER INFORMATION: n is deoxyadenosine (dA)

<400> SEQUENCE: 51
ccgccauugc agcccuucaa gaunn                                              25

<210> SEQ ID NO 52
<211> LENGTH: 27
<212> TYPE: RNA
<213> ORGANISM: Artificial Sequence
<220> FEATURE:
<223> OTHER INFORMATION: TLX siRNA antisense

<400> SEQUENCE: 52
ucaucuugaa gggcugcaau ggcgggg                                            27

<210> SEQ ID NO 53
<211> LENGTH: 25
<212> TYPE: RNA
<213> ORGANISM: Artificial Sequence
<220> FEATURE:
<223> OTHER INFORMATION: Control siRNA sense
<220> FEATURE:
<221> NAME/KEY: misc_feature
<222> LOCATION: (24)..(24)
<223> OTHER INFORMATION: n is deoxyguanosine (dG)
<220> FEATURE:
<221> NAME/KEY: misc_feature
<222> LOCATION: (25)..(25)
<223> OTHER INFORMATION: n is deoxyadenosine (dA)

<400> SEQUENCE: 53
cauccaucag acccucgcug gaunn                                              25

<210> SEQ ID NO 54
<211> LENGTH: 27
<212> TYPE: RNA
<213> ORGANISM: Artificial Sequence
<220> FEATURE:
<223> OTHER INFORMATION: Control siRNA antisense

<400> SEQUENCE: 54
ucauccagcg aggucugau ggauggg                                             27

<210> SEQ ID NO 55
<211> LENGTH: 26
<212> TYPE: PRT
<213> ORGANISM: Artificial Sequence
<220> FEATURE:
<223> OTHER INFORMATION: Syntehtic Sequence

<400> SEQUENCE: 55

Glu Glu Glu Glu Glu Glu Glu Glu Glu Glu Glu Glu Glu Glu Glu Glu
1               5                   10                  15

Gly Gly Gly Gly Gly Gly Arg Gly Asp Lys
            20                  25
```